(12) United States Patent
Kouji et al.

(10) Patent No.: US 12,024,571 B2
(45) Date of Patent: Jul. 2, 2024

(54) ANTI-ERYTHROPOIETIN RECEPTOR PEPTIDE

(71) Applicant: Epo-Med Inc., Tokyo (JP)

(72) Inventors: Hiroyuki Kouji, Tokyo (JP); Yoshiko Yasuda, Tokyo (JP); Akira Katoh, Yufu (JP); Hiroshi Ochi, Kyoto (JP)

(73) Assignee: Epo-Med Inc., Tokyo (JP)

( * ) Notice: Subject to any disclaimer, the term of this patent is extended or adjusted under 35 U.S.C. 154(b) by 0 days.

(21) Appl. No.: 17/276,101

(22) PCT Filed: Sep. 12, 2019

(86) PCT No.: PCT/JP2019/035949
§ 371 (c)(1),
(2) Date: Mar. 12, 2021

(87) PCT Pub. No.: WO2020/054813
PCT Pub. Date: Mar. 19, 2020

(65) Prior Publication Data
US 2022/0041657 A1    Feb. 10, 2022

(30) Foreign Application Priority Data
Sep. 14, 2018 (JP) ................................. 2018-172497

(51) Int. Cl.
| C07K 7/08 | (2006.01) |
| A61P 15/00 | (2006.01) |
| A61P 27/02 | (2006.01) |
| A61P 35/00 | (2006.01) |
| A61P 35/02 | (2006.01) |
| A61K 38/00 | (2006.01) |

(52) U.S. Cl.
CPC ................ *C07K 7/08* (2013.01); *A61P 15/00* (2018.01); *A61P 27/02* (2018.01); *A61P 35/00* (2018.01); *A61P 35/02* (2018.01); *A61K 38/00* (2013.01)

(58) Field of Classification Search
None
See application file for complete search history.

(56) References Cited

U.S. PATENT DOCUMENTS

| 2004/0266676 | A1 | 12/2004 | Yasuda | |
| 2007/0099917 | A1* | 5/2007 | Nice | ........................ A61P 17/06 514/266.4 |
| 2008/0305985 | A1 | 12/2008 | Frank et al. | |
| 2010/0323949 | A1* | 12/2010 | Lu | ........................... A61P 37/02 514/21.4 |
| 2022/0041657 | A1 | 2/2022 | Kouji et al. | |

FOREIGN PATENT DOCUMENTS

| JP | 11-507367 A | 6/1999 |
| JP | 2003-201252 A | 7/2003 |
| JP | 2003-534384 A | 11/2003 |
| JP | 2007-529475 A | 10/2007 |
| WO | 96/40749 A1 | 12/1996 |
| WO | 01/91780 A1 | 12/2001 |
| WO | 2005/090389 A2 | 9/2005 |
| WO | 2017/014312 A1 | 1/2017 |
| WO | WO 2020054813 A1 | 3/2020 |

OTHER PUBLICATIONS

Johnson et al. ('Identification of a 13 amino acid peptide mimetic of erythropoietin and description of amino acids critical for the mimetic activity of EMP1' Biochemistry v37 1998 pp. 3699-3710) (Year: 1998).*
Koide et al. ('The importance of being tyrosine: lessons in molecular recognition from minimalist synthetic binding proteins' ACS Chem Biol May 2009 v4(5) printed as pp. 1-16) (Year: 2009).*
Rowe et al. ('Stability of non-proteinogenic amino acids to UV and gamma irradiation' International Journal of Astrobiology v18 Oct. 8, 2018 pp. 426-435) (Year: 2018).*
Kwon et al. ('Site-specific incorporation of tryptophan analogues into recombinant proteins in bacterial cells' JACS v129 2007 pp. 10431-10437) (Year: 2007).*
D'Andrea et al., "Expression Cloning of the Murine Erythropoietin Receptor," *Cell* 57:277-285, 1989.
Krantz, "Erythropoietin," *Blood* 77(3):419-434, 1991.
Marti et al., "Erythropoietin Gene Expression in Human, Monkey and Murine Brain," *European Journal of Neuroscience* 8:666-676, 1996.
Yasuda et al., "Estrogen-dependent Production of Erythropoietin in Uterus and Its Implication in Uterine Angiogenesis," *The Journal of Biological Chemistry* 273(39):25381-25387, 1998.
Yasuda et al., "Localization of Erythropoeitin and Erythropoietin-Receptor in Postimplantation Mouse Embryos," *Develop. Growth & Differ.* 35(6):711-722, 1993.
Yasuda et al., "Significance of Erythropoietin Receptor Antagonist EMP9 in Cancers," *Vitamins and Hormones* 105:297-310, 2017.
Yasuda et al., "Localization of Erythropoietin and Erythropoietin-Receptor in Postimplantation Mouse Embryos," *Develop. Growth & Differ.* 35(6):711-722, 1993.

(Continued)

*Primary Examiner* — Ronald T Niebauer
(74) *Attorney, Agent, or Firm* — Seed IP Law Group LLP

(57) ABSTRACT

The present specification provides an anti-EpoR peptide. A peptide having the structure represented by formula (I): V-SCH($A^1$)($A^2$)($A^3$)($A^4$)($A^5$)($A^6$)v($A^7$)($A^8$)-$X^2$ (wherein $X^1$ is the amino terminal side of the peptide; $X^2$ is the carboxy terminal side of the peptide; $A^1$ is M or F, phenylglycine or phenethylglycine optionally substituted by a halogen atom or a hydroxyl group; $A^2$ is A, d-alanine or G; $A^3$ is P, homoproline or A; $A^4$ is M, L, A or I; $A^5$ is T or A; $A^6$ is M or W, F, Y, β-homotryptophan, α-naphthylalanine, β-naphthylalanine, or quinolylalanine optionally substituted by methyl or a halogen atom; $A^7$ is C, homocysteine, or penicillamine; and $A^8$ is K, R or absent) is provided.

1 Claim, 51 Drawing Sheets
Specification includes a Sequence Listing.

(56) References Cited

OTHER PUBLICATIONS

Partial Supplementary European Search Report, dated May 30, 2022, for European Application No. 19860376.3. (17 pages).
Brines et al., "The Receptor That Tames the Innate Immune Response," *Molecular Medicine* 18:486-496, 2012, 11 pages.

* cited by examiner

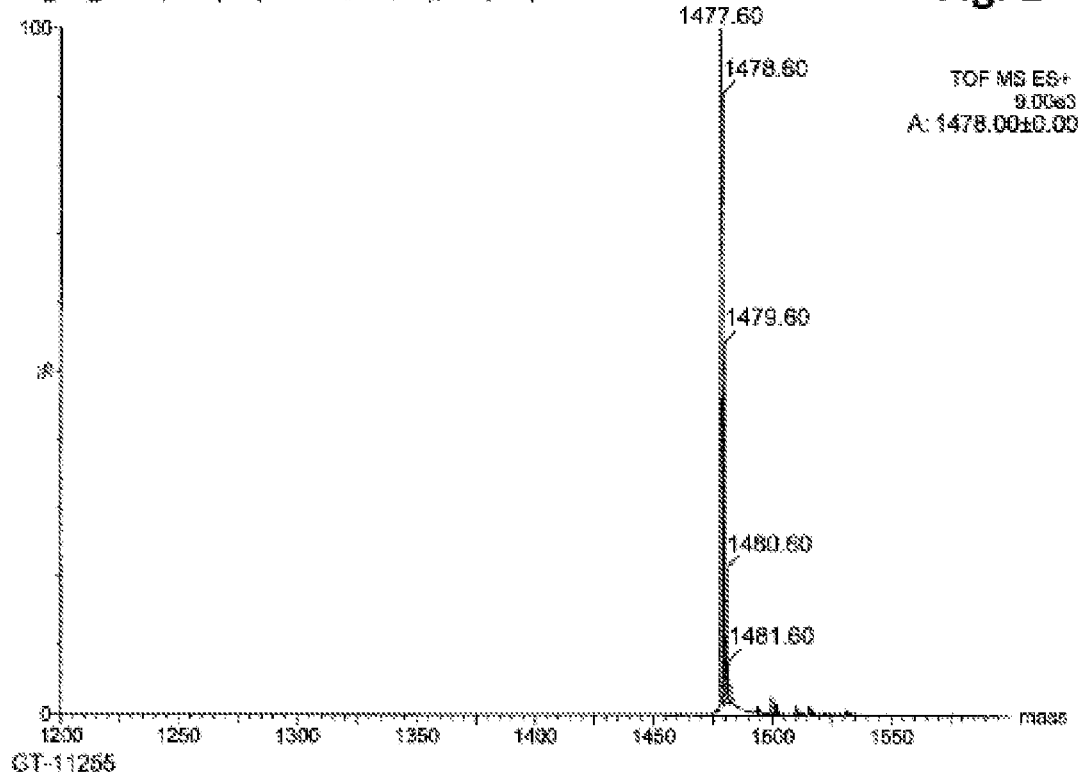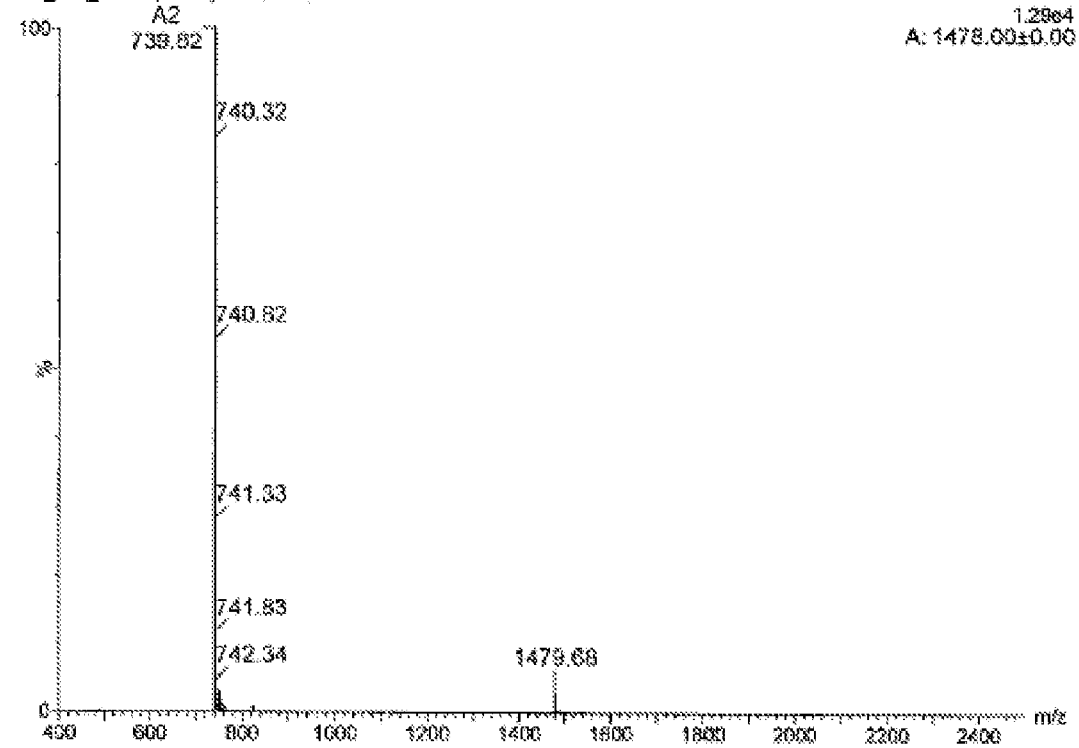
Fig. 1

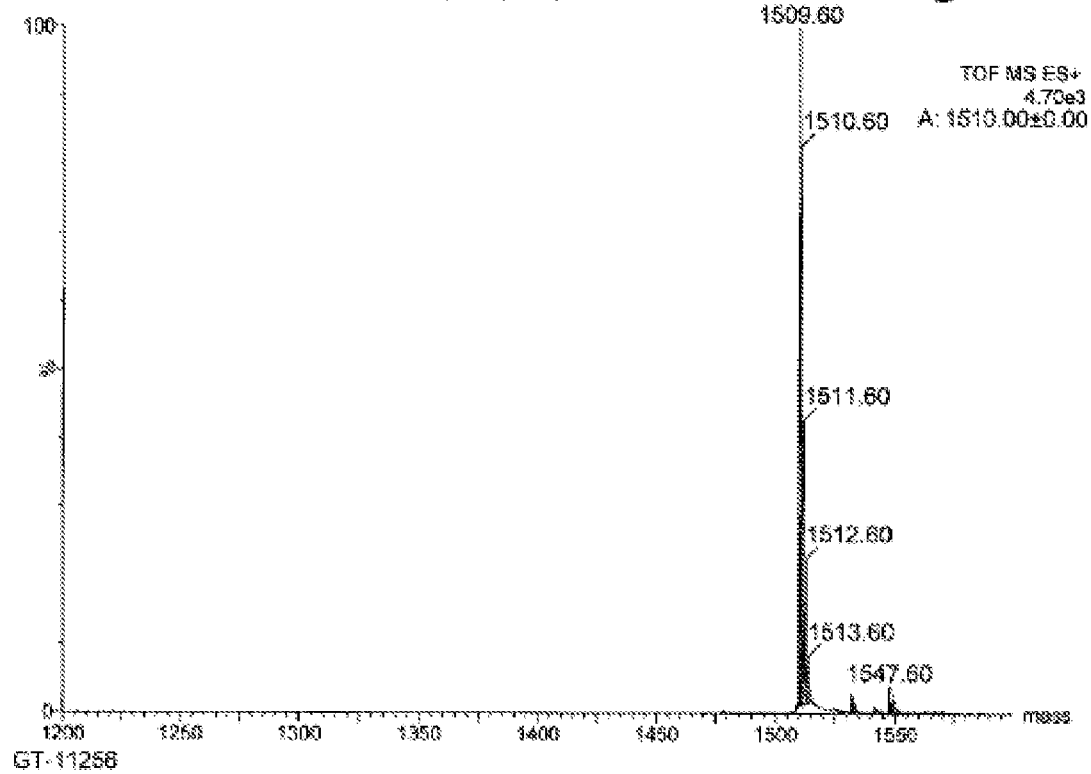
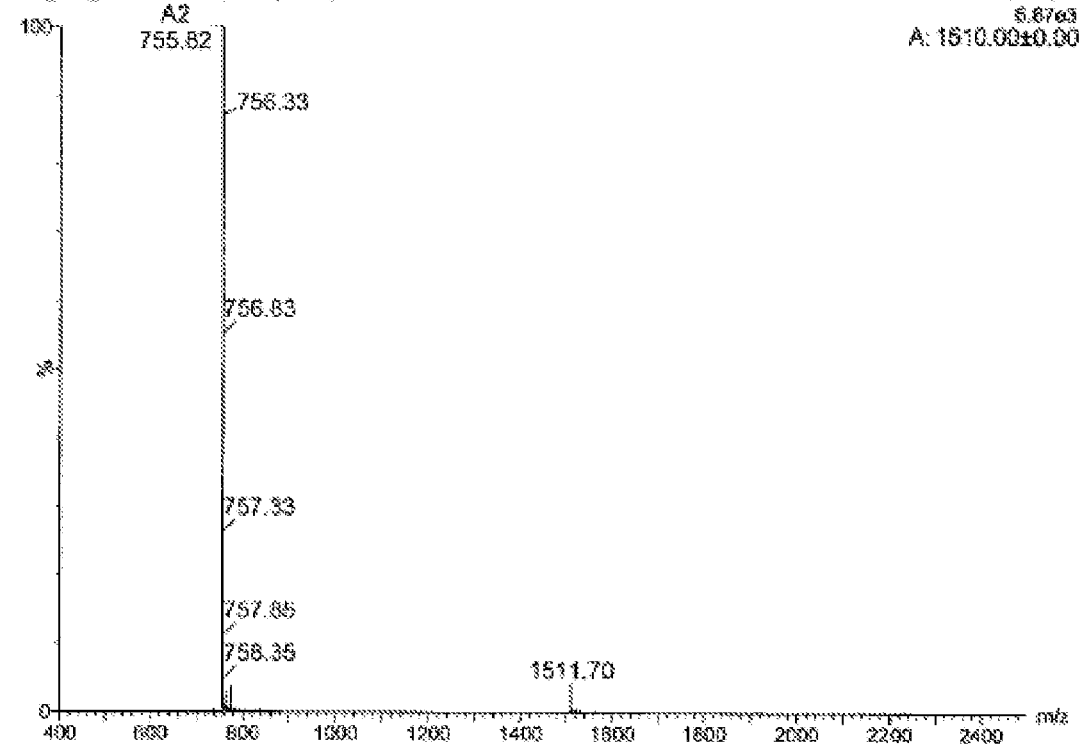
Fig. 2

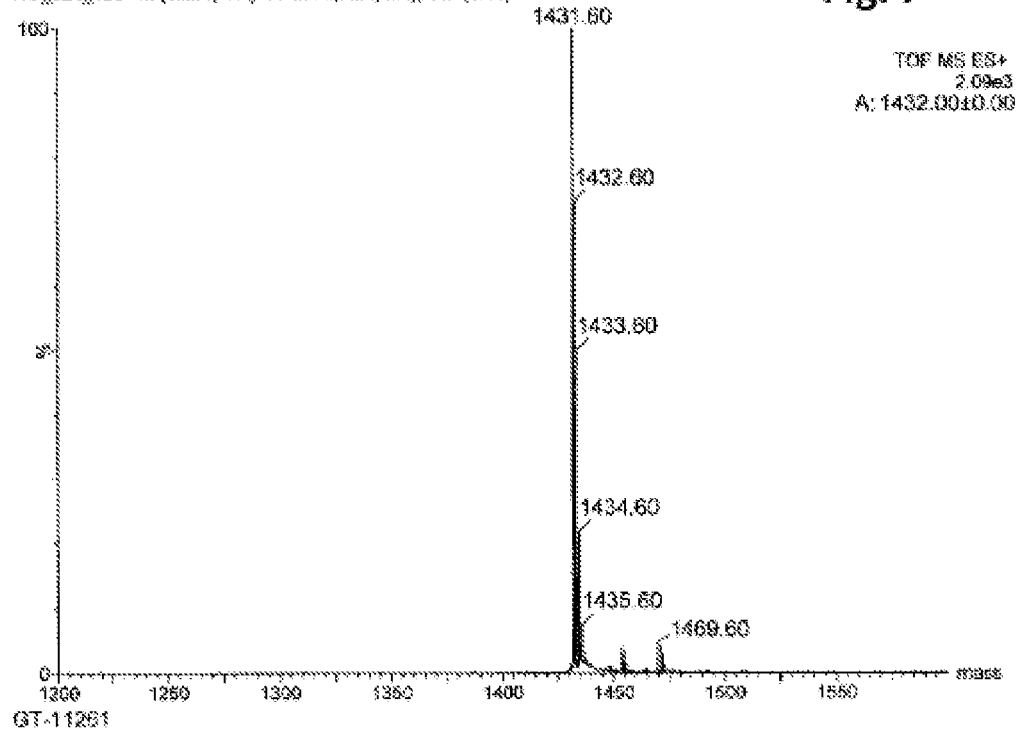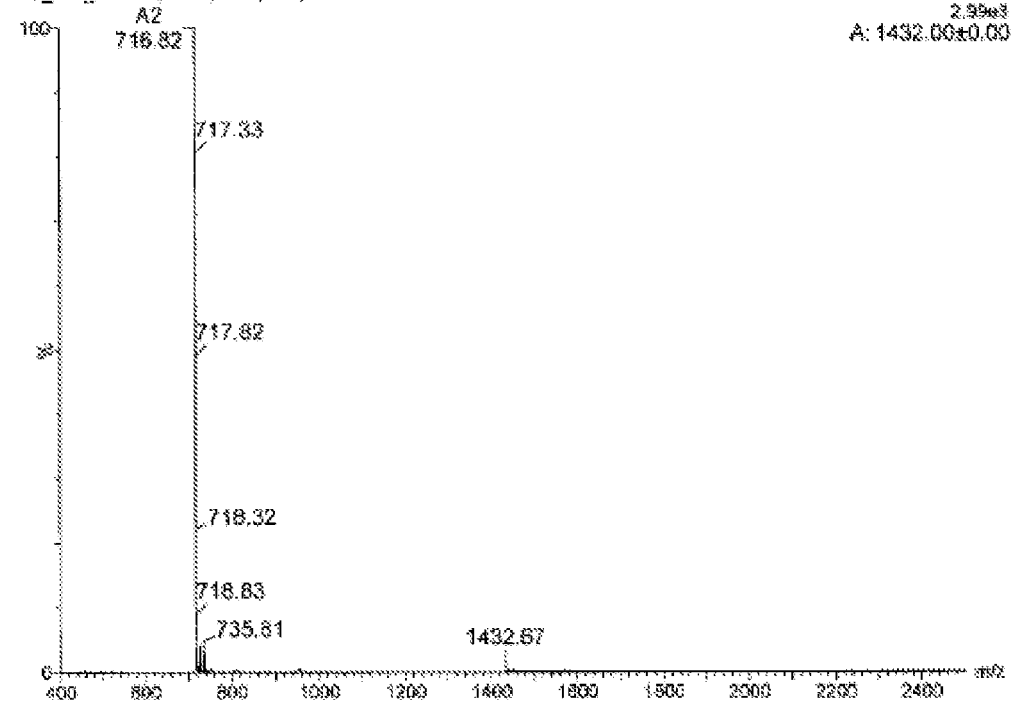
Fig. 7

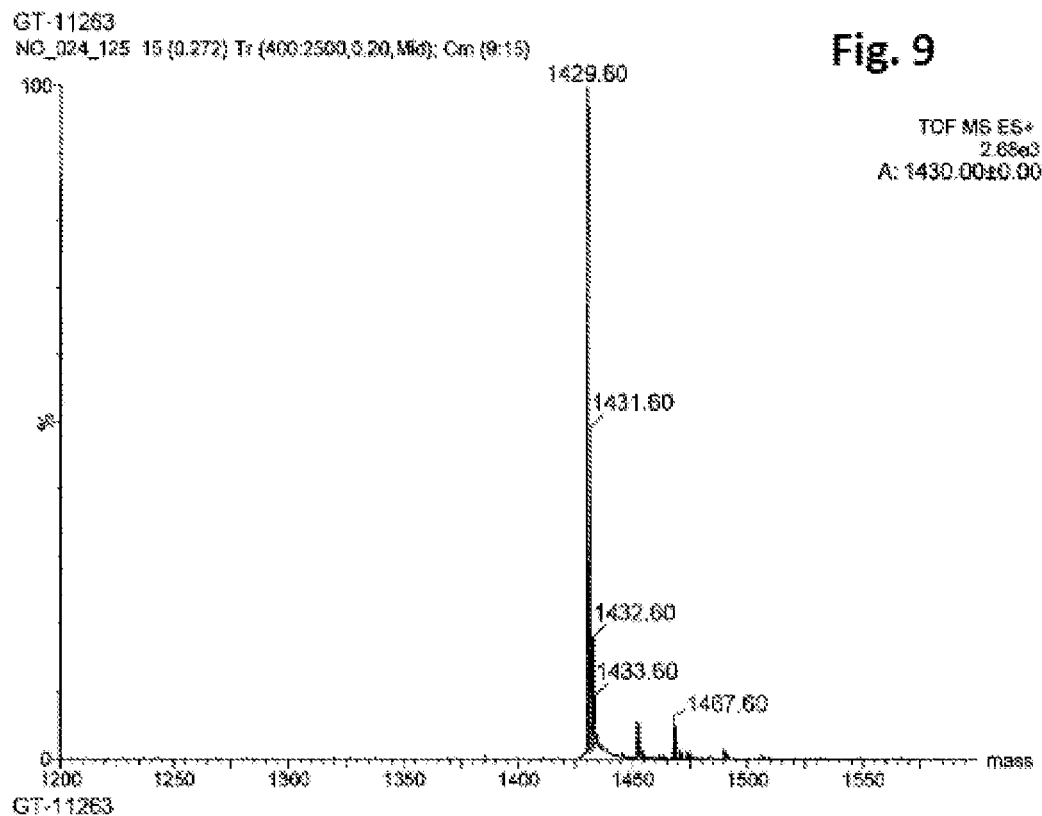
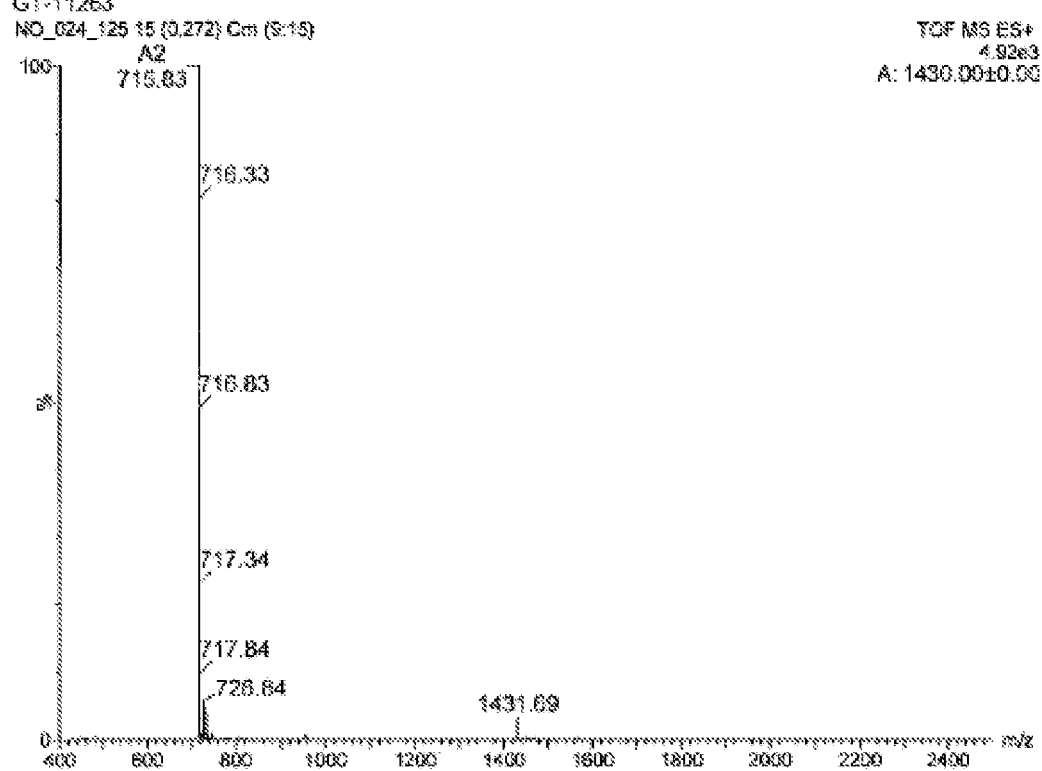
Fig. 9

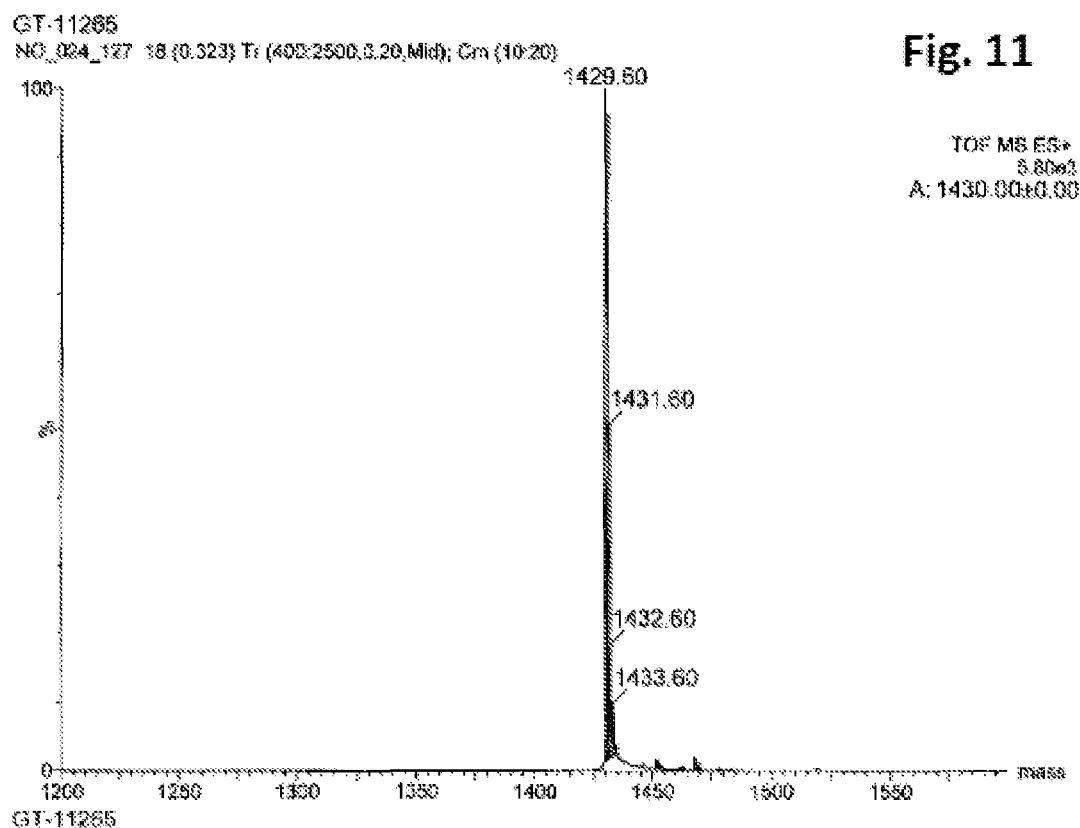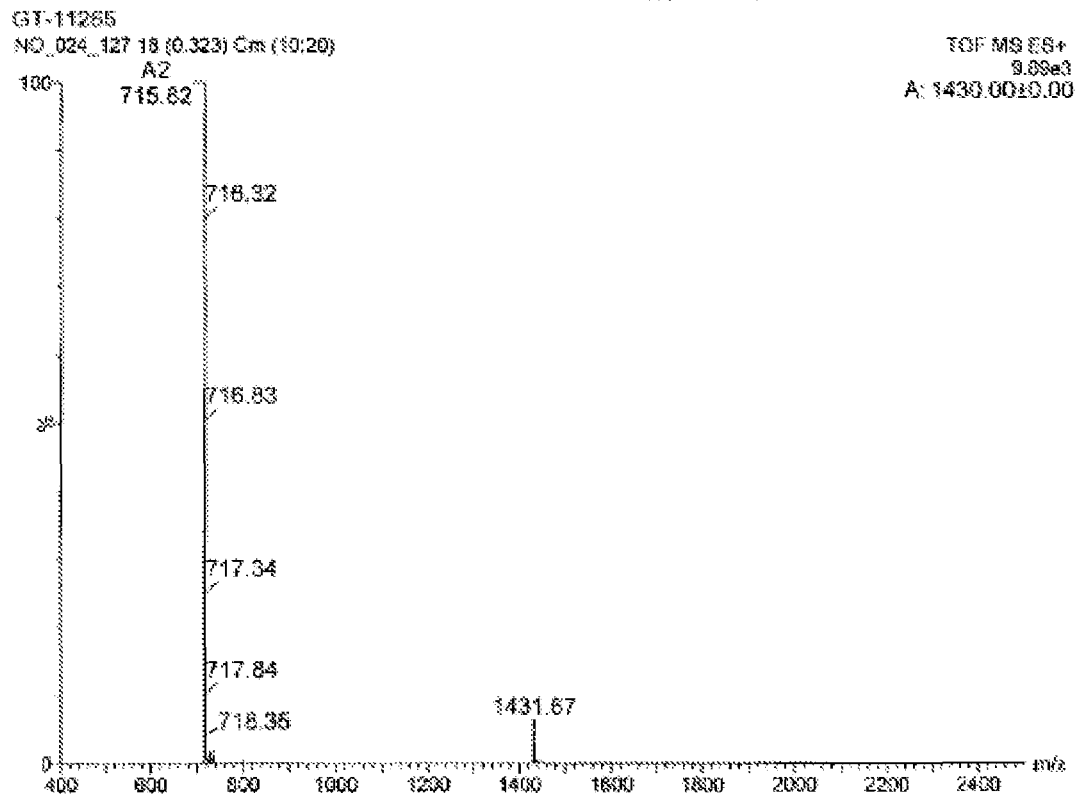
Fig. 11

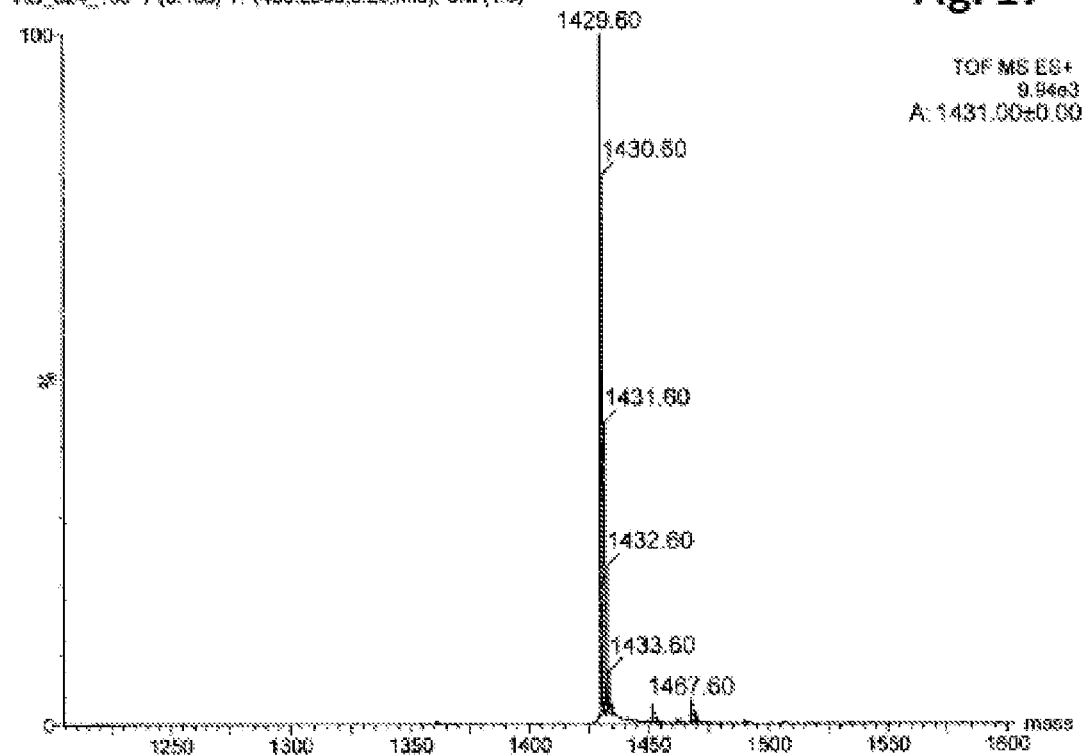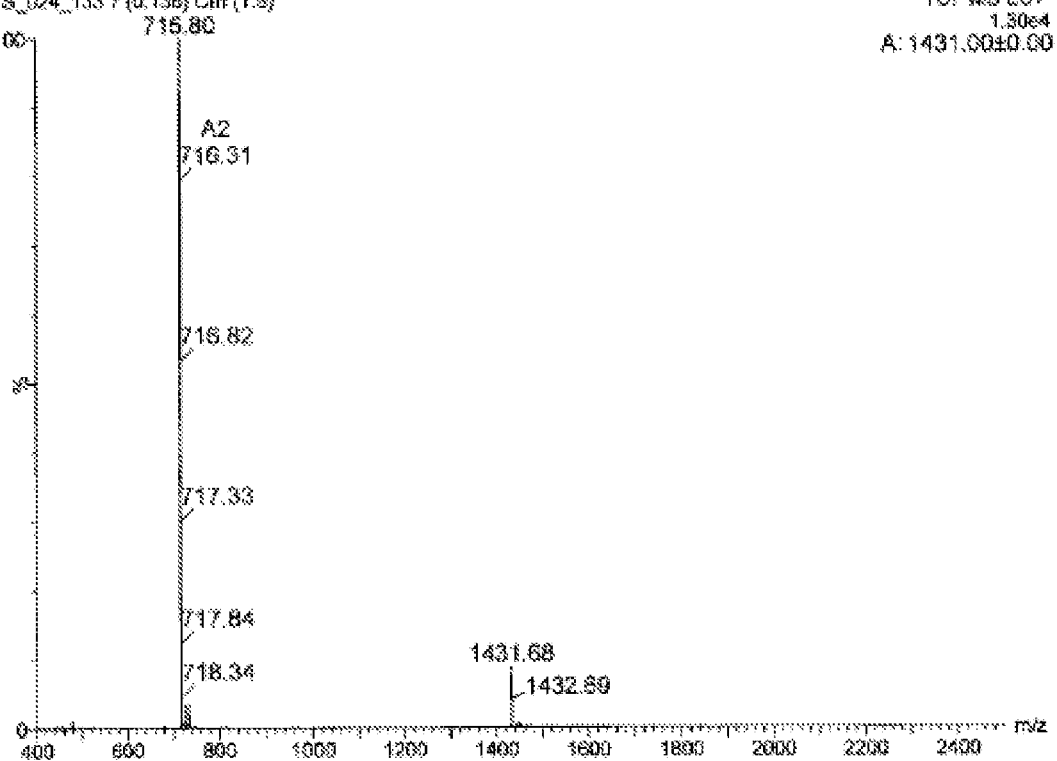
Fig. 17

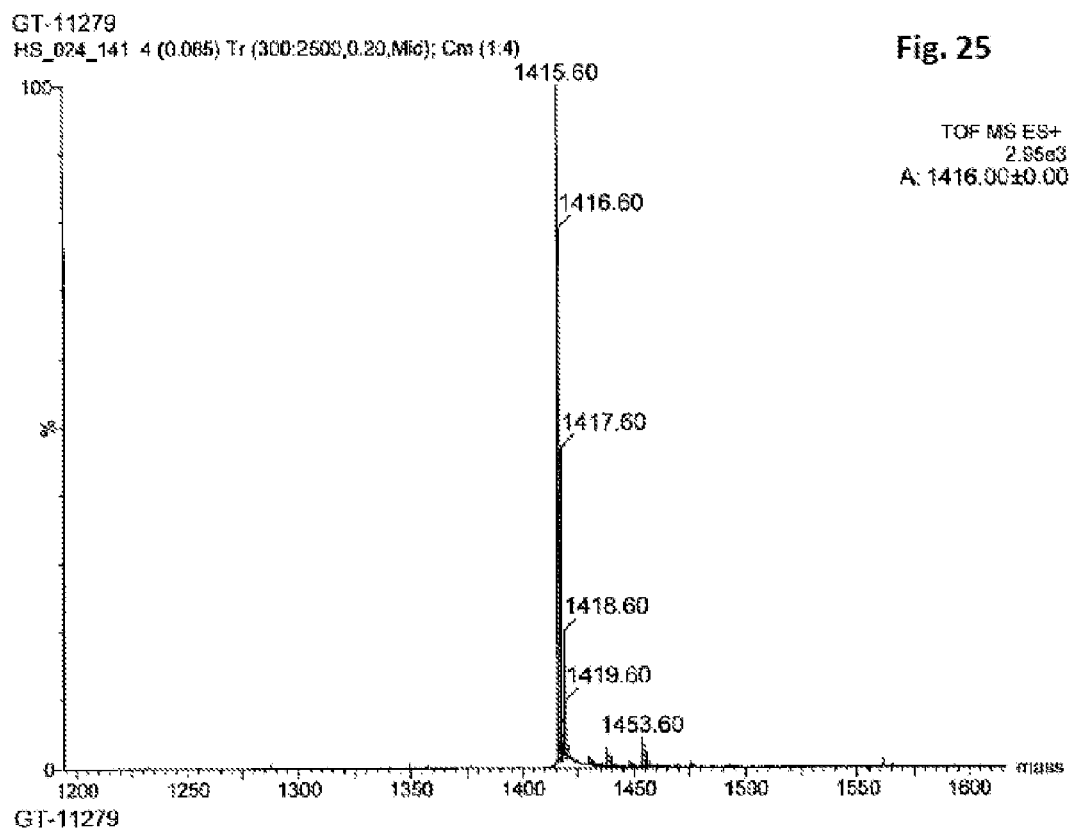
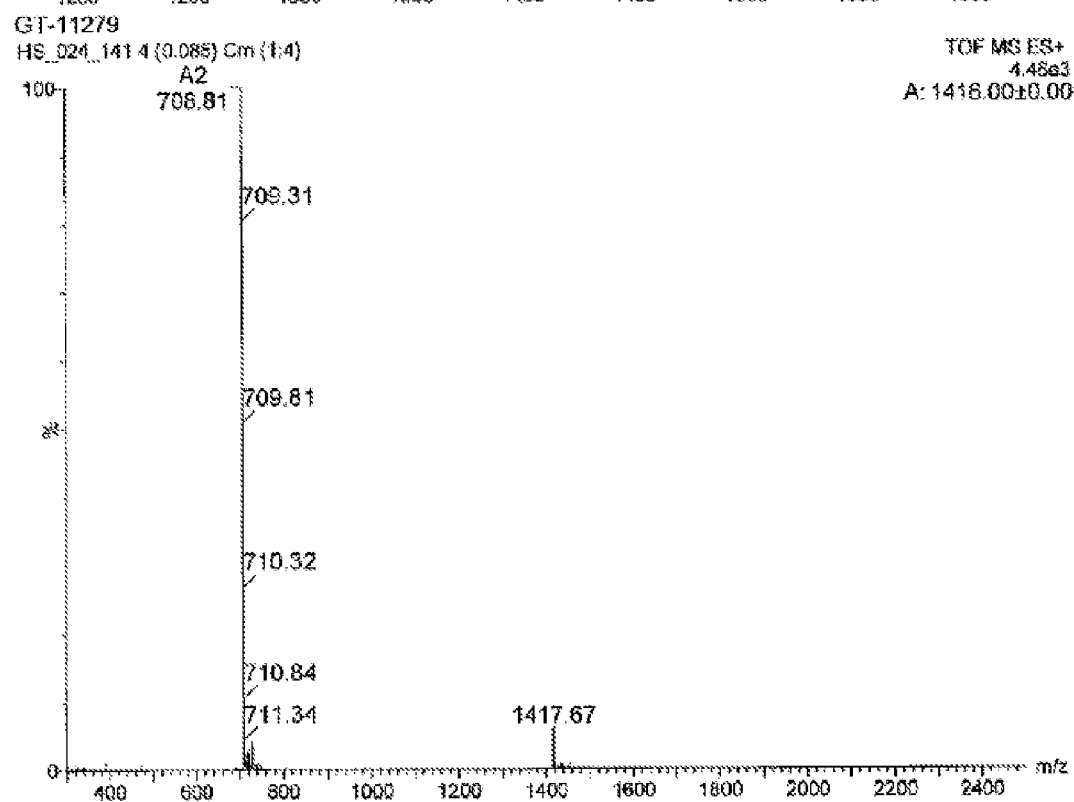
Fig. 25

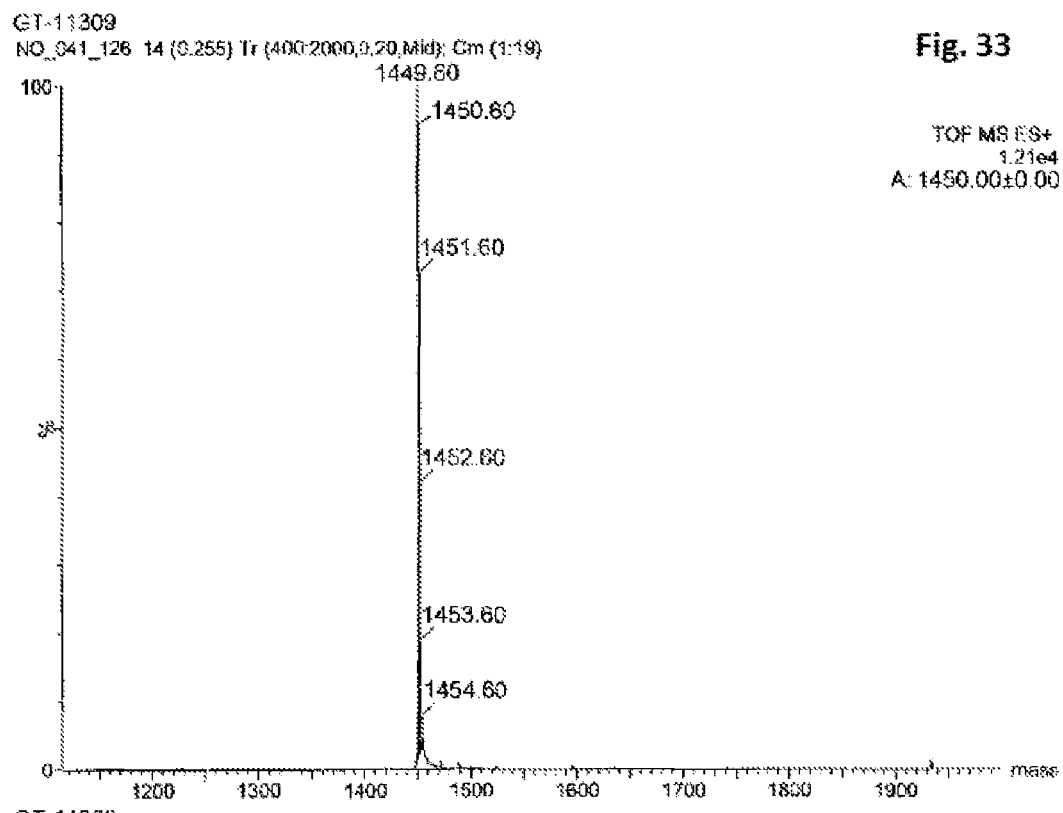
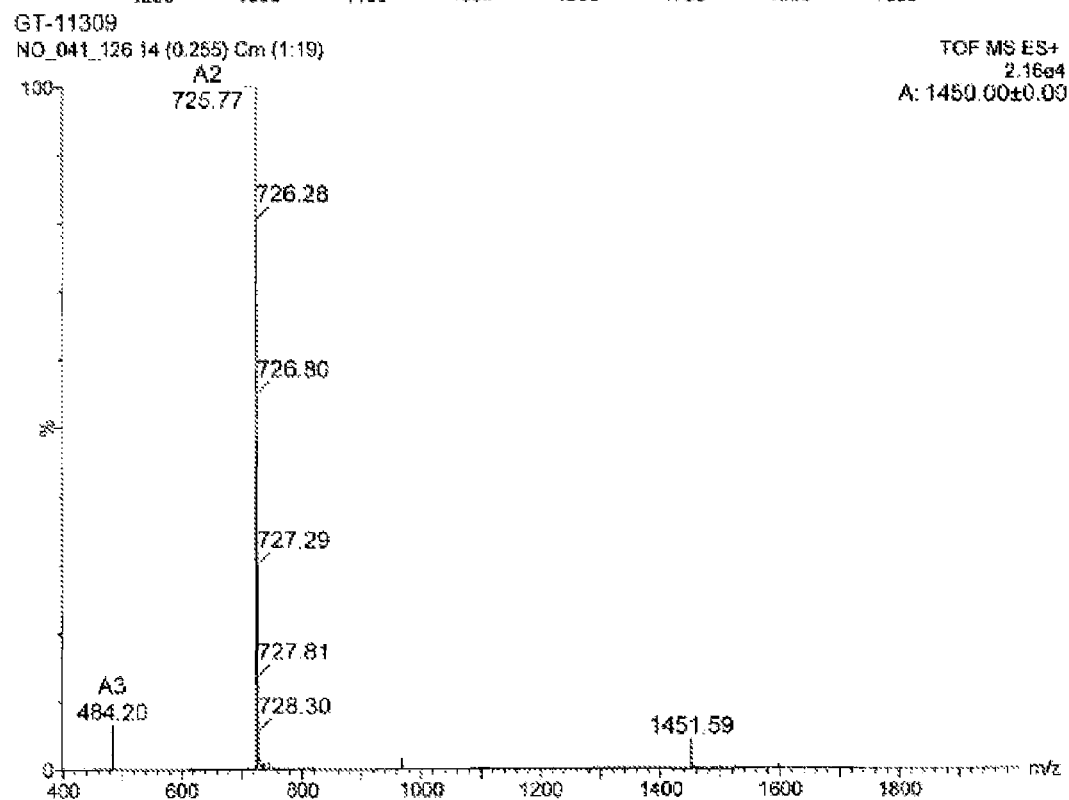
Fig. 33

Fig. 45
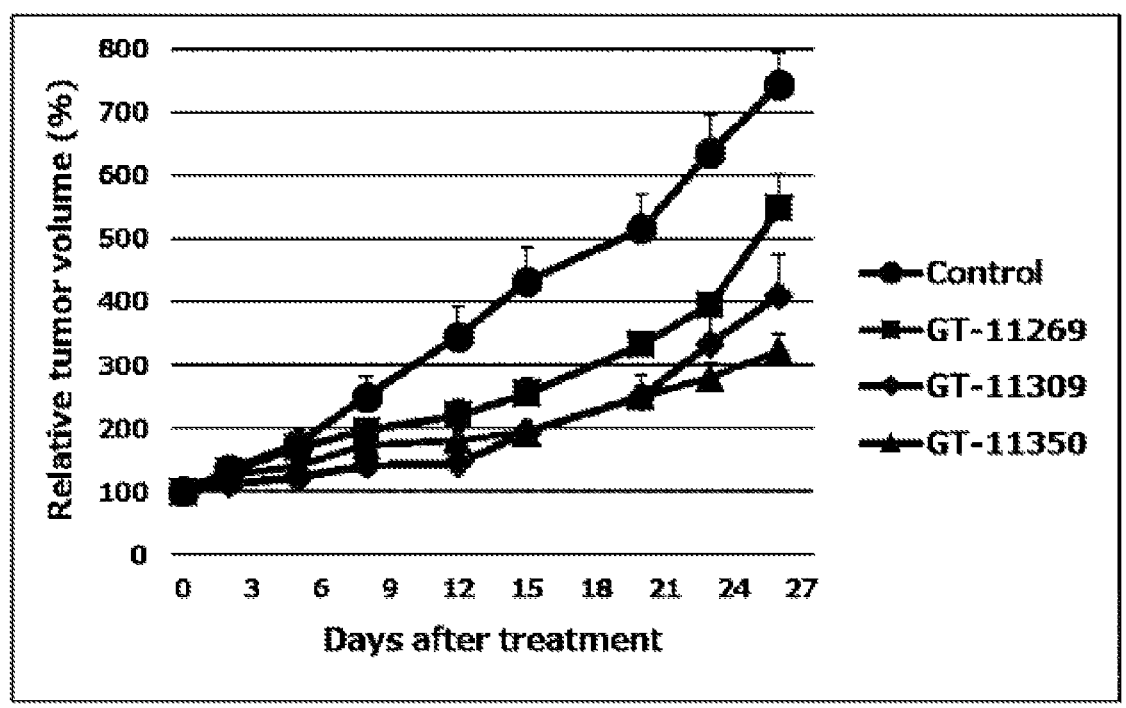
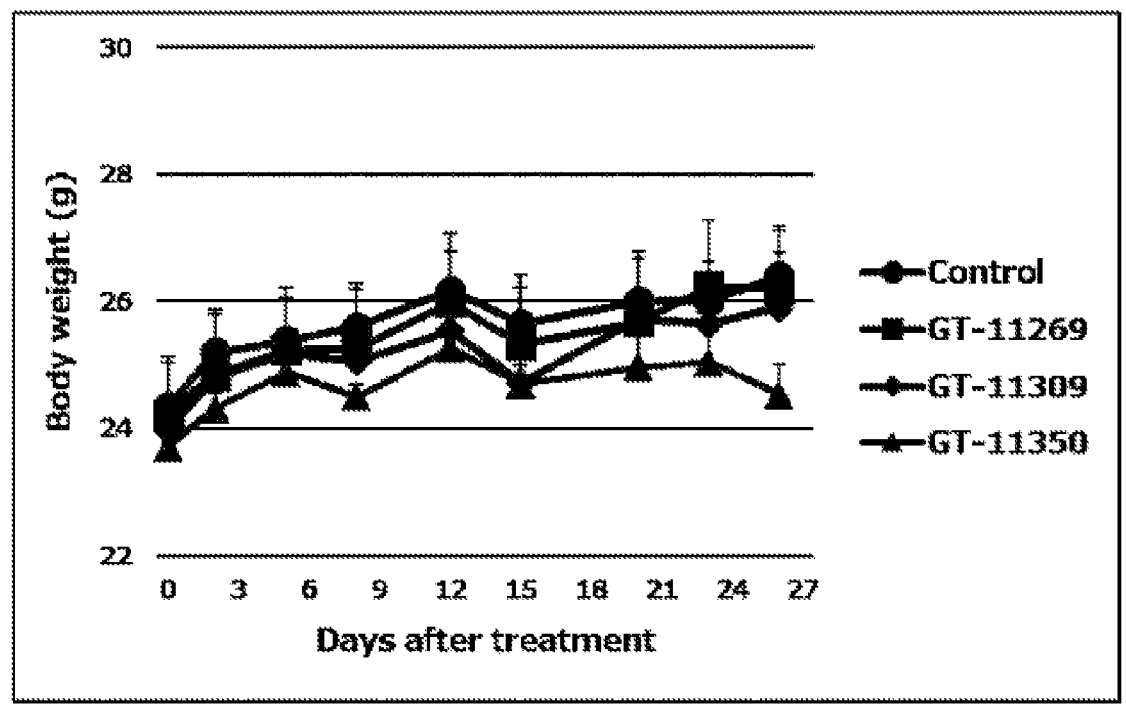

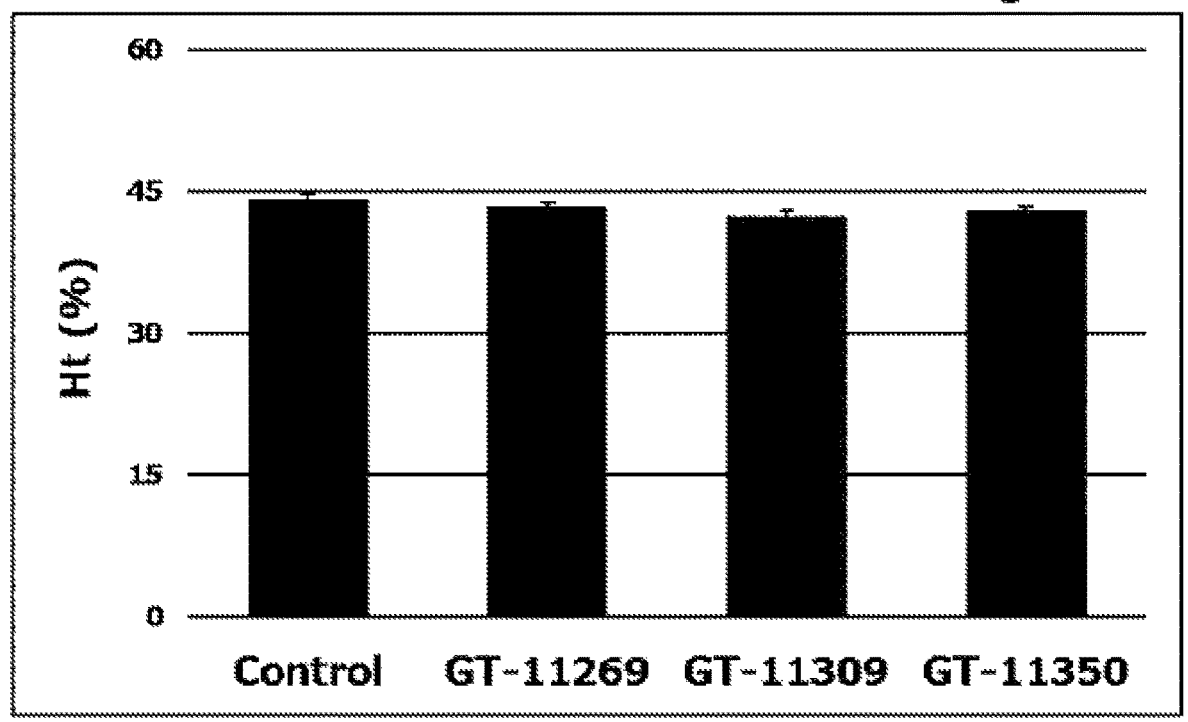
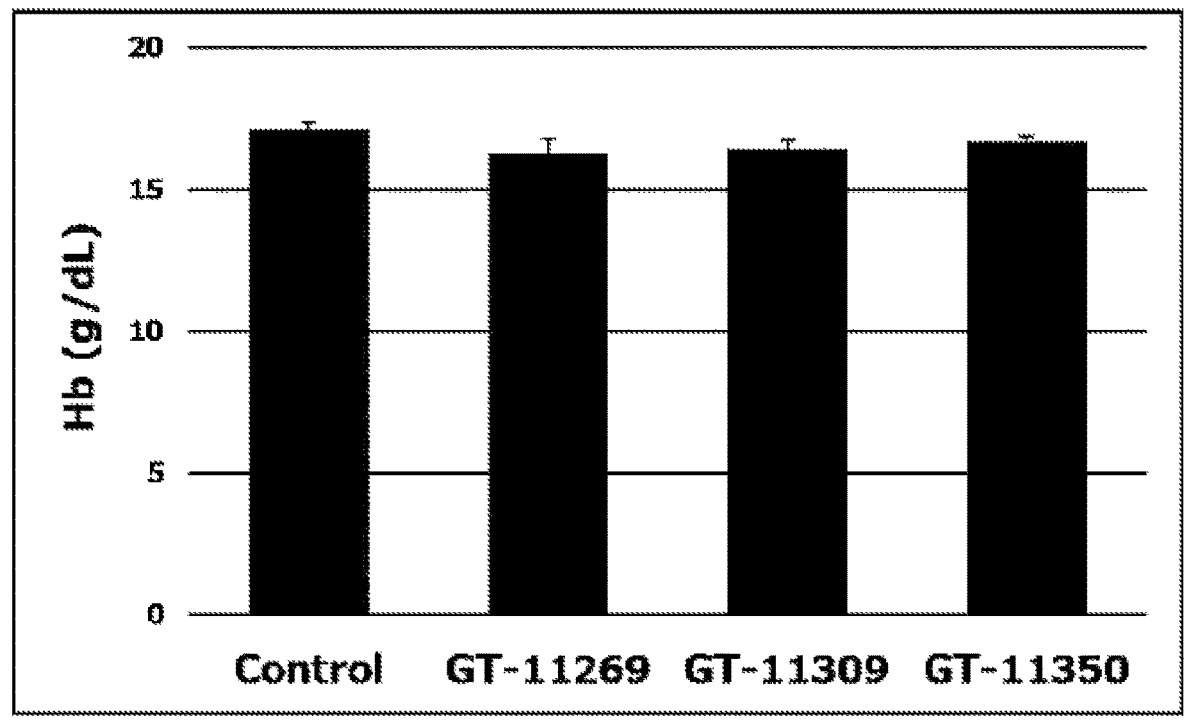
Fig. 47

Fig. 50
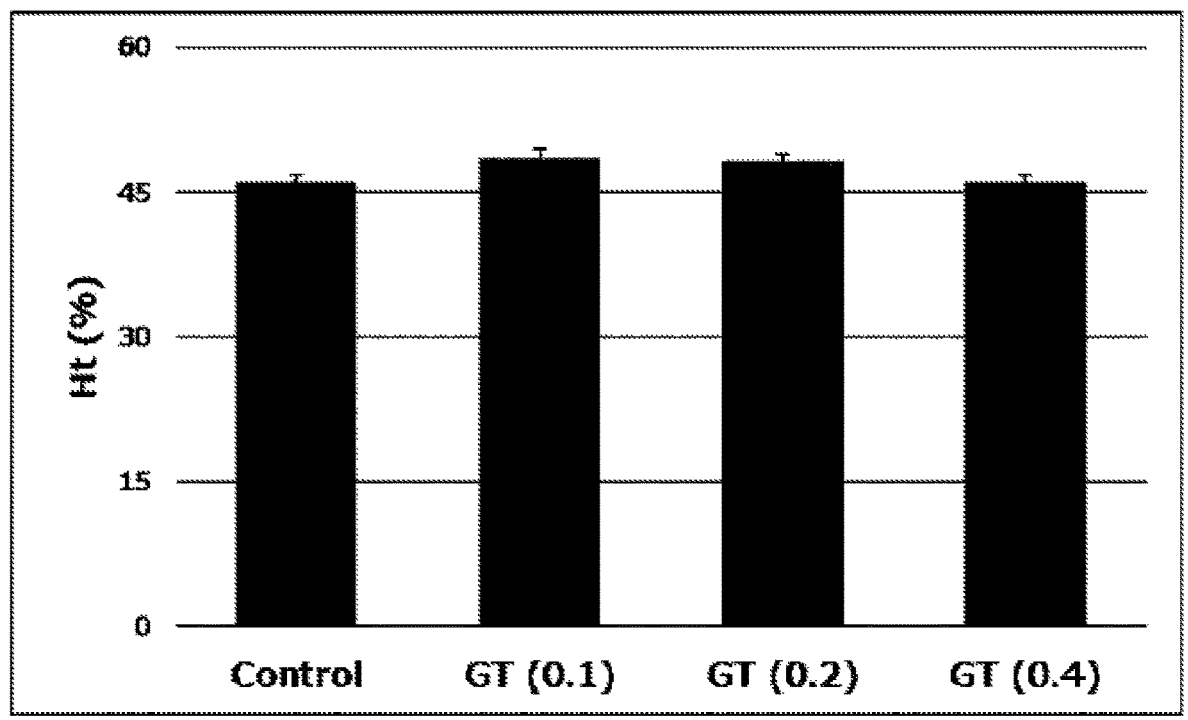
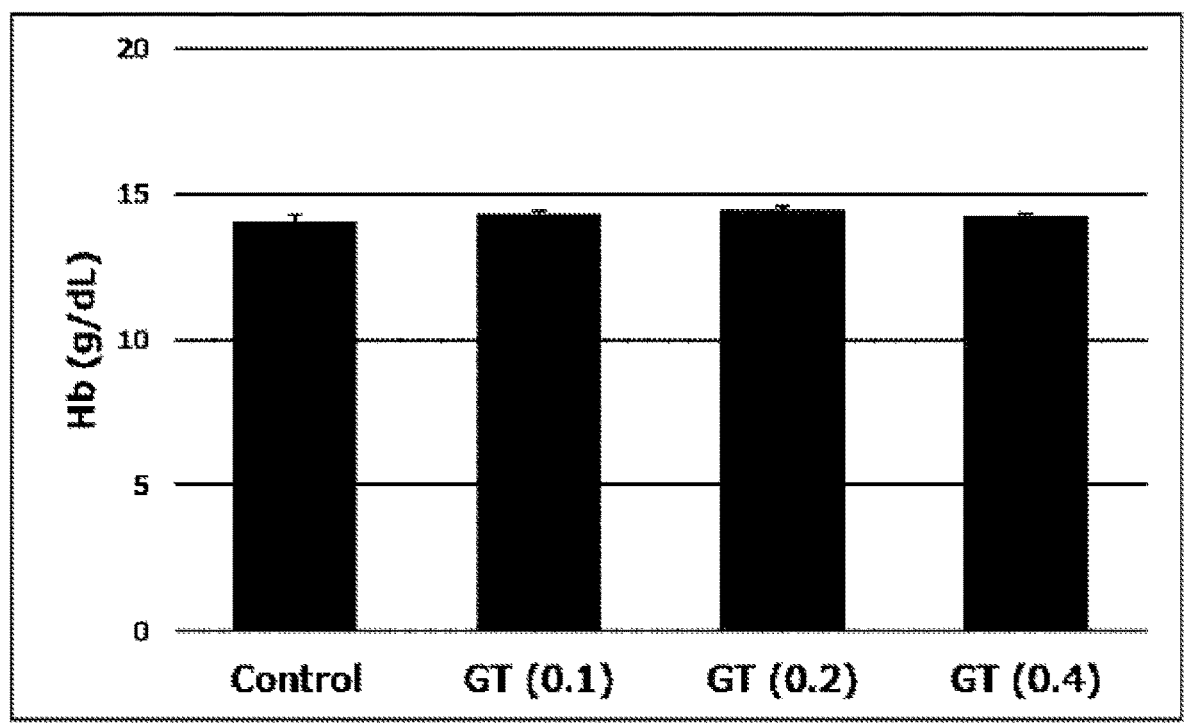

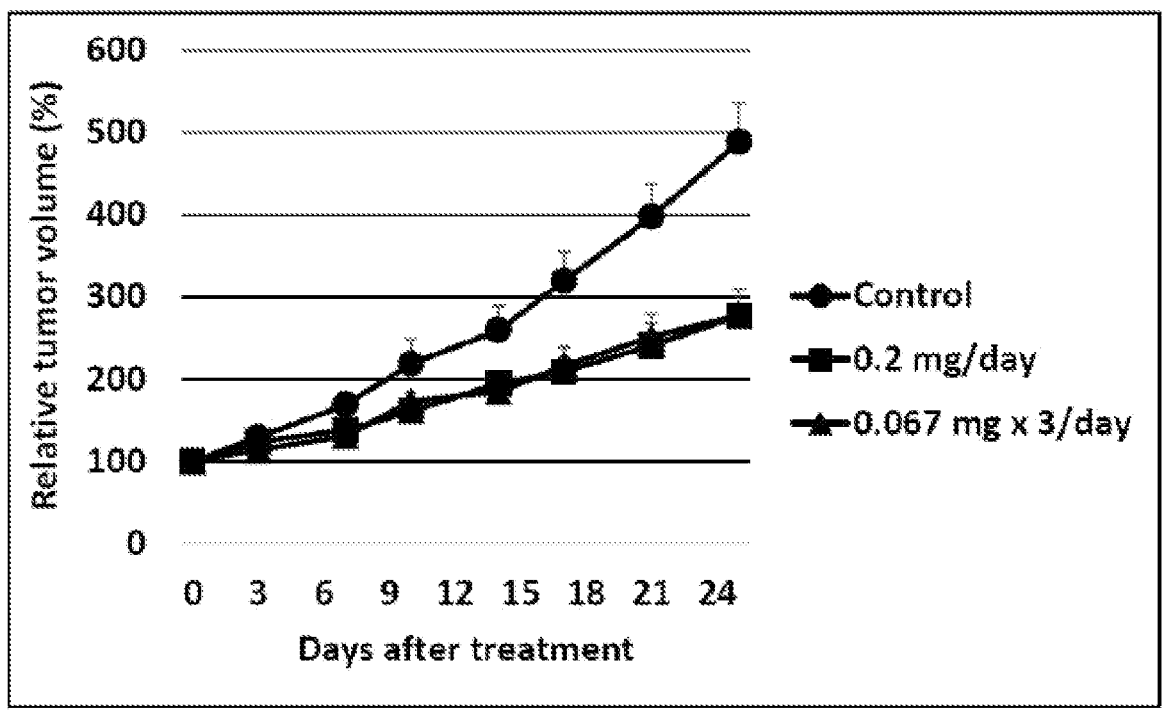
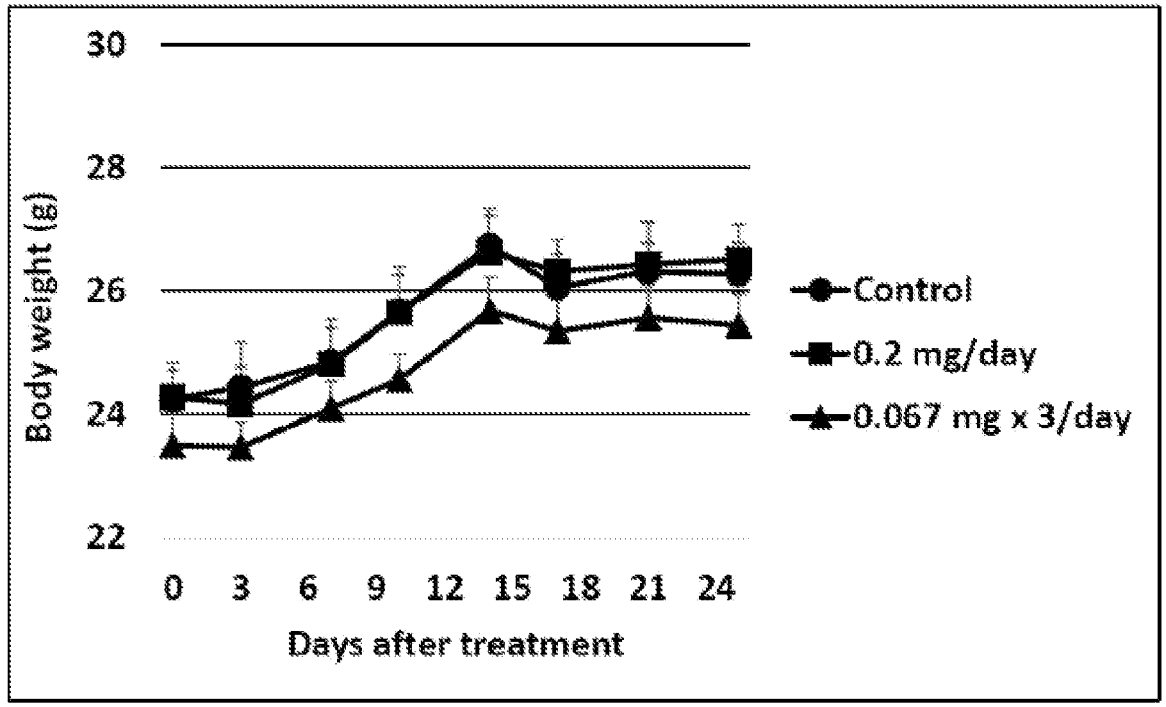
Fig. 51

SEQUENCE LISTING

```
<160> NUMBER OF SEQ ID NOS: 57

<210> SEQ ID NO 1
<211> LENGTH: 12
<212> TYPE: PRT
<213> ORGANISM: artificial sequence
<220> FEATURE:
<223> OTHER INFORMATION: mutant sequence
<220> FEATURE:
<221> NAME/KEY: misc_feature
<222> LOCATION: (4)..(9)
```

```
<223> OTHER INFORMATION: Xaa can be any of naturally occurring amino
      acid or modified amino acid
<220> FEATURE:
<221> NAME/KEY: misc_feature
<222> LOCATION: (11)..(12)
<223> OTHER INFORMATION: Xaa can be any of naturally occurring amino
      acid or modified amino acid

<400> SEQUENCE: 1

Ser Cys His Xaa Xaa Xaa Xaa Xaa Xaa Val Xaa Xaa
1               5                   10

<210> SEQ ID NO 2
<211> LENGTH: 12
<212> TYPE: PRT
<213> ORGANISM: Homo sapiens

<400> SEQUENCE: 2

Ser Cys His Phe Gly Pro Leu Thr Trp Val Cys Lys
1               5                   10

<210> SEQ ID NO 3
<211> LENGTH: 12
<212> TYPE: PRT
<213> ORGANISM: artificial sequence
<220> FEATURE:
<223> OTHER INFORMATION: mutant sequence

<400> SEQUENCE: 3

Ser Cys His Tyr Gly Pro Leu Thr Trp Val Cys Lys
1               5                   10

<210> SEQ ID NO 4
<211> LENGTH: 12
<212> TYPE: PRT
<213> ORGANISM: artificial sequence
<220> FEATURE:
<223> OTHER INFORMATION: mutant sequence

<400> SEQUENCE: 4

Ser Cys His Phe Ala Pro Leu Thr Trp Val Cys Lys
1               5                   10

<210> SEQ ID NO 5
<211> LENGTH: 12
<212> TYPE: PRT
<213> ORGANISM: artificial sequence
<220> FEATURE:
<223> OTHER INFORMATION: mutant sequence

<400> SEQUENCE: 5

Ser Cys His Phe Gly Ala Leu Thr Trp Val Cys Lys
1               5                   10

<210> SEQ ID NO 6
<211> LENGTH: 12
<212> TYPE: PRT
<213> ORGANISM: artificial sequence
<220> FEATURE:
<223> OTHER INFORMATION: mutant sequence

<400> SEQUENCE: 6

Ser Cys His Phe Gly Pro Ala Thr Trp Val Cys Lys
1               5                   10

<210> SEQ ID NO 7
<211> LENGTH: 12
```

```
<212> TYPE: PRT
<213> ORGANISM: artificial sequence
<220> FEATURE:
<223> OTHER INFORMATION: mutant sequence

<400> SEQUENCE: 7

Ser Cys His Phe Gly Pro Met Thr Trp Val Cys Lys
1               5                   10

<210> SEQ ID NO 8
<211> LENGTH: 12
<212> TYPE: PRT
<213> ORGANISM: artificial sequence
<220> FEATURE:
<223> OTHER INFORMATION: mutant sequence

<400> SEQUENCE: 8

Ser Cys His Phe Gly Pro Leu Thr Met Val Cys Lys
1               5                   10

<210> SEQ ID NO 9
<211> LENGTH: 12
<212> TYPE: PRT
<213> ORGANISM: artificial sequence
<220> FEATURE:
<223> OTHER INFORMATION: YS12
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 9

Ser Cys His Phe Gly Pro Leu Thr Trp Val Cys Lys
1               5                   10

<210> SEQ ID NO 10
<211> LENGTH: 12
<212> TYPE: PRT
<213> ORGANISM: artificial sequence
<220> FEATURE:
<223> OTHER INFORMATION: GT11261
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 10

Ser Cys His Tyr Gly Pro Leu Thr Trp Val Cys Lys
1               5                   10

<210> SEQ ID NO 11
<211> LENGTH: 12
<212> TYPE: PRT
<213> ORGANISM: artificial sequence
<220> FEATURE:
<223> OTHER INFORMATION: GT11264
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
```

```
<223> OTHER INFORMATION: AMIDATION

<400> SEQUENCE: 11

Ser Cys His Phe Ala Pro Leu Thr Trp Val Cys Lys
1               5                   10

<210> SEQ ID NO 12
<211> LENGTH: 12
<212> TYPE: PRT
<213> ORGANISM: artificial sequence
<220> FEATURE:
<223> OTHER INFORMATION: GT11266
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 12

Ser Cys His Phe Gly Ala Leu Thr Trp Val Cys Lys
1               5                   10

<210> SEQ ID NO 13
<211> LENGTH: 12
<212> TYPE: PRT
<213> ORGANISM: artificial sequence
<220> FEATURE:
<223> OTHER INFORMATION: GT11268
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 13

Ser Cys His Phe Gly Pro Ala Thr Trp Val Cys Lys
1               5                   10

<210> SEQ ID NO 14
<211> LENGTH: 12
<212> TYPE: PRT
<213> ORGANISM: artificial sequence
<220> FEATURE:
<223> OTHER INFORMATION: GT11269
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 14

Ser Cys His Phe Gly Pro Met Thr Trp Val Cys Lys
1               5                   10

<210> SEQ ID NO 15
<211> LENGTH: 12
<212> TYPE: PRT
<213> ORGANISM: artificial sequence
<220> FEATURE:
<223> OTHER INFORMATION: GT11270
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (12)..(12)
<223> OTHER INFORMATION: AMIDATION

<400> SEQUENCE: 15

Ser Cys His Phe Gly Pro Leu Thr Met Val Cys Lys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic sequence GT-11255
<220> FEATURE:
<221> NAME/KEY: MOD_RES
<222> LOCATION: 1
<223> OTHER INFORMATION: benzoyl
<220> FEATURE:
<221> NAME/KEY: AMIDATION
<222> LOCATION: 12

<400> SEQUENCE: 16

Ser Cys His Phe Gly Pro Leu Thr Trp Val Cys Lys
1               5                   10

<210> SEQ ID NO 17
<211> LENGTH: 12
<212> TYPE: PRT
<213> ORGANISM: GT-11256Artificial Sequence
<220> FEATURE:
<223> OTHER INFORMATION: Synthetic sequence GT-11256
<220> FEATURE:
<221> NAME/KEY: MOD_RES
<222> LOCATION: 1
<223> OTHER INFORMATION: p-fluorophenylacetyl
<220> FEATURE:
<221> NAME/KEY: AMIDATION
<222> LOCATION: 12

<400> SEQUENCE: 17

Ser Cys His Phe Gly Pro Leu Thr Trp Val Cys Lys
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic sequence GT-11257
<220> FEATURE:
<221> NAME/KEY: MOD_RES
<222> LOCATION: 1
<223> OTHER INFORMATION: propionyl
<220> FEATURE:
<221> NAME/KEY: AMIDATION
<222> LOCATION: 12

<400> SEQUENCE: 18

Ser Cys His Phe Gly Pro Leu Thr Trp Val Cys Lys
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic sequence GT-11258
```

```
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = p-fluoro-Phe
<220> FEATURE:
<221> NAME/KEY: AMIDATION
<222> LOCATION: 12

<400> SEQUENCE: 19

Ser Cys His Xaa Gly Pro Leu Thr Trp Val Cys Lys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic sequence GT-11259
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = p-chloro-Phe
<220> FEATURE:
<221> NAME/KEY: AMIDATION
<222> LOCATION: 12

<400> SEQUENCE: 20

Ser Cys His Xaa Gly Pro Leu Thr Trp Val Cys Lys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic sequence GT-11260
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = m-chloro-Phe
<220> FEATURE:
<221> NAME/KEY: AMIDATION
<222> LOCATION: 12

<400> SEQUENCE: 21

Ser Cys His Xaa Gly Pro Leu Thr Trp Val Cys Lys
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic sequence GT-11262
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = phenylglycine
<220> FEATURE:
<221> NAME/KEY: AMIDATION
<222> LOCATION: 12
```

```
<400> SEQUENCE: 22

Ser Cys His Xaa Gly Pro Leu Thr Trp Val Cys Lys
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic sequence GT-11263
<220> FEATURE:
<221> NAME/KEY: AMIDATION
<222> LOCATION: 1
<220> FEATURE:
<221> NAME/KEY: VARIANT
<222> LOCATION: 4
<223> OTHER INFORMATION: Xaa = phenethylglycine
<220> FEATURE:
<221> NAME/KEY: AMIDATION
<222> LOCATION: 12

<400> SEQUENCE: 23

Ser Cys His Xaa Gly Pro Leu Thr Trp Val Cys Lys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic sequence GT-11265
<220> FEATURE:
<221> NAME/KEY: ACETYLATION
<222> LOCATION: 1
<220> FEATURE:
<221> NAME/KEY: VARIANT
<222> LOCATION: 5
<223> OTHER INFORMATION: Xaa = a
<220> FEATURE:
<221> NAME/KEY: AMIDATION
<222> LOCATION: 12

<400> SEQUENCE: 24

Ser Cys His Phe Xaa Pro Leu Thr Trp Val Cys Lys
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic sequence GT-11267
<220> FEATURE:
<221> NAME/KEY: ACETYLATION
<222> LOCATION: 1
<220> FEATURE:
<221> NAME/KEY: VARIANT
<222> LOCATION: 6
<223> OTHER INFORMATION: Xaa = homoproline
<220> FEATURE:
<221> NAME/KEY: AMIDATION
<222> LOCATION: 12

<400> SEQUENCE: 25

Ser Cys His Phe Gly Xaa Leu Thr Trp Val Cys Lys
1               5                   10

<210> SEQ ID NO 26
<211> LENGTH: 12
<212> TYPE: PRT
```

```
<213> ORGANISM: Artificial Sequence
<220> FEATURE:
<223> OTHER INFORMATION: Synthetic sequence GT-11271
<220> FEATURE:
<221> NAME/KEY: ACETYLATION
<222> LOCATION: 1
<220> FEATURE:
<221> NAME/KEY: VARIANT
<222> LOCATION: 9
<223> OTHER INFORMATION: Xaa = beta-homotryptophan
<220> FEATURE:
<221> NAME/KEY: AMIDATION
<222> LOCATION: 12

<400> SEQUENCE: 26

Ser Cys His Phe Gly Pro Leu Thr Xaa Val Cys Lys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic sequence GT-11272
<220> FEATURE:
<221> NAME/KEY: ACETYLATION
<222> LOCATION: 1
<220> FEATURE:
<221> NAME/KEY: VARIANT
<222> LOCATION: 9
<223> OTHER INFORMATION: Xaa = alpha-naphthylalanine
<220> FEATURE:
<221> NAME/KEY: AMIDATION
<222> LOCATION: 12

<400> SEQUENCE: 27

Ser Cys His Phe Gly Pro Leu Thr Xaa Val Cys Lys
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic sequence GT-11273
<220> FEATURE:
<221> NAME/KEY: ACETYLATION
<222> LOCATION: 1
<220> FEATURE:
<221> NAME/KEY: VARIANT
<222> LOCATION: 9
<223> OTHER INFORMATION: Xaa = beta-naphthylalanine
<220> FEATURE:
<221> NAME/KEY: AMIDATION
<222> LOCATION: 12

<400> SEQUENCE: 28

Ser Cys His Phe Gly Pro Leu Thr Xaa Val Cys Lys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic sequence GT-11274
<220> FEATURE:
<221> NAME/KEY: ACETYLATION
<222> LOCATION: 1
<220> FEATURE:
<221> NAME/KEY: VARIANT
<222> LOCATION: 9
<223> OTHER INFORMATION: Xaa = 8-quinolylalanine
```

```
<220> FEATURE:
<221> NAME/KEY: AMIDATION
<222> LOCATION: 12

<400> SEQUENCE: 29

Ser Cys His Phe Gly Pro Leu Thr Xaa Val Cys Lys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic sequence GT-11275
<220> FEATURE:
<221> NAME/KEY: ACETYLATION
<222> LOCATION: 1
<220> FEATURE:
<221> NAME/KEY: VARIANT
<222> LOCATION: 9
<223> OTHER INFORMATION: Xaa = 6-chloro-Trp
<220> FEATURE:
<221> NAME/KEY: AMIDATION
<222> LOCATION: 12

<400> SEQUENCE: 30

Ser Cys His Phe Gly Pro Leu Thr Xaa Val Cys Lys
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic sequence GT-11276
<220> FEATURE:
<221> NAME/KEY: ACETYLATION
<222> LOCATION: 1
<220> FEATURE:
<221> NAME/KEY: VARIANT
<222> LOCATION: 9
<223> OTHER INFORMATION: Xaa = 5-chloro-Trp
<220> FEATURE:
<221> NAME/KEY: AMIDATION
<222> LOCATION: 12

<400> SEQUENCE: 31

Ser Cys His Phe Gly Pro Leu Thr Xaa Val Cys Lys
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic sequence GT-11277
<220> FEATURE:
<221> NAME/KEY: ACETYLATION
<222> LOCATION: 1
<220> FEATURE:
<221> NAME/KEY: VARIANT
<222> LOCATION: 11
<223> OTHER INFORMATION: Xaa = homocysteine
<220> FEATURE:
<221> NAME/KEY: AMIDATION
<222> LOCATION: 12

<400> SEQUENCE: 32

Ser Cys His Phe Gly Pro Leu Thr Trp Val Xaa Lys
1               5                   10
```

```
<210> SEQ ID NO 33
<211> LENGTH: 12
<212> TYPE: PRT
<213> ORGANISM: Artificial Sequence
<220> FEATURE:
<223> OTHER INFORMATION: Synthetic sequence GT-11278
<220> FEATURE:
<221> NAME/KEY: ACETYLATION
<222> LOCATION: 1
<220> FEATURE:
<221> NAME/KEY: VARIANT
<222> LOCATION: 11
<223> OTHER INFORMATION: Xaa = penicillamine
<220> FEATURE:
<221> NAME/KEY: AMIDATION
<222> LOCATION: 12

<400> SEQUENCE: 33

Ser Cys His Phe Gly Pro Leu Thr Trp Val Xaa Lys
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic sequence GT-11279
<220> FEATURE:
<221> NAME/KEY: ACETYLATION
<222> LOCATION: 1
<220> FEATURE:
<221> NAME/KEY: AMIDATION
<222> LOCATION: 12

<400> SEQUENCE: 34

Lys Cys Val Trp Thr Leu Pro Gly Phe His Cys Ser
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic sequence GT-11280
<220> FEATURE:
<221> NAME/KEY: ACETYLATION
<222> LOCATION: 1
<220> FEATURE:
<221> NAME/KEY: AMIDATION
<222> LOCATION: 12

<400> SEQUENCE: 35

Lys Cys Val Trp Thr Leu Gly Gly Phe His Cys Ser
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic sequence GT-11303
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = 3,4-difluoro-Phe
<220> FEATURE:
<221> NAME/KEY: VARIANT
<222> LOCATION: 9
<223> OTHER INFORMATION: Xaa = 8-quinolylalanine
<220> FEATURE:
```

```
<221> NAME/KEY: AMIDATION
<222> LOCATION: 12

<400> SEQUENCE: 36

Ser Cys His Xaa Gly Pro Leu Thr Xaa Val Cys Lys
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic sequence GT-11304
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = 3,4-difluoro-Phe
<220> FEATURE:
<221> NAME/KEY: VARIANT
<222> LOCATION: 9
<223> OTHER INFORMATION: Xaa = 2-quinolylalanine
<220> FEATURE:
<221> NAME/KEY: AMIDATION
<222> LOCATION: 12

<400> SEQUENCE: 37

Ser Cys His Xaa Gly Pro Leu Thr Xaa Val Cys Lys
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic sequence GT-11305
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = 3,4-difluoro-Phe
<220> FEATURE:
<221> NAME/KEY: VARIANT
<222> LOCATION: 9
<223> OTHER INFORMATION: Xaa = 2-benzothiazolylalanine
<220> FEATURE:
<221> NAME/KEY: AMIDATION
<222> LOCATION: 12

<400> SEQUENCE: 38

Ser Cys His Xaa Gly Pro Leu Thr Xaa Val Cys Lys
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic sequence GT-11306
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = p-fluoro-Phe
<220> FEATURE:
<221> NAME/KEY: VARIANT
<222> LOCATION: 9
```

<223> OTHER INFORMATION: Xaa = 2-quinolylalanine
<220> FEATURE:
<221> NAME/KEY: AMIDATION
<222> LOCATION: 12

<400> SEQUENCE: 39

Ser Cys His Xaa Gly Pro Leu Thr Xaa Val Cys Lys
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic sequence GT-11307
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = p-fluoro-Phe
<220> FEATURE:
<221> NAME/KEY: VARIANT
<222> LOCATION: 9
<223> OTHER INFORMATION: Xaa = 2-benzothiazolylalanine
<220> FEATURE:
<221> NAME/KEY: AMIDATION
<222> LOCATION: 12

<400> SEQUENCE: 40

Ser Cys His Xaa Gly Pro Leu Thr Xaa Val Cys Lys
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic sequence GT-11308
<220> FEATURE:
<221> NAME/KEY: ACETYLATION
<222> LOCATION: 1
<220> FEATURE:
<221> NAME/KEY: VARIANT
<222> LOCATION: 9
<223> OTHER INFORMATION: Xaa = 2-quinolylalanine
<220> FEATURE:
<221> NAME/KEY: AMIDATION
<222> LOCATION: 12

<400> SEQUENCE: 41

Ser Cys His Tyr Gly Pro Leu Thr Xaa Val Cys Lys
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic sequence GT-1309
<220> FEATURE:
<221> NAME/KEY: ACETYLATION
<222> LOCATION: 1
<220> FEATURE:
<221> NAME/KEY: VARIANT
<222> LOCATION: 9
<223> OTHER INFORMATION: Xaa = 2-benzothiazolylalanine
<220> FEATURE:
<221> NAME/KEY: AMIDATION
<222> LOCATION: 12

<400> SEQUENCE: 42

```
Ser Cys His Tyr Gly Pro Leu Thr Xaa Val Cys Lys
1               5                   10
```

<210> SEQ ID NO 43
<211> LENGTH: 5
<212> TYPE: PRT
<213> ORGANISM: Artificial Sequence
<220> FEATURE:
<223> OTHER INFORMATION: Reprentative peptide

<400> SEQUENCE: 43

```
Ala Gly Thr Cys Ile
1               5
```

<210> SEQ ID NO 44
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = 3,4-difluoro-Phe
<220> FEATURE:
<221> NAME/KEY: AMIDATION
<222> LOCATION: 12

<400> SEQUENCE: 44

```
Ser Cys His Xaa Gly Pro Leu Thr Trp Val Cys Lys
1               5                   10
```

<210> SEQ ID NO 45
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: ACETYLATION
<222> LOCATION: 1
<220> FEATURE:
<221> NAME/KEY: VARIANT
<222> LOCATION: 9
<223> OTHER INFORMATION: Xaa = 2-quinolylalanine
<220> FEATURE:
<221> NAME/KEY: AMIDATION
<222> LOCATION: 12

<400> SEQUENCE: 45

```
Ser Cys His Phe Gly Pro Leu Thr Xaa Val Cys Lys
1               5                   10
```

<210> SEQ ID NO 46
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: ACETYLATION
<222> LOCATION: 1
<220> FEATURE:
<221> NAME/KEY: VARIANT
<222> LOCATION: 9
<223> OTHER INFORMATION: Xaa = 2-benzothiazolylalanine
<220> FEATURE:
<221> NAME/KEY: AMIDATION

```
<222> LOCATION: 12

<400> SEQUENCE: 46

Ser Cys His Phe Gly Pro Leu Thr Xaa Val Cys Lys
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = p-fluoro-Phe
<220> FEATURE:
<221> NAME/KEY: VARIANT
<222> LOCATION: 9
<223> OTHER INFORMATION: Xaa = 8-quinolylalanine
<220> FEATURE:
<221> NAME/KEY: AMIDATION
<222> LOCATION: 12

<400> SEQUENCE: 47

Ser Cys His Xaa Gly Pro Leu Thr Xaa Val Cys Lys
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: ACETYLATION
<222> LOCATION: 1
<220> FEATURE:
<221> NAME/KEY: VARIANT
<222> LOCATION: 9
<223> OTHER INFORMATION: Xaa = 8-quinolylalanine
<220> FEATURE:
<221> NAME/KEY: AMIDATION
<222> LOCATION: 12

<400> SEQUENCE: 48

Ser Cys His Tyr Gly Pro Leu Thr Xaa Val Cys Lys
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = 4-pyridylalanine
<220> FEATURE:
<221> NAME/KEY: AMIDATION
<222> LOCATION: 12

<400> SEQUENCE: 49

Ser Cys His Xaa Gly Pro Leu Thr Trp Val Cys Lys
1               5                   10
```

```
<210> SEQ ID NO 50
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = 3-pyridylalanine
<220> FEATURE:
<221> NAME/KEY: AMIDATION
<222> LOCATION: 12

<400> SEQUENCE: 50

Ser Cys His Xaa Gly Pro Leu Thr Trp Val Cys Lys
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = p-methoxy-Phe
<220> FEATURE:
<221> NAME/KEY: AMIDATION
<222> LOCATION: 12

<400> SEQUENCE: 51

Ser Cys His Xaa Gly Pro Leu Thr Trp Val Cys Lys
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = m-methoxy-Phe
<220> FEATURE:
<221> NAME/KEY: AMIDATION
<222> LOCATION: 12

<400> SEQUENCE: 52

Ser Cys His Xaa Gly Pro Leu Thr Trp Val Cys Lys
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: ACETYLATION
```

```
<222> LOCATION: 1
<220> FEATURE:
<221> NAME/KEY: VARIANT
<222> LOCATION: 4
<223> OTHER INFORMATION: Xaa = m-hydroxy-Phe
<220> FEATURE:
<221> NAME/KEY: AMIDATION
<222> LOCATION: 12

<400> SEQUENCE: 53

Ser Cys His Xaa Gly Pro Leu Thr Trp Val Cys Lys
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = 1-naphthylalanine
<220> FEATURE:
<221> NAME/KEY: AMIDATION
<222> LOCATION: 12

<400> SEQUENCE: 54

Ser Cys His Xaa Gly Pro Leu Thr Trp Val Cys Lys
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = 2-naphthylalanine
<220> FEATURE:
<221> NAME/KEY: AMIDATION
<222> LOCATION: 12

<400> SEQUENCE: 55

Ser Cys His Xaa Gly Pro Leu Thr Trp Val Cys Lys
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: ACETYLATION
<222> LOCATION: 1
<220> FEATURE:
<221> NAME/KEY: VARIANT
<222> LOCATION: 9
<223> OTHER INFORMATION: Xaa = 3-benzothiazolylalanine
<220> FEATURE:
<221> NAME/KEY: AMIDATION
<222> LOCATION: 12

<400> SEQUENCE: 56
```

```
Ser Cys His Phe Gly Pro Leu Thr Xaa Val Cys Lys
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: ACETYLATION
<222> LOCATION: 1
<220> FEATURE:
<221> NAME/KEY: VARIANT
<222> LOCATION: 9
<223> OTHER INFORMATION: Xaa = 2-benzothiazolylalanine
<220> FEATURE:
<221> NAME/KEY: AMIDATION
<222> LOCATION: 12

<400> SEQUENCE: 57

Ser Cys His Tyr Gly Pro Met Thr Xaa Val Cys Lys
1               5                   10
```

ANTI-ERYTHROPOIETIN RECEPTOR PEPTIDE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 310245_401USPC_SEQUENCE_LISTING.txt. The text file is 19.1 KB, was created on Mar. 6, 2021, and is being submitted electronically via EFS-Web.

TECHNICAL FIELD

The present disclosure relates to a novel anti-erythropoietin receptor (hereinafter, also referred to as "EpoR") peptide, a composition comprising the same, and use thereof.

BACKGROUND ART

Erythropoietin is involved in differentiation and proliferation of red blood cells. Unlike other cytokines, erythropoietin is not produced in hemocytes, but is produced in the kidney or liver and released into the blood. It is understood that erythropoietin acts on burst-forming unit-erythroid (BFU-E) and colony-forming unit-erythroid (CFU-E) among red blood cell progenitor cells and promotes the differentiation and proliferation thereof to induce the production of red blood cells (Krantz S. B., Blood, Vol. 77, pp 419-434 (1991)). It is understood that when erythropoietin binds to an erythropoietin receptor that is present on the cellular membrane of a progenitor cell, a signal is transmitted into the cellular nucleus, inducing differentiation of red blood cells, i.e., intracellular accumulation of globin mRNA, production of hemoglobin, and proliferation of red blood cells (D'Andrea A. D. et al., Cell, Vol. 57, pp 277-285 (1989)). However, the detailed mechanism thereof is still not elucidated, with many that need to be resolved in the future.

An embryo immediately after implantation (Yasuda Y. et al., Develop. Growth Differ., Vol. 35, pp 711-722 (1993)), human, monkey, and mouse brain (Marti H. H. et al., Eur. J. NeuroSci., Vol. 8, pp 666-676 (1996)), and mouse uterus (Yasuda Y. et al., J. Biol. Chem., Vol. 273, pp 25381-25387 (1998)) are known as sites where erythropoietin gene is expressed in tissue other than sites associated with erythroblasts.

Erythropoietin can act by binding to an erythropoietin receptor.

CITATION LIST

Non Patent Literature

[NPL 1] Krantz S. B., Blood, Vol. 77, pp 419-434 (1991)

[NPL 2] D'Andrea A. D. et al., Cell, Vol. 57, pp 277-285 (1989)

[NPL 3] Yasuda Y. et al., Develop. Growth Differ., Vol. 35, pp 711-722 (1993)

[NPL 4] Marti H. H. et al., Eur. J. NeuroSci., Vol. 8, pp 666-676 (1996)

[NPL 5] Yasuda Y. et al., J. Biol. Chem., Vol. 273, pp 25381-25387 (1998)

SUMMARY OF INVENTION

Solution to Problem

The present disclosure provides the peptide or a salt or solvate thereof, or a prodrug thereof, of the present disclosure described in detail hereinafter. In one embodiment, the present disclosure provides a composition, a formulation, or a kit comprising the same. In another embodiment, the present disclosure provides use of the peptide or a salt or solvate thereof, or a prodrug thereof, of the present disclosure, or a method for the use. In a specific embodiment, the peptide, or a salt or solvate thereof, or a prodrug thereof, of the present disclosure has one or more characteristics from improvement in efficacy such as potent EpoR inhibiting capability, high cancer cell killing capability, low normal cell killing capability, cancer cell killing capability at a low dosing frequency or the like, reduction in side effects, ability to specifically migrate to a specific site, improved absorption/distribution/metabolism/excretion kinetics, improvement of bioavailability, and high stability. In one embodiment, the peptide, or a salt or solvate thereof, or a prodrug thereof, of the present disclosure, can be used in the treatment or prevention/prophylaxis of a proliferative disease, adenomyosis, or diabetic retinopathy.

Therefore, the present disclosure provides the following.

(Item 1)

A modified peptide based on a peptide with a structure of -[SCHFGPLTWVCK]-(SEQ ID NO: 2), having at least one characteristic improved from a peptide with a structure of $CH_3$—CO-SCHFGPLTWVCK-$NH_2$ (SEQ ID NO: 9), or a prodrug thereof or a salt thereof (an alphabet indicates a one letter code of an amino acid).

(Item 2)

A modified peptide with a structure of formula (I):

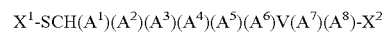

wherein:
X$^1$ is an amino terminus side of the peptide, and X$^2$ is a carboxy terminus side of the peptide;
A$^1$ is —NH—CH(R$^{41}$)—CO—, wherein R$^{41}$ has a structure of (a bond, or a linear or branched alkylene group)-(an aryl group or a heteroaryl group optionally substituted with a substituent selected from the group consisting of a linear or branched alkyl group optionally substituted with a halogen atom, a linear or branched methoxyl group optionally substituted with a halogen atom, a halogen atom, and a hydroxyl group);
A$^2$ is Ala, D-alanine, or Gly;
A$^3$ is Pro, homoproline, or Ala;
A$^4$ is Met, Leu, Ala, or Ile;
A$^5$ is Thr or Ala;
A$^6$ is —NH—CH(R$^{41}$)—CO—, wherein R$^{41}$ has a structure of (a bond, or a linear or branched alkylene group)-(an aryl group or a heteroaryl group optionally substituted with a substituent selected from the group consisting of a linear or branched alkyl group optionally substituted with a halogen atom, a linear or branched methoxyl group optionally substituted with a halogen atom, a halogen atom, and a hydroxyl group);

A⁷ is Cys, homocysteine, or penicillamine;
A⁸ is Lys, Arg, or absent;
two sulfur atoms in the peptide may form a disulfide bond;
X¹ is hydrogen, a peptide consisting of any 1 to 3 amino acids, or —C(=O) R¹;
X² is hydrogen, a peptide consisting of any 1 to 3 amino acids, or —NR¹₂;
each R¹ is independently selected from the group consisting of hydrogen, a hydroxyl group, a linear or branched $C_{1\sim10}$ alkyl group optionally substituted with R², a linear or branched $C_{1\sim10}$ alkenyl group optionally substituted with R², a linear or branched $C_{1\sim10}$ alkynyl group optionally substituted with R², an aromatic or non-aromatic 5- to 10-membered ring optionally substituted with R², —OR², and —NR²₂, or two R¹ attached to the same atom together form an aromatic or non-aromatic 5- to 10-membered ring optionally substituted with R²; and
each R² is independently selected from the group consisting of hydrogen, a hydroxyl group, halogen, a benzyl group optionally substituted with halogen or a hydroxyl group, —CH₃, —CH₂CH₃, —CH₂CH₂CH₃, —NH₂, —NHCH₃, —N(CH₃)₂, =O, —COOH, —OCH₃, and —OCH₂CH₃; or
with a structure of formula (II):

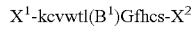

X¹-kcvwtl(B¹)Gfhcs-X² wherein:
X¹ is an amino terminus side of the peptide, and X² is a carboxy terminus side of the peptide;
B¹ is Gly or D-proline, k, c, v, w, t, l, G, f, h, c, and s each indicate an amino acid, an upper case letter indicates an L form or no enantiomer, and a lower case letter indicates a D form;
two sulfur atoms in the peptide may form a disulfide bond;
X¹ is hydrogen, a peptide consisting of any 1 to 3 amino acids, or —C(=O) R¹;
X² is hydrogen, a peptide consisting of any 1 to 3 amino acids, or —NR¹₂;
each R¹ is independently selected from the group consisting of hydrogen, a hydroxyl group, a linear or branched $C_{1\sim10}$ alkyl group optionally substituted with R², a linear or branched $C_{1\sim10}$ alkenyl group optionally substituted with R², a linear or branched $C_{1\sim10}$ alkynyl group optionally substituted with R², an aromatic or non-aromatic 5- to 10-membered ring optionally substituted with R², —OR², and —NR²₂, or two R¹ attached to the same atom together form an aromatic or non-aromatic 5- to 10-membered ring optionally substituted with R²; and
each R² is independently selected from the group consisting of hydrogen, a hydroxyl group, halogen, a benzyl group optionally substituted with halogen or a hydroxyl group, —CH₃, —CH₂CH₃, —CH₂CH₂CH₃, —NH₂, —NHCH₃, —N(CH₃)₂, =O, —COOH, —OCH₃, and —OCH₂CH₃;
or a prodrug thereof or a salt thereof.
(Item 3)
The modified peptide or the prodrug thereof or the salt thereof of item 2, satisfying at least one of the following conditions:
A² is Gly;
A³ is Phe;
A⁵ is Thr;
A⁷ is Cys; and
A⁸ is Lys.

(Item 4)
The modified peptide or the prodrug thereof or the salt thereof of item 2 or 3, wherein A¹ is Tyr, p-fluorophenylalanine, or phenethylglycine.
(Item 5)
The modified peptide or the prodrug thereof or the salt thereof of item 2 or 3, wherein A¹ is Tyr.
(Item 6)
The modified peptide or the prodrug thereof or the salt thereof of any one of items 2 to 5, wherein A⁴ is Leu or Met.
(Item 7)
The modified peptide or the prodrug thereof or the salt thereof of any one of items 2 to 5, wherein A⁴ is Met.
(Item 8)
The modified peptide or the prodrug thereof or the salt thereof of any one of items 2 to 7, wherein A⁶ is Trp, Met, 8-naphthylalanine, 2-quinolylalanine, 5-chloro-Trp, or 2-benzothiazolylalanine.
(Item 9)
The modified peptide or the prodrug thereof or the salt thereof of any one of items 2 to 7, wherein A⁶ is 2-benzothiazolylalanine.
(Item 10)
The modified peptide or the prodrug thereof or the salt thereof of any one of items 2 to 9, wherein:
A² is Gly;
A³ is Phe;
A⁵ is Thr;
A⁷ is Cys; and
A⁸ is Lys.
(Item 11)
The modified peptide or the prodrug thereof or the salt thereof of any one of items 2 to 10, wherein X¹ is —COOH, a benzoyl group, a propionyl group, or a p-fluorophenylacetyl group.
(Item 12)
The modified peptide or the prodrug thereof or the salt thereof of any one of items 2 to 11, wherein X² is NH₂.
(Item 13)
A composition comprising the modified peptide or the prodrug thereof or the salt thereof of any one of items 1 to 12 for treating or preventing a proliferative disease (e.g., adenomyosis) or diabetic retinopathy.
(Item 14)
The composition of item 13, wherein the proliferative disease is adenomyosis, breast cancer, prostate cancer, pancreatic cancer, gastric cancer, lung cancer, large intestinal cancer (colon cancer, rectal cancer, or anal cancer), esophageal cancer, duodenal cancer, head and neck cancer (tongue cancer, pharyngeal cancer, or laryngeal cancer), brain tumor, schwannoma, neuroblastoma, glioma, non-small cell lung cancer, small cell lung cancer, liver cancer, kidney cancer, bile duct cancer, uterine cancer (endometrial cancer or cervical cancer), ovarian cancer, bladder cancer, skin cancer, hemangioma, malignant lymphoma, malignant melanoma, thyroid cancer, bone tumor, angiofibroma, retinal sarcoma, penile cancer, pediatric solid tumor, Kaposi's sarcoma, AIDS-related Kaposi's sarcoma, maxillary sinus tumor, fibrous histiocytoma, leiomyosarcoma, rhabdomyosarcoma, liposarcoma, uterine fibroid, osteoblastoma, osteosarcoma, chondrosarcoma, cancerous mesothelioma, or leukemia.
(Item 15)
The composition of item 13, wherein the proliferative disease is breast cancer, pancreatic cancer, liver cancer, malignant lymphoma, or leukemia.

(Item 16)

The modified peptide or the prodrug thereof or the salt thereof of any one of items 1 to 12 for treating or preventing a proliferative disease (e.g., adenomyosis) or diabetic retinopathy.

(Item 17)

The modified peptide or the prodrug thereof or the salt thereof of item 16, wherein the proliferative disease is adenomyosis, breast cancer, prostate cancer, pancreatic cancer, gastric cancer, lung cancer, large intestinal cancer (colon cancer, rectal cancer, or anal cancer), esophageal cancer, duodenal cancer, head and neck cancer (tongue cancer, pharyngeal cancer, or laryngeal cancer), brain tumor, schwannoma, neuroblastoma, glioma, non-small cell lung cancer, small cell lung cancer, liver cancer, kidney cancer, bile duct cancer, uterine cancer (endometrial cancer or cervical cancer), ovarian cancer, bladder cancer, skin cancer, hemangioma, malignant lymphoma, malignant melanoma, thyroid cancer, bone tumor, angiofibroma, retinal sarcoma, penile cancer, pediatric solid tumor, Kaposi's sarcoma, AIDS-related Kaposi's sarcoma, maxillary sinus tumor, fibrous histiocytoma, leiomyosarcoma, rhabdomyosarcoma, liposarcoma, uterine fibroid, osteoblastoma, osteosarcoma, chondrosarcoma, cancerous mesothelioma, or leukemia.

(Item 18)

The modified peptide or the prodrug thereof or the salt thereof of item 16, wherein the proliferative disease is breast cancer, pancreatic cancer, liver cancer, malignant lymphoma, or leukemia.

(Item 19)

A method for treating or preventing a proliferative disease (e.g., adenomyosis) or diabetic retinopathy in a subject, comprising administering to the subject an effective amount of the modified peptide or the prodrug thereof or the salt thereof of any one of items 1 to 12.

(Item 20)

The method of item 19, wherein the proliferative disease is adenomyosis, breast cancer, prostate cancer, pancreatic cancer, gastric cancer, lung cancer, large intestinal cancer (colon cancer, rectal cancer, or anal cancer), esophageal cancer, duodenal cancer, head and neck cancer (tongue cancer, pharyngeal cancer, or laryngeal cancer), brain tumor, schwannoma, neuroblastoma, glioma, non-small cell lung cancer, small cell lung cancer, liver cancer, kidney cancer, bile duct cancer, uterine cancer (endometrial cancer or cervical cancer), ovarian cancer, bladder cancer, skin cancer, hemangioma, malignant lymphoma, malignant melanoma, thyroid cancer, bone tumor, angiofibroma, retinal sarcoma, penile cancer, pediatric solid tumor, Kaposi's sarcoma, AIDS-related Kaposi's sarcoma, maxillary sinus tumor, fibrous histiocytoma, leiomyosarcoma, rhabdomyosarcoma, liposarcoma, uterine fibroid, osteoblastoma, osteosarcoma, chondrosarcoma, cancerous mesothelioma, or leukemia.

(Item 21)

The method of item 19, wherein the proliferative disease is breast cancer, pancreatic cancer, liver cancer, malignant lymphoma, or leukemia.

(Item 22)

Use of the modified peptide or the prodrug thereof or the salt thereof of any one of items 1 to 12 in the manufacture of a medicament for treating or preventing a proliferative disease (e.g., adenomyosis) or diabetic retinopathy.

(Item 23)

The use of item 22, wherein the proliferative disease is adenomyosis, breast cancer, prostate cancer, pancreatic cancer, gastric cancer, lung cancer, large intestinal cancer (colon cancer, rectal cancer, or anal cancer), esophageal cancer, duodenal cancer, head and neck cancer (tongue cancer, pharyngeal cancer, or laryngeal cancer), brain tumor, schwannoma, neuroblastoma, glioma, non-small cell lung cancer, small cell lung cancer, liver cancer, kidney cancer, bile duct cancer, uterine cancer (endometrial cancer or cervical cancer), ovarian cancer, bladder cancer, skin cancer, hemangioma, malignant lymphoma, malignant melanoma, thyroid cancer, bone tumor, angiofibroma, retinal sarcoma, penile cancer, pediatric solid tumor, Kaposi's sarcoma, AIDS-related Kaposi's sarcoma, maxillary sinus tumor, fibrous histiocytoma, leiomyosarcoma, rhabdomyosarcoma, liposarcoma, uterine fibroid, osteoblastoma, osteosarcoma, chondrosarcoma, cancerous mesothelioma, or leukemia.

(Item 24)

The use of item 22, wherein the proliferative disease is breast cancer, pancreatic cancer, liver cancer, malignant lymphoma, or leukemia.

The present disclosure is intended so that one or more of the features described above can be provided not only as the explicitly disclosed combinations, but also as other combinations. Additional embodiments and advantages of the present disclosure are recognized by those skilled in the art by reading and understanding the following detailed description as needed.

Advantageous Effects of Invention

The peptide of the present disclosure can have one or more advantageous characteristics from improvement in efficacy such as potent EpoR inhibiting capability, high cancer cell killing capability, low normal cell killing capability, cancer cell killing capability at a low dosing frequency or the like, reduction in side effects, ability to specifically migrate to a specific site, improved absorption/distribution/metabolism/excretion kinetics, improvement of bioavailability, and high stability. For example, a proliferative disease, adenomyosis, or diabetic retinopathy can be treated or prevented by providing a peptide with such a characteristic.

BRIEF DESCRIPTION OF DRAWINGS

FIG. 1 shows results of mass spectrometry on a synthetic peptide (benzoyl)-SCHFGPLTWVCK-NH$_2$ (SEQ ID NO: 16) (GT-11255). The top row shows the deconvolution values from ESI-MS measurement values, and the bottom row shows ESI-MS measurement values.

FIG. 2 shows results of mass spectrometry on a synthetic peptide (p-fluorophenylacetyl) -SCHFGPLTWVCK-NH$_2$ (SEQ ID NO: 17) (GT-11256). The top row shows the deconvolution values from ESI-MS measurement values, and the bottom row shows ESI-MS measurement values.

FIG. 7 shows results of mass spectrometry on a synthetic peptide Ac-SCHYGPLTWVCK-NH$_2$ (GT-11261) (SEQ ID NO: 10). The top row shows the deconvolution values from ESI-MS measurement values, and the bottom row shows ESI-MS measurement values.

FIG. 9 shows results of mass spectrometry on a synthetic peptide Ac-SCH(phenethylglycine)GPLTWVCK-NH$_2$ (SEQ ID NO: 23) (GT-11263). The top row shows the deconvolution values from ESI-MS measurement values, and the bottom row shows ESI-MS measurement values.

FIG. 11 shows results of mass spectrometry on a synthetic peptide Ac-SCHFaPLTWVCK-NH$_2$ (SEQ ID NO: 24) (GT-11265). The top row shows the deconvolution values from ESI-MS measurement values, and the bottom row shows ESI-MS measurement values.

FIG. 17 shows results of mass spectrometry on a synthetic peptide Ac-SCHFGPLT (P-homotryptophan)VCK-NH$_2$ (SEQ ID NO: 26) (GT-11271). The top row shows the deconvolution values from ESI-MS measurement values, and the bottom row shows ESI-MS measurement values.

FIG. 25 shows results of mass spectrometry on a synthetic peptide Ac-kcvwtlpGfhcs-NH$_2$ (SEQ ID NO: 34) (GT-11279). The top row shows the deconvolution values from ESI-MS measurement values, and the bottom row shows ESI-MS measurement values.

FIG. 33 shows results of mass spectrometry on a synthetic peptide Ac-SCHYGPLT(2-benzothiazolylalanine)VCK-NH$_2$ (SEQ ID NO: 42) (GT-1309). The top row shows the deconvolution values from ESI-MS measurement values, and the bottom row shows ESI-MS measurement values.

FIG. 45 shows results of evaluating the effect of synthetic peptides on human pancreatic cancer derived AsPC-1 cancer-bearing mice. In the top panel, the vertical axis indicates the relative tumor volume at each time when assuming the tumor volume as of the start of the test as 100%. The horizontal axis indicates the number of days elapsed from the administration starting date. In the bottom panel, the vertical axis indicates the body weight at each time, and the horizontal axis indicates the number of days elapsed from the administration starting date. The control is saline administration. The results are indicated as mean±standard error for 4 to 5 mice.

FIG. 47 shows results of evaluating the effect of synthetic peptides on human pancreatic cancer derived AsPC-1 cancer-bearing mice. The vertical axis indicates the hematocrit value (top panel) and blood hemoglobin concentration (bottom panel), and the horizontal axis indicates the test compounds. The results are indicated as mean±standard error for 3 to 5 mice.

FIG. 50 shows results of evaluating the effect of GT-11350 on human pancreatic cancer derived AsPC-1 cancer-bearing mice. The vertical axis indicates the hematocrit value (top panel) and blood hemoglobin concentration (bottom panel), and the horizontal axis indicates the test compounds. The results are indicated as mean±standard error for 6 mice.

FIG. 51 shows results of evaluating the effect of GT-11350 at three times daily or once daily on human pancreatic cancer derived AsPC-1 cancer-bearing mice. In the top panel, the vertical axis indicates the relative tumor volume at each time when assuming the tumor volume as of the start of the test as 100%. The horizontal axis indicates the number of days elapsed from the administration starting date. In the bottom panel, the vertical axis indicates the body weight at each time, and the horizontal axis indicates the number of days elapsed from the administration starting date. The control is saline administration. The results are indicated as mean±standard error for 6 mice.

DESCRIPTION OF EMBODIMENTS

Figure 3:
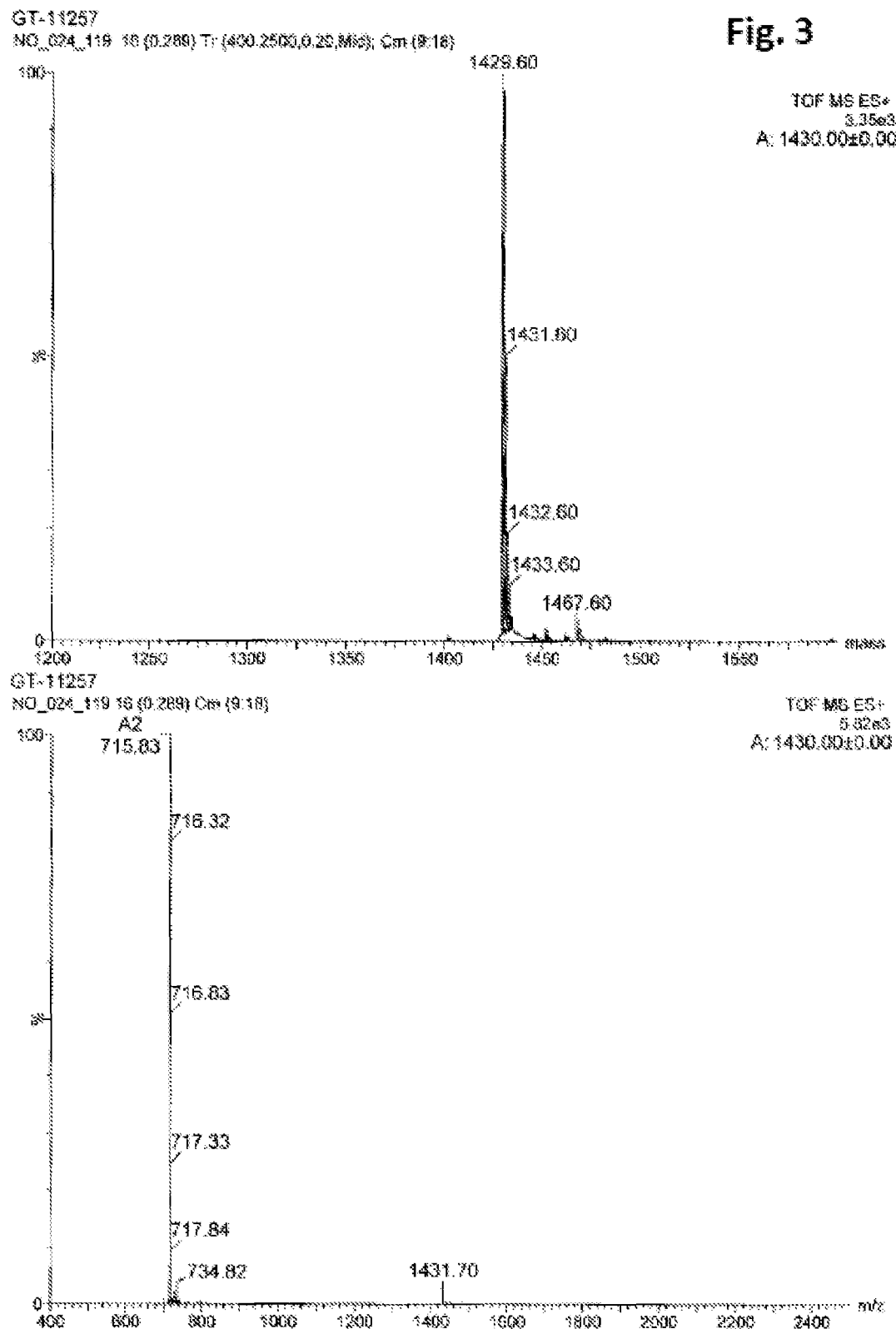
FIG. 3 shows results of mass spectrometry on a synthetic peptide (propionyl)-SCHFGPLTWVCK-NH$_2$ (SEQ ID NO: 18) (GT-11257). The top row shows the deconvolution values from ESI-MS measurement values, and the bottom row shows ESI-MS measurement values.
Figure 4:
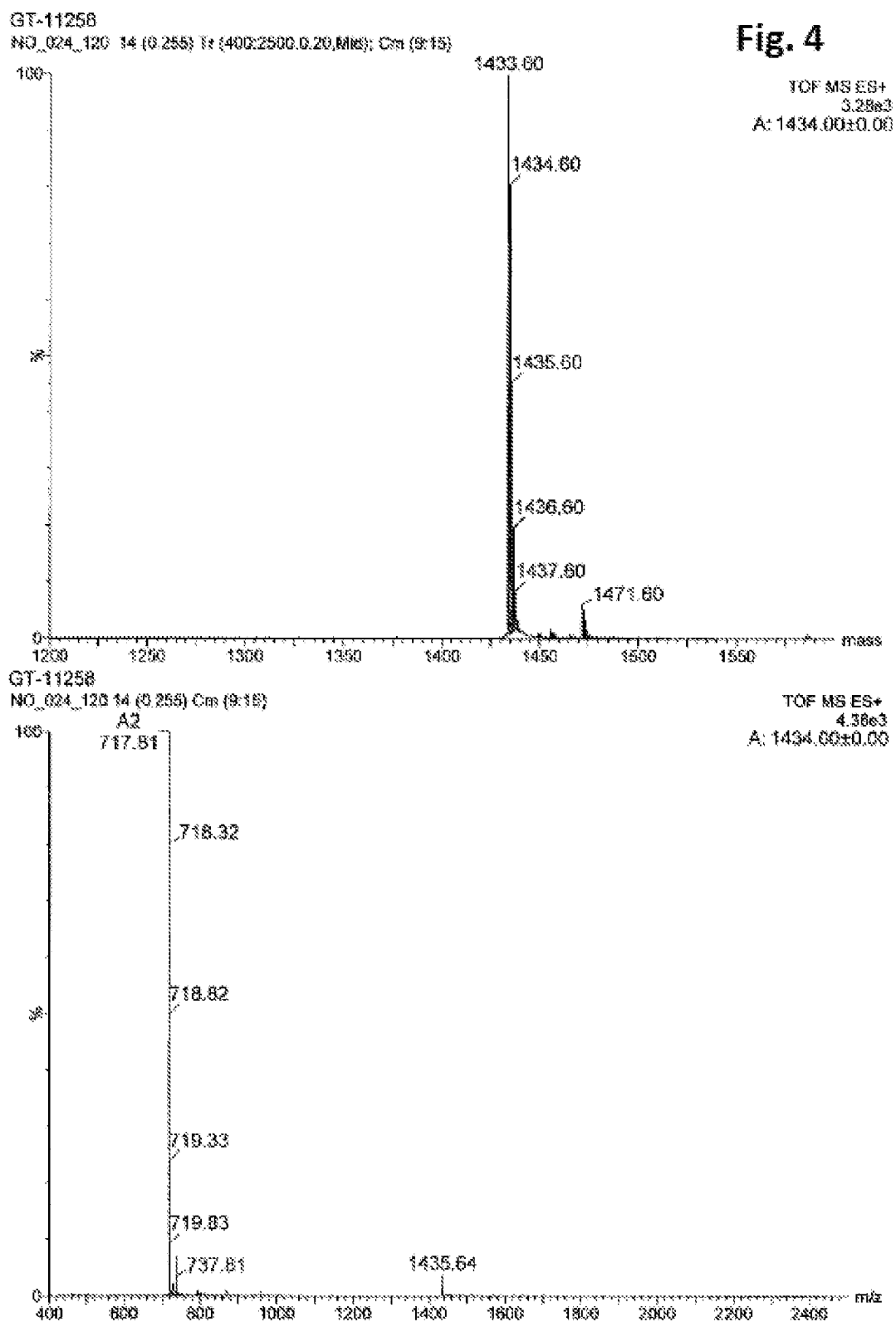
FIG. 4 shows results of mass spectrometry on a synthetic peptide Ac-SCH(p-fluoro-Phe)GPLTWVCK-NH$_2$ (SEQ ID NO: 19) (GT-11258). The top row shows the deconvolution values from ESI-MS measurement values, and the bottom row shows ESI-MS measurement values.
Figure 5:
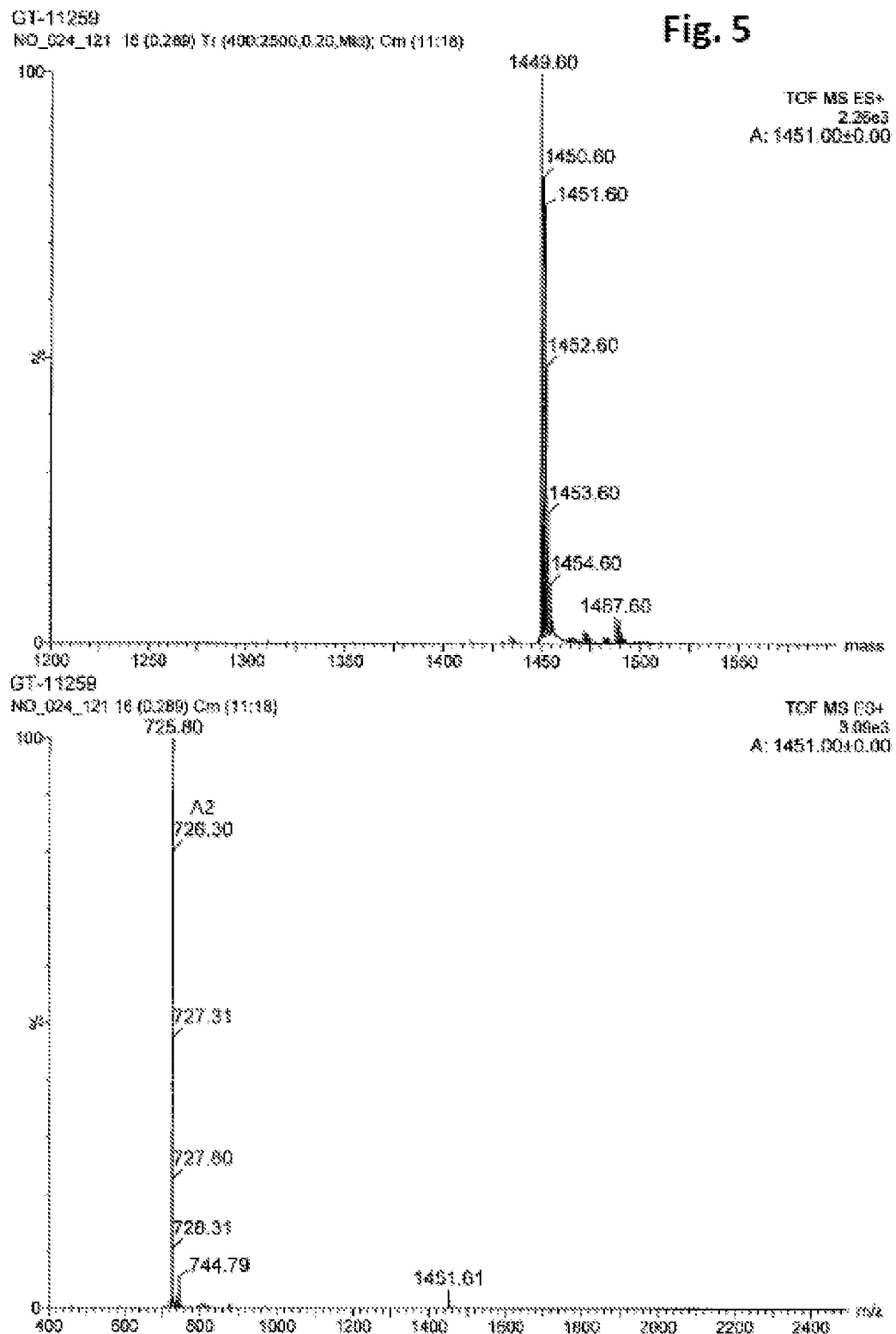
FIG. 5 shows results of mass spectrometry on a synthetic peptide Ac-SCH(p-chloro-Phe)GPLTWVCK-NH$_2$ (SEQ ID NO: 20) (GT-11259). The top row shows the deconvolution values from ESI-MS measurement values, and the bottom row shows ESI-MS measurement values.
Figure 6:
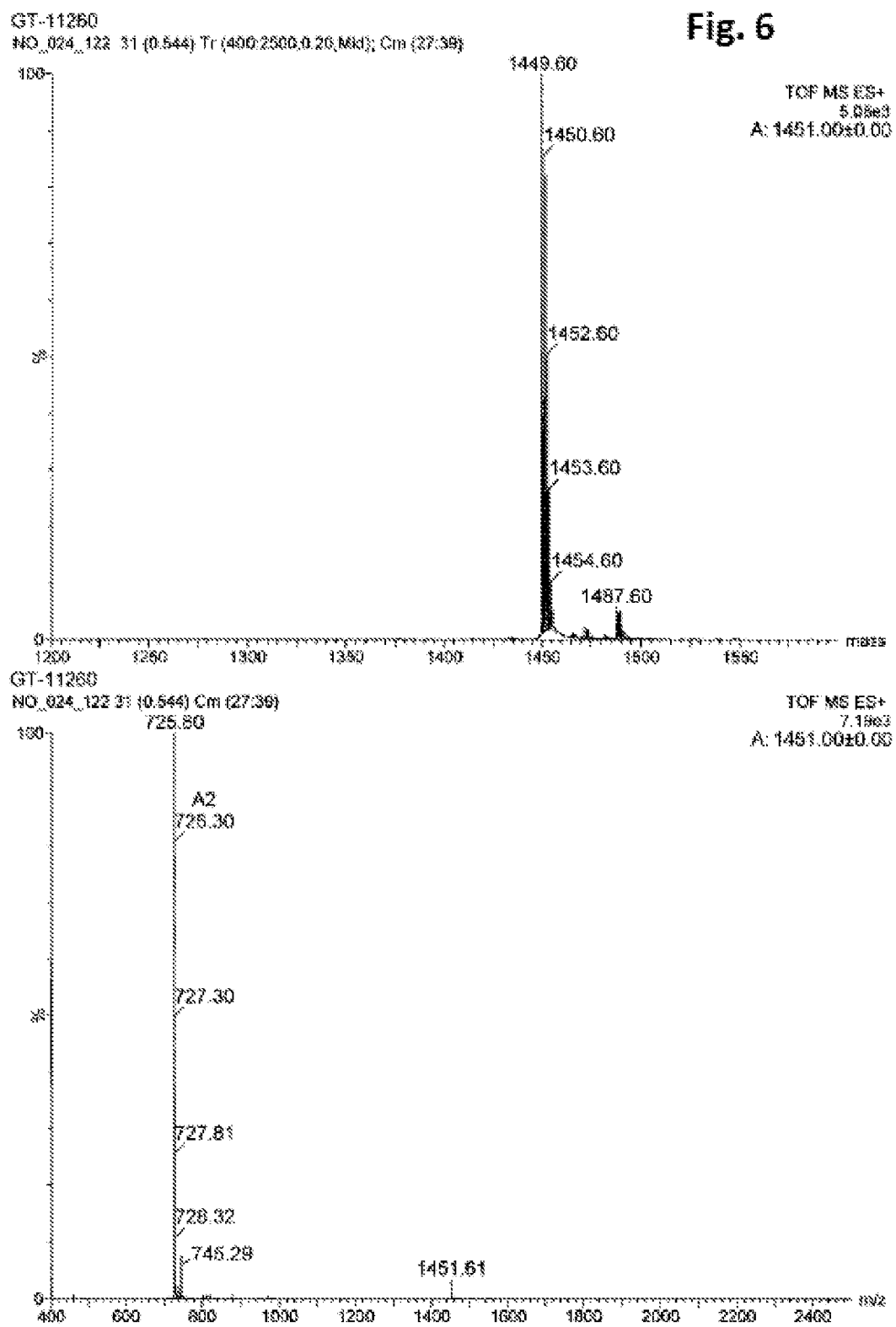
FIG. 6 shows results of mass spectrometry on a synthetic peptide Ac-SCH(m-chloro-Phe)GPLTWVCK-NH$_2$ (SEQ ID NO: 21) (GT-11260). The top row shows the deconvolution values from ESI-MS measurement values, and the bottom row shows ESI-MS measurement values.
Figure 8:
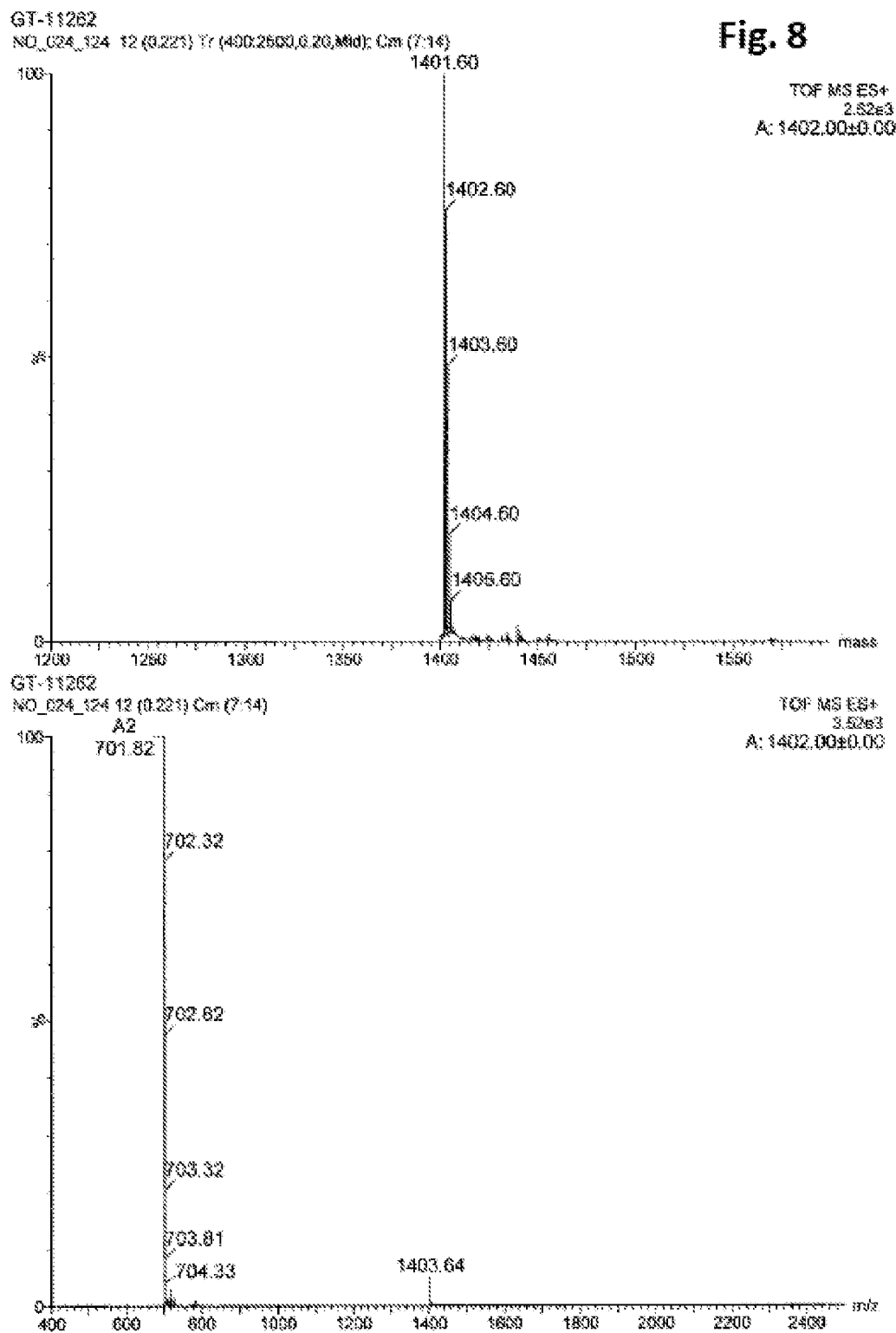
FIG. 8 shows results of mass spectrometry on a synthetic peptide Ac-SCH(phenylglycine)GPLTWVCK-NH$_2$ (SEQ ID NO: 22) (GT-11262). The top row shows the deconvolution values from ESI-MS measurement values, and the bottom row shows ESI-MS measurement values.
Figure 10:
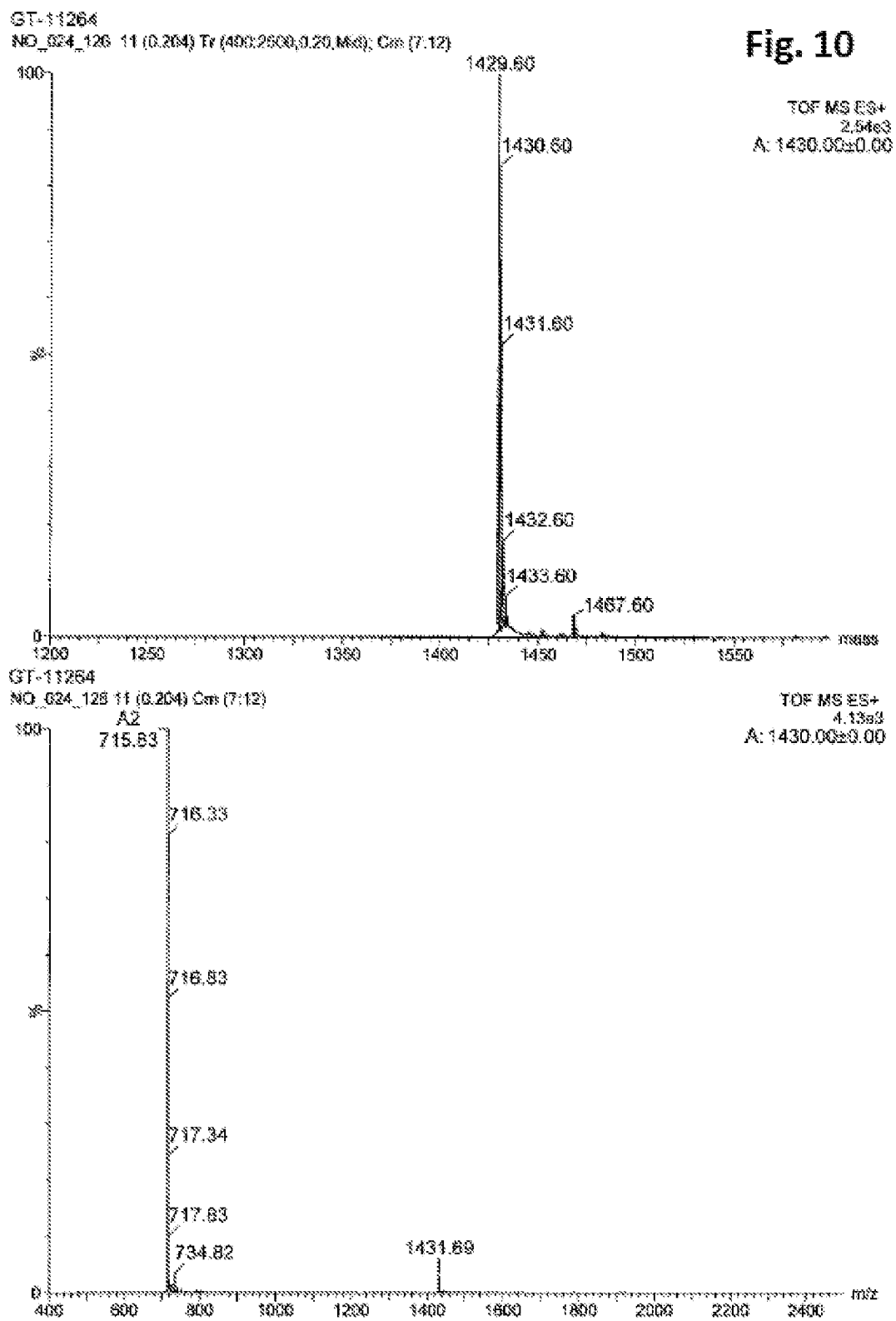
FIG. 10 shows results of mass spectrometry on a synthetic peptide Ac-SCHFAPLTWVCK-NH$_2$ (GT-11264) (SEQ ID NO: 11). The top row shows the deconvolution values from ESI-MS measurement values, and the bottom row shows ESI-MS measurement values.
Figure 12:
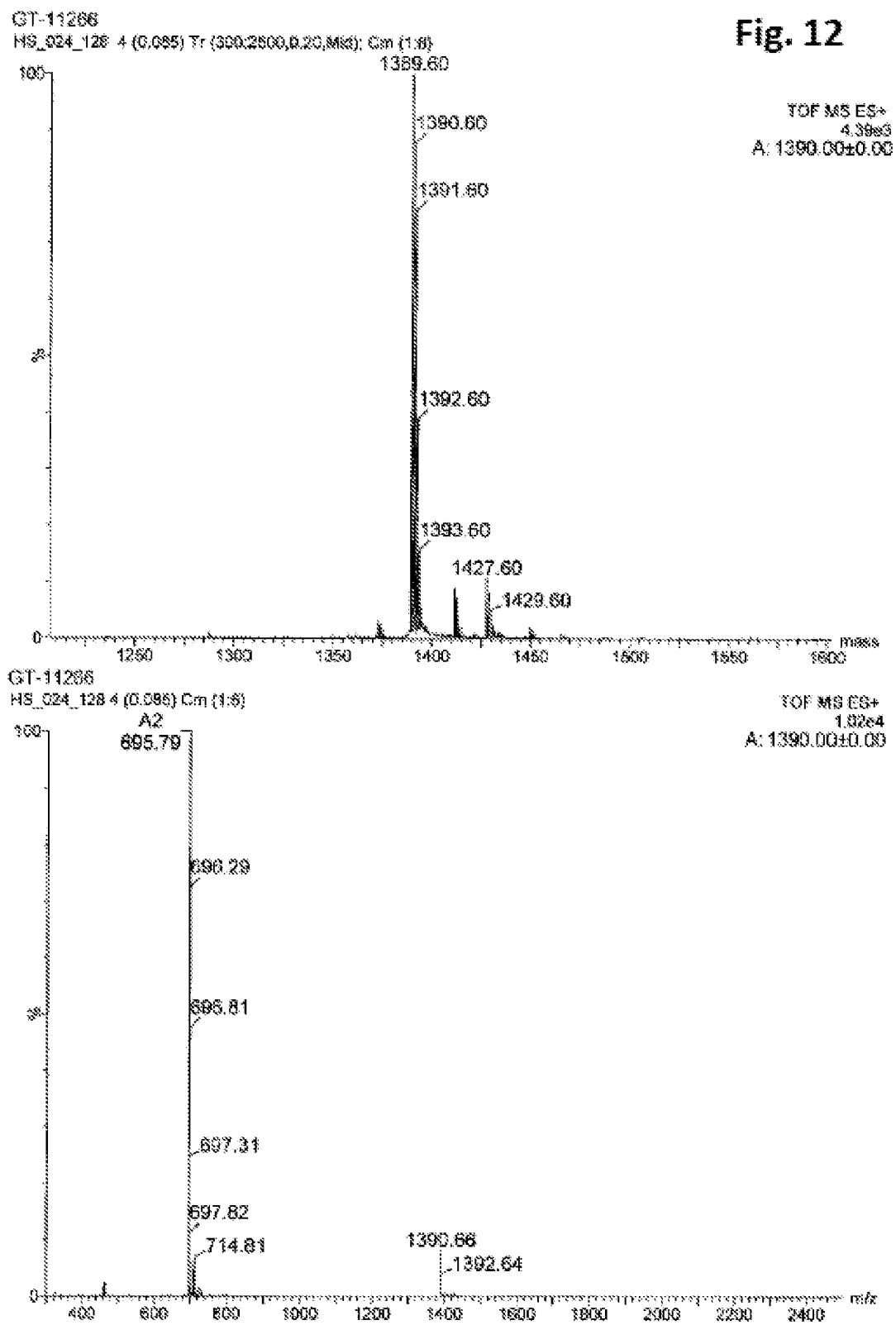
FIG. 12 shows results of mass spectrometry on a synthetic peptide Ac-SCHFGALTWVCK-NH$_2$ (GT-11266) (SEQ ID NO: 12). The top row shows the deconvolution values from ESI-MS measurement values, and the bottom row shows ESI-MS measurement values.
Figure 13:
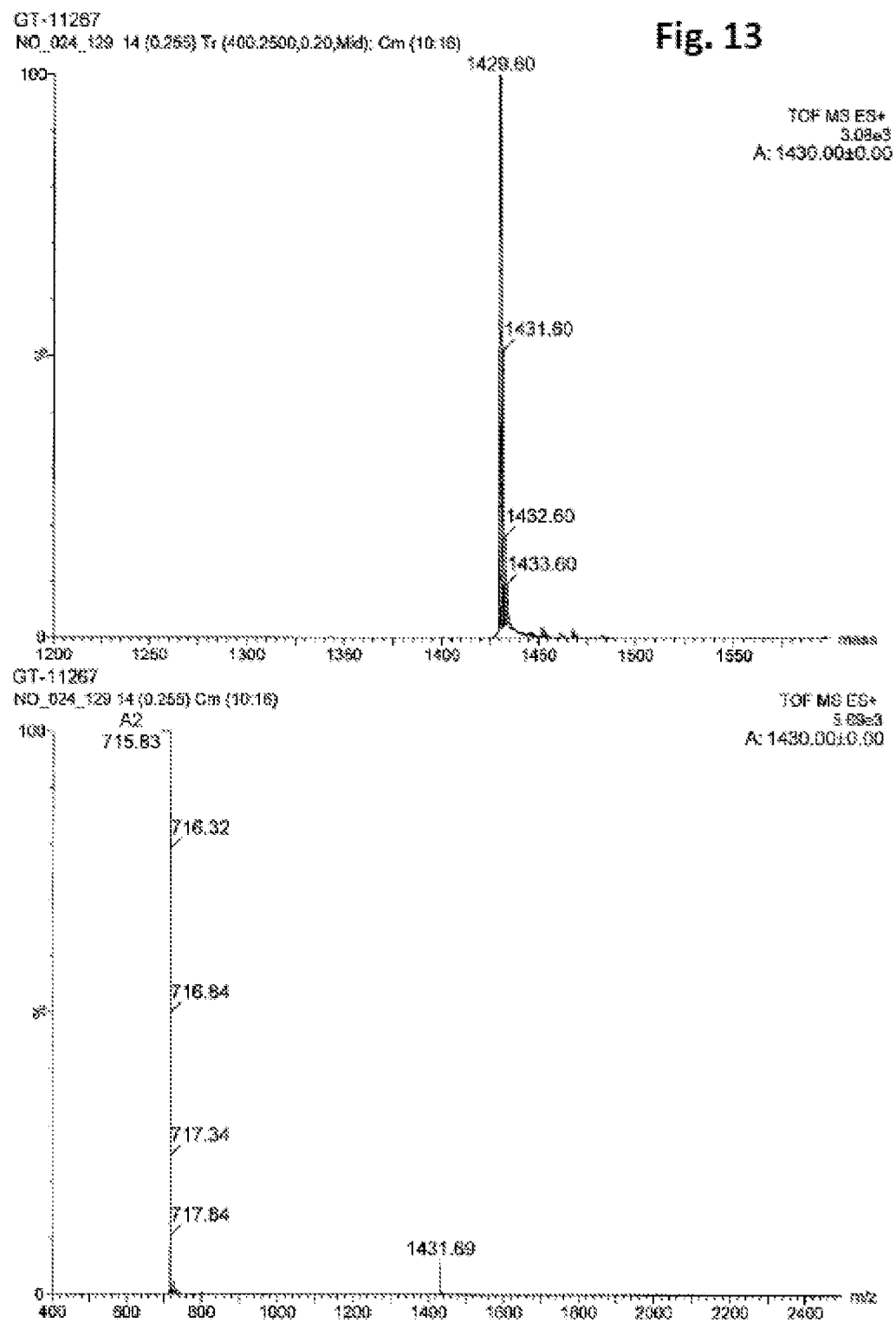
FIG. 13 shows results of mass spectrometry on a synthetic peptide Ac-SCHFG(homoproline)LTWVCK-NH$_2$ (SEQ ID NO:25) (GT-11267). The top row shows the deconvolution values from ESI-MS measurement values, and the bottom row shows ESI-MS measurement values.
Figure 14:
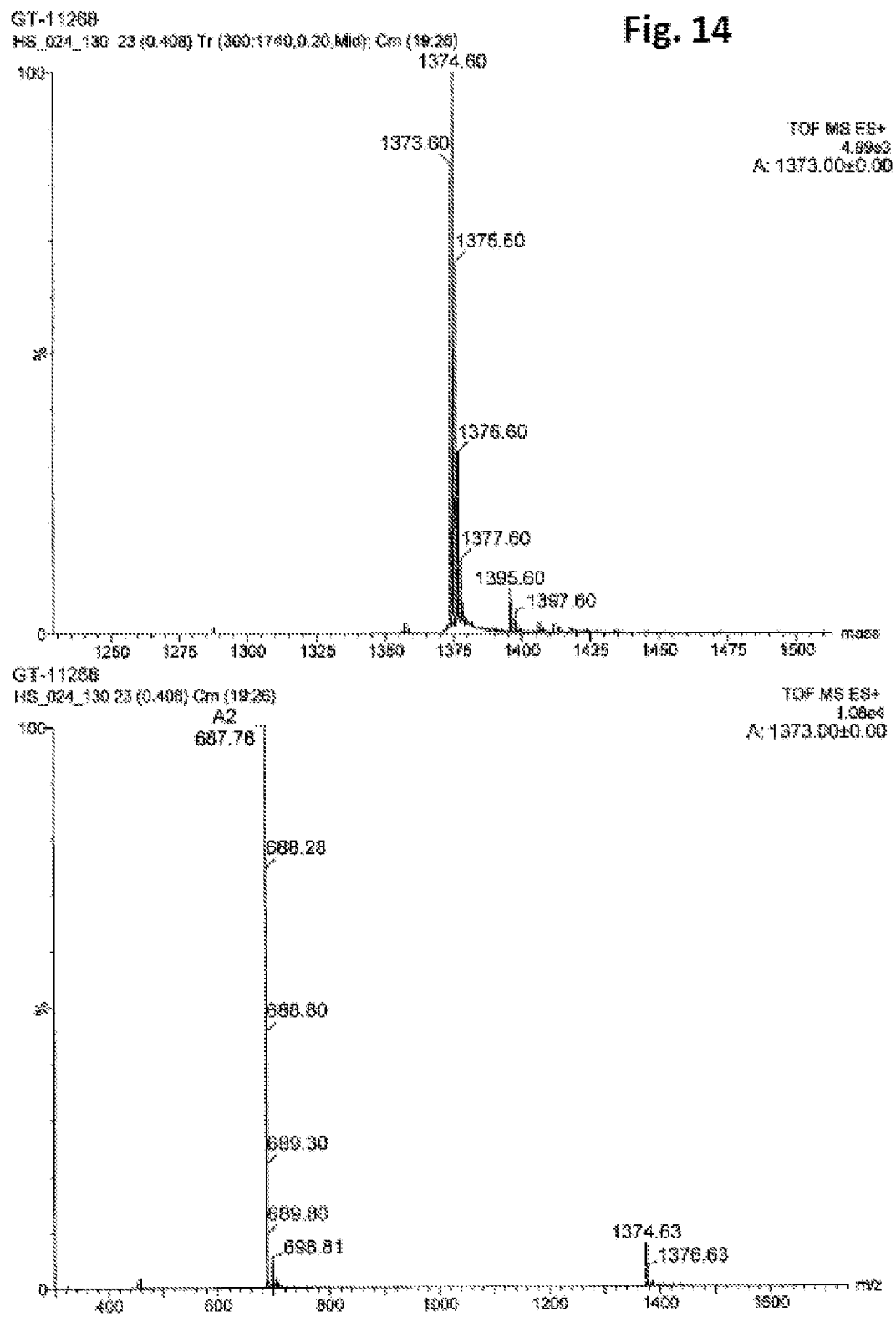
FIG. 14 shows results of mass spectrometry on a synthetic peptide Ac-SCHFGPATWVCK-NH$_2$ (GT-11268) (SEQ ID NO: 13). The top row shows the deconvolution values from ESI-MS measurement values, and the bottom row shows ESI-MS measurement values.
Figure 15:
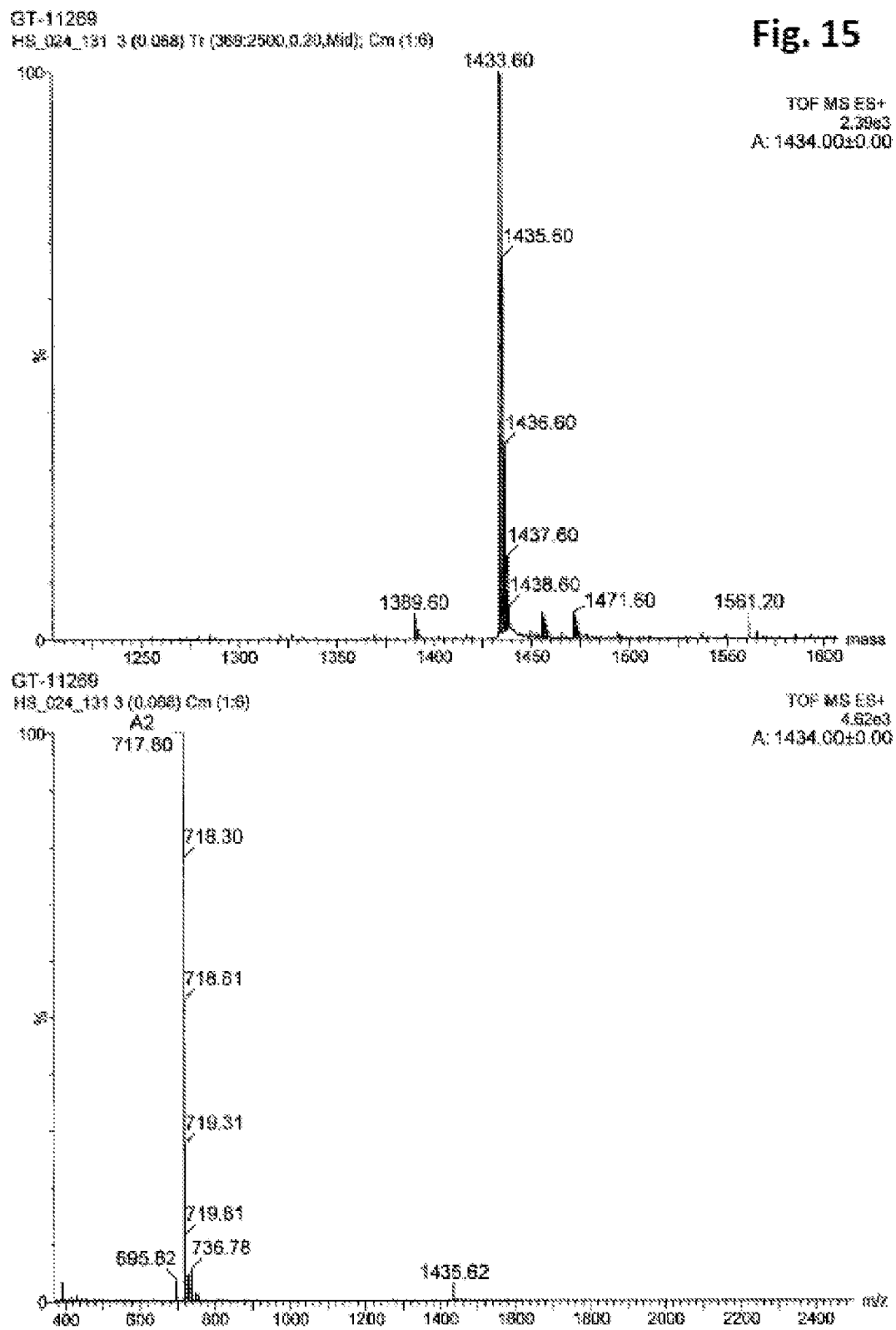
FIG. 15 shows results of mass spectrometry on a synthetic peptide Ac-SCHFGPMTWVCK-NH$_2$ (GT-11269) (SEQ ID NO: 14). The top row shows the deconvolution values from ESI-MS measurement values, and the bottom row shows ESI-MS measurement values.
Figure 16:
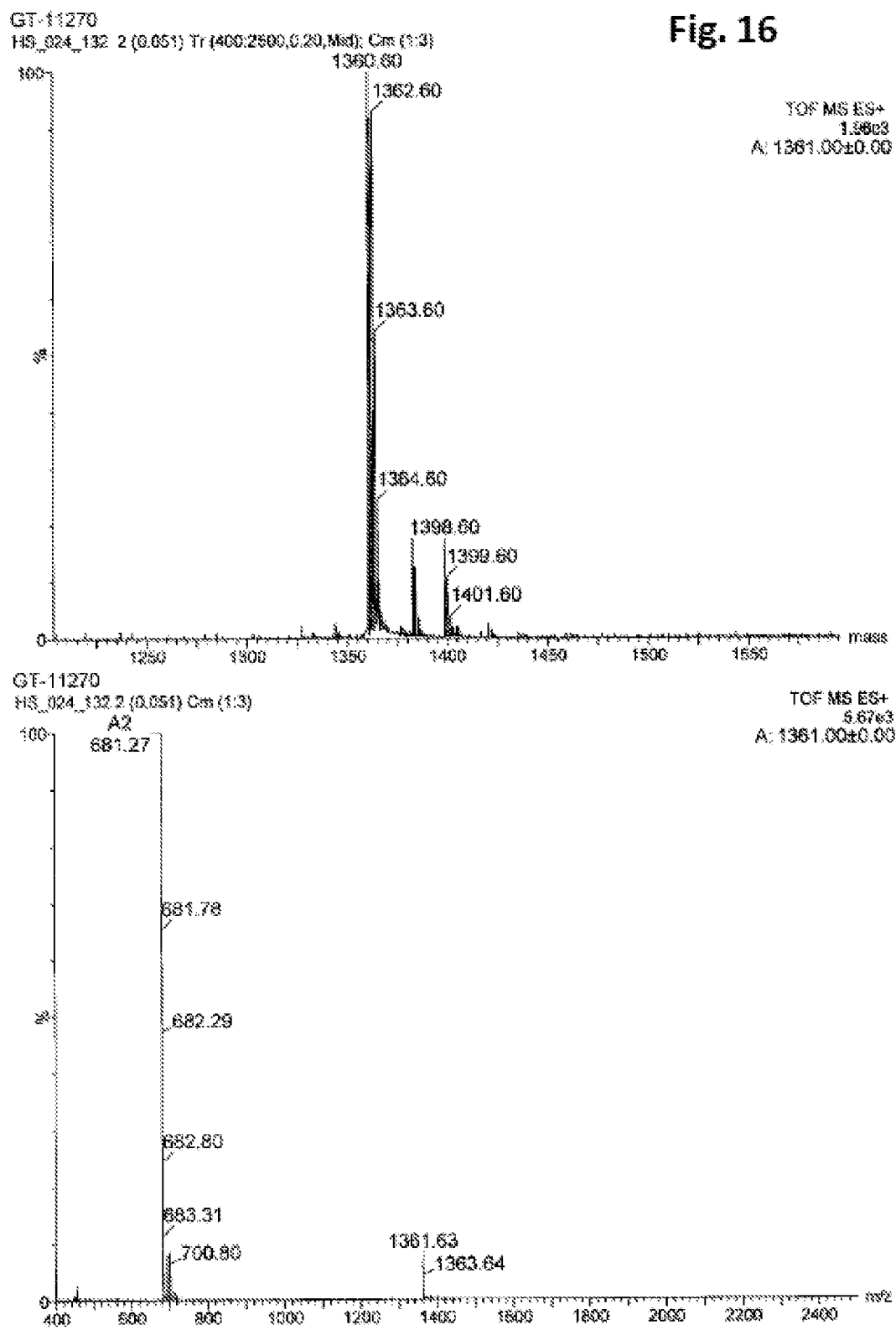
FIG. 16 shows results of mass spectrometry on a synthetic peptide Ac-SCHFGPLTMVCK-NH$_2$ (GT-11270) (SEQ ID NO: 15). The top row shows the deconvolution values from ESI-MS measurement values, and the bottom row shows ESI-MS measurement values.
Figure 18:
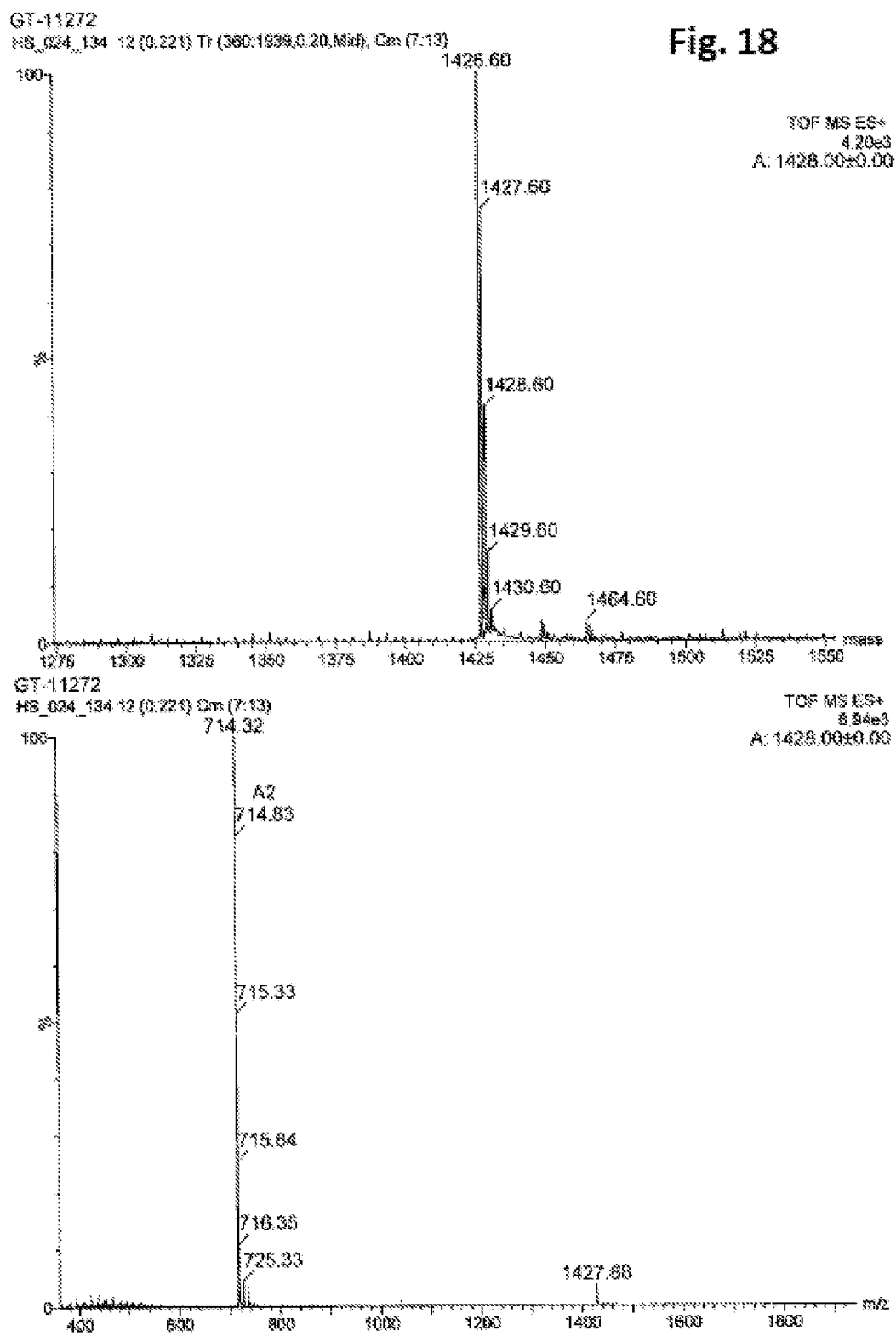
FIG. 18 shows results of mass spectrometry on a synthetic peptide Ac-SCHFGPLT(α-naphthylalanine)VCK-NH$_2$ (SEQ ID NO: 27) (GT-11272). The top row shows the deconvolution values from ESI-MS measurement values, and the bottom row shows ESI-MS measurement values.
Figure 19:
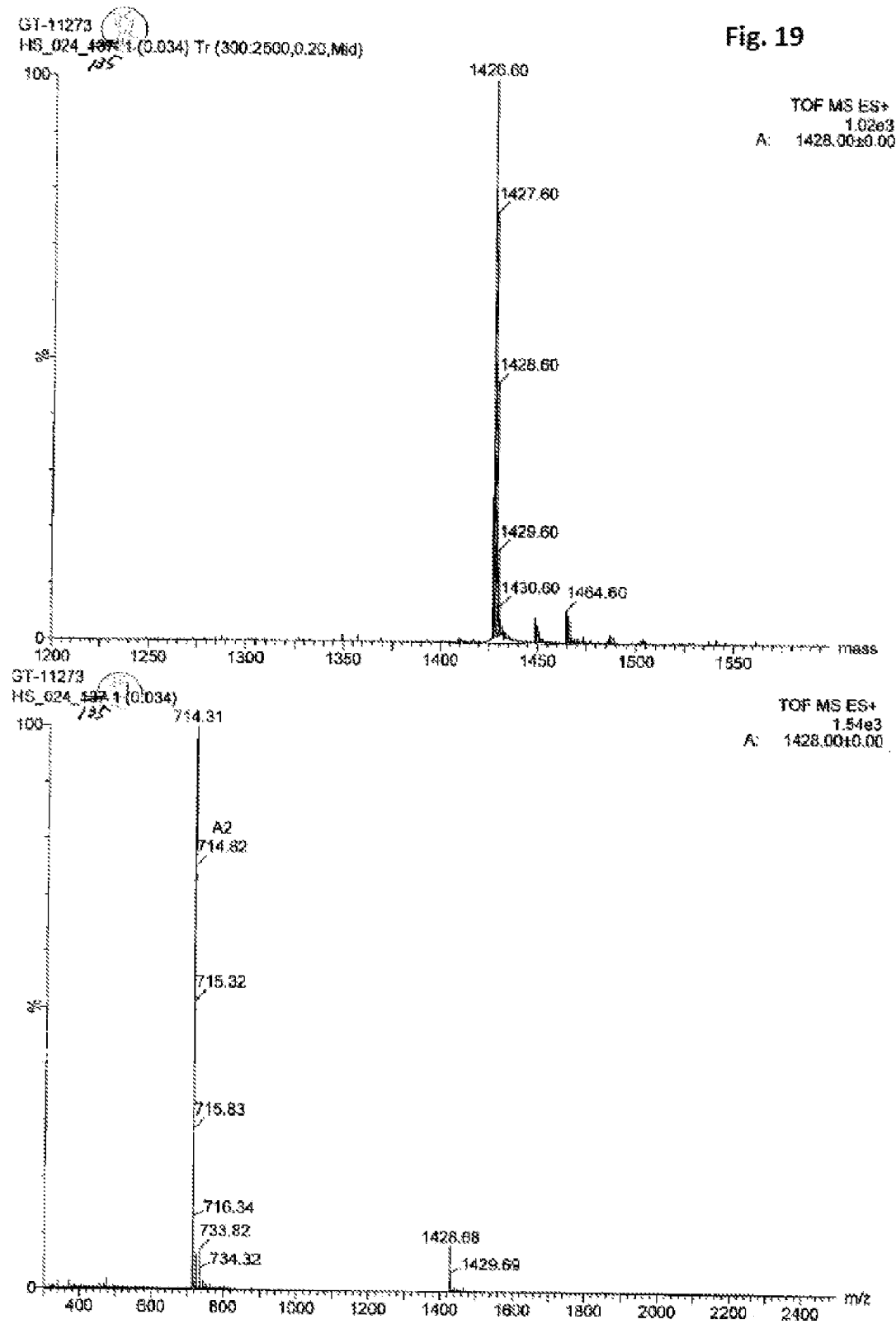
FIG. 19 shows results of mass spectrometry on a synthetic peptide Ac-SCHFGPLT(β-naphthylalanine)VCK-NH$_2$ (SEQ ID NO: 28) (GT-11273). The top row shows the deconvolution values from ESI-MS measurement values, and the bottom row shows ESI-MS measurement values.
Figure 20:
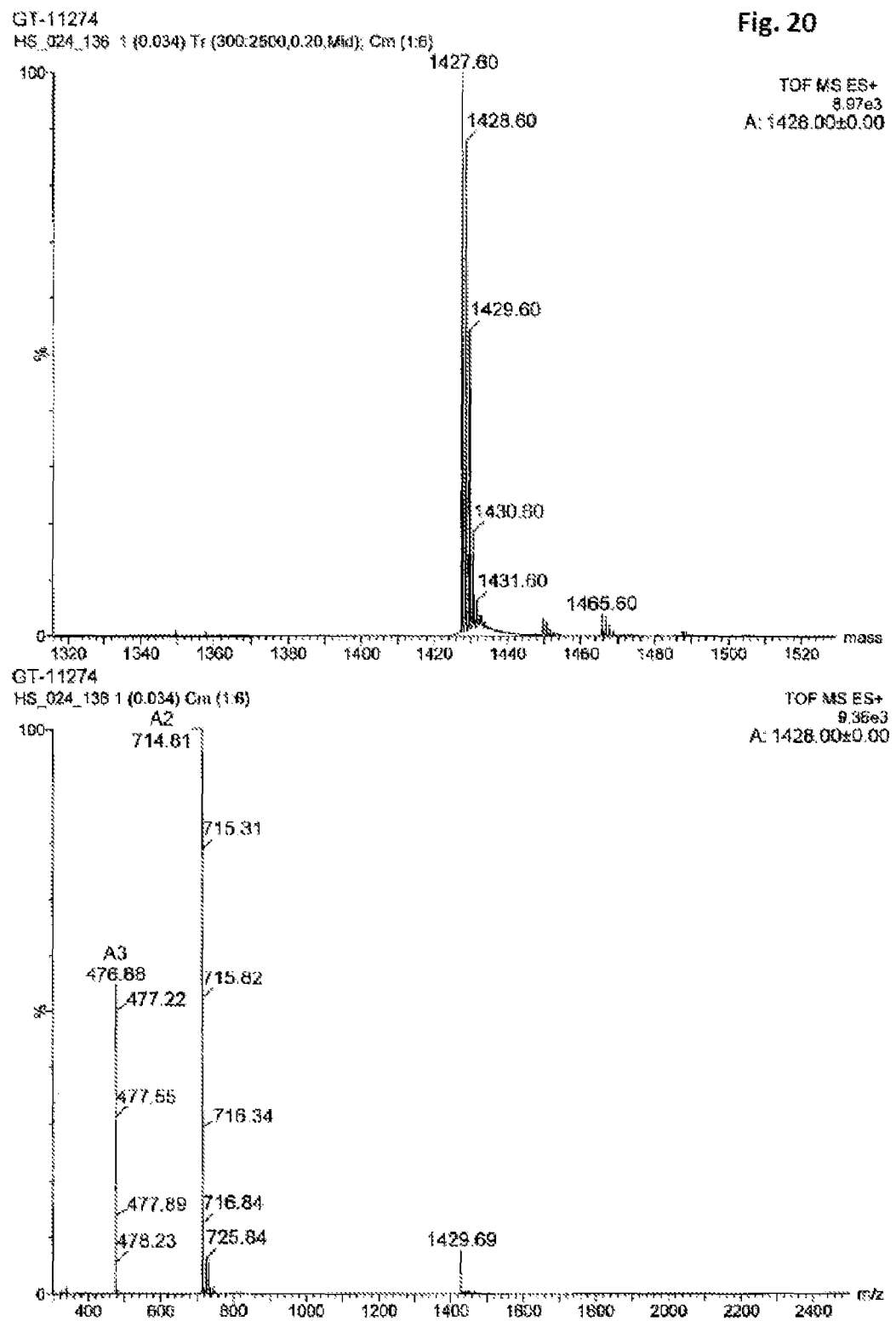
FIG. 20 shows results of mass spectrometry on a synthetic peptide Ac-SCHFGPLT(8-quinolylalanine)VCK-NH$_2$ (SEQ ID NO: 29) (GT-11274). The top row shows the deconvolution values from ESI-MS measurement values, and the bottom row shows ESI-MS measurement values.
Figure 21:
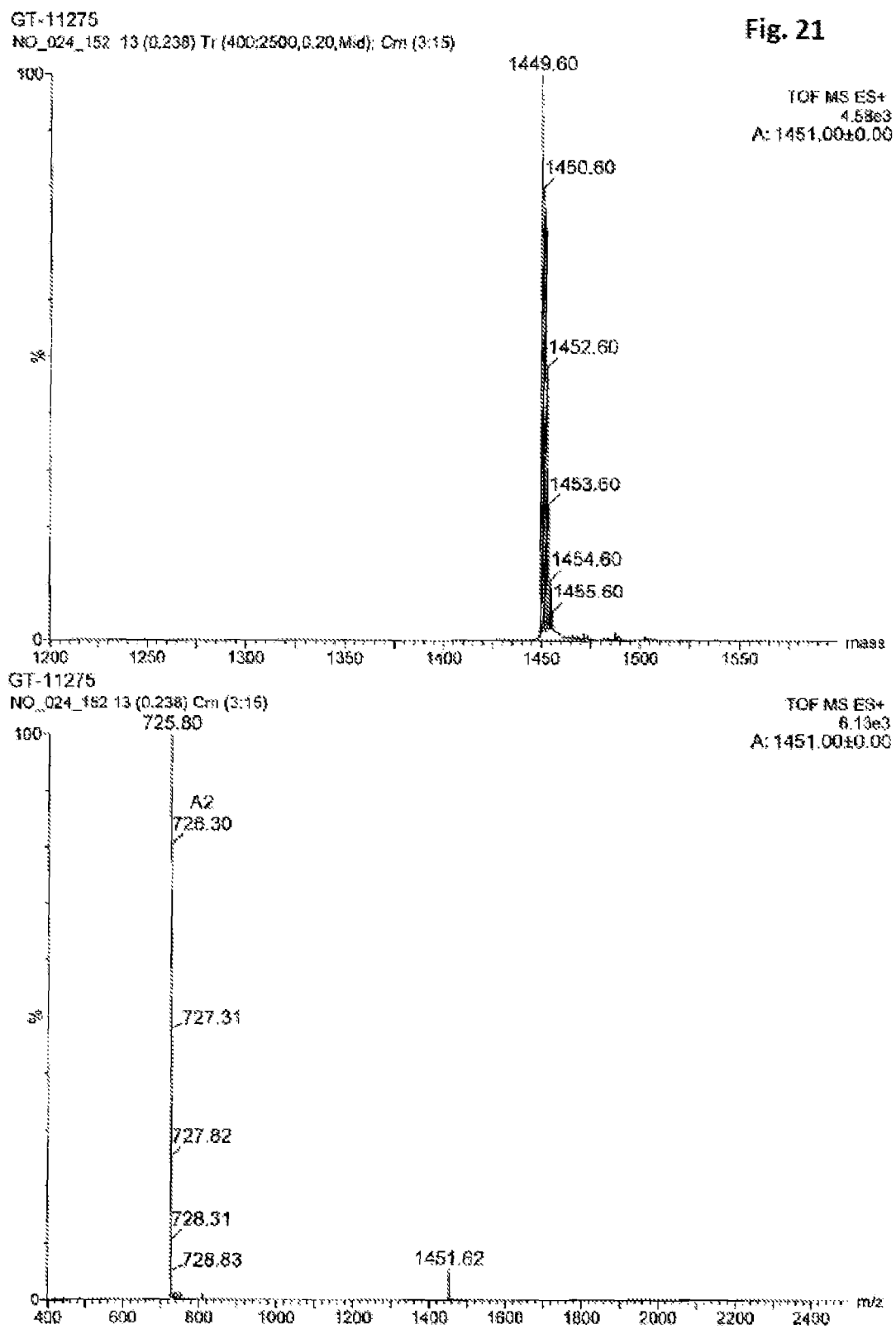
FIG. 21 shows results of mass spectrometry on a synthetic peptide Ac-SCHFGPLT(6-chloro-Trp)VCK-NH$_2$ (SEQ ID NO: 30) (GT-11275). The top row shows the deconvolution values from ESI-MS measurement values, and the bottom row shows ESI-MS measurement values.
Figure 22:
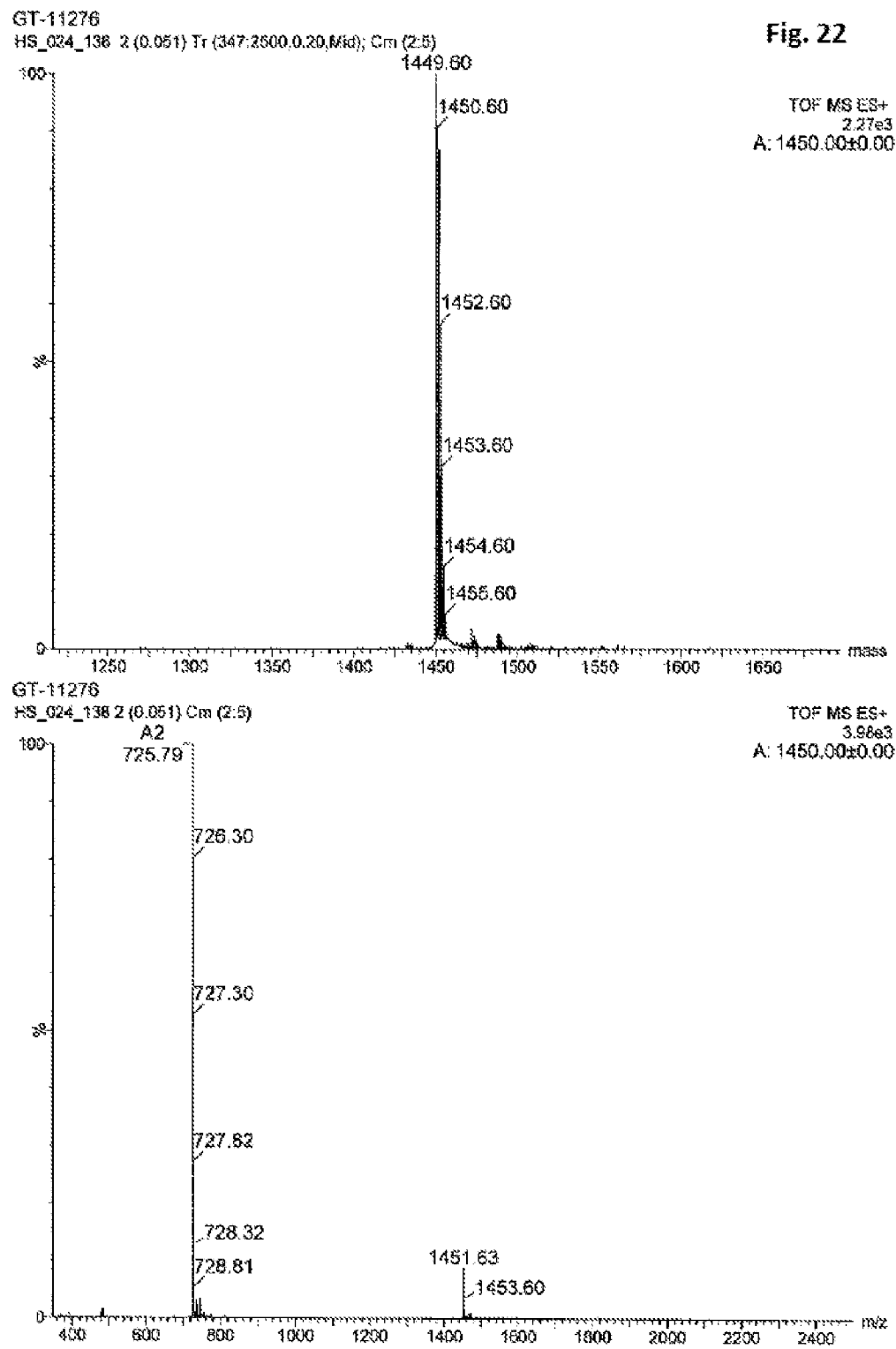
FIG. 22 shows results of mass spectrometry on a synthetic peptide Ac-SCHFGPLT(5-chloro-Trp)VCK-NH$_2$ (SEQ ID NO: 31) (GT-11276). The top row shows the deconvolution values from ESI-MS measurement values, and the bottom row shows ESI-MS measurement values.
Figure 23:
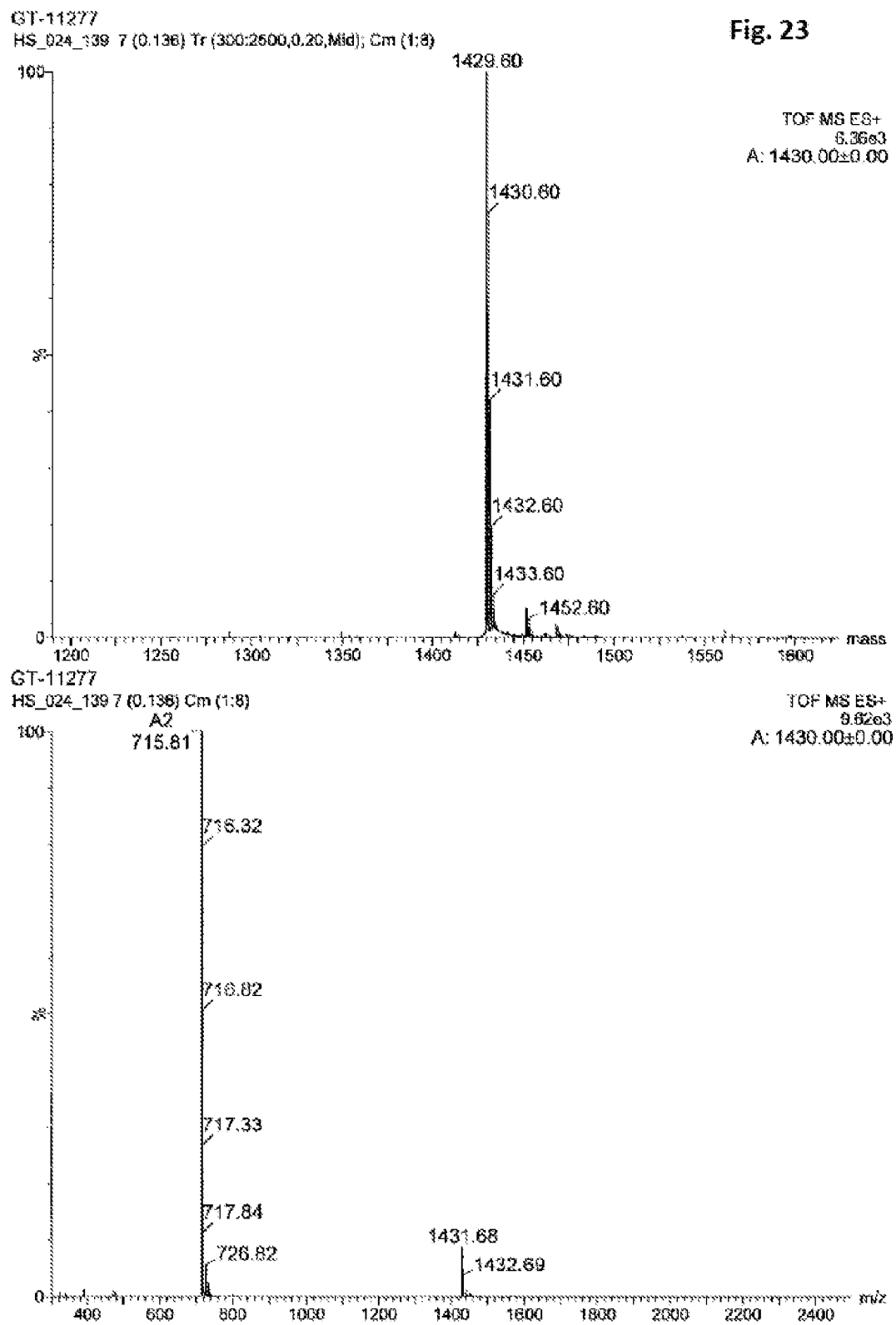
FIG. 23 shows results of mass spectrometry on a synthetic peptide Ac-SCHFGPLTWV(homocysteine)K-NH$_2$ (SEQ ID NO: 32) (GT-11277). The top row shows the deconvolution values from ESI-MS measurement values, and the bottom row shows ESI-MS measurement values.
Figure 24:
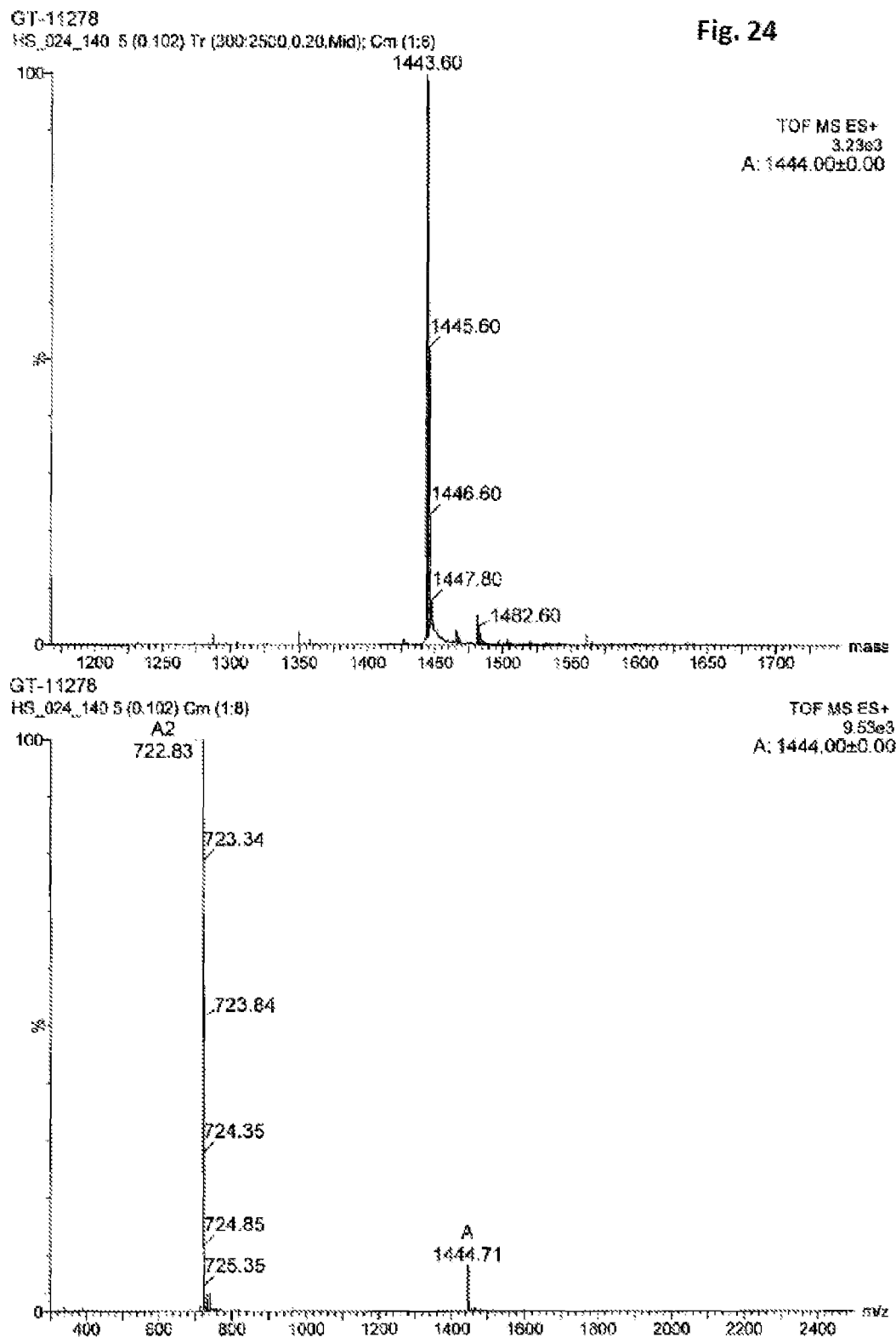
FIG. 24 shows results of mass spectrometry on a synthetic peptide Ac-SCHFGPLTWV(penicillamine)K-NH$_2$ (SEQ ID NO: 33) (GT-11278). The top row shows the deconvolution values from ESI-MS measurement values, and the bottom row shows ESI-MS measurement values.
Figure 26:
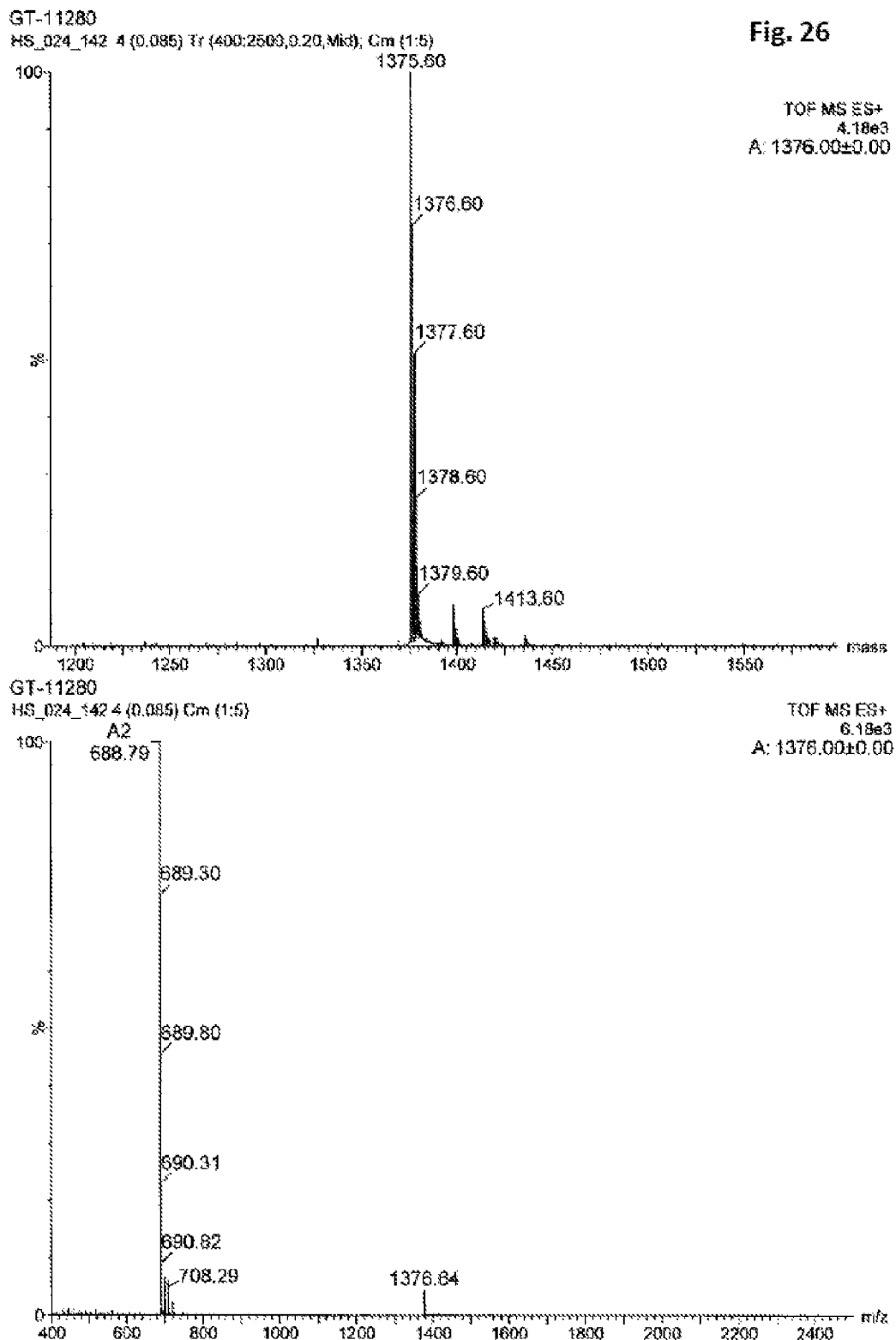
FIG. 26 shows results of mass spectrometry on a synthetic peptide Ac-KCVWTLGGFHCS-NH$_2$ (SEQ ID NO: 35) (GT-11280). The top row shows the deconvolution values from ESI-MS measurement values, and the bottom row shows ESI-MS measurement values.
Figure 27:
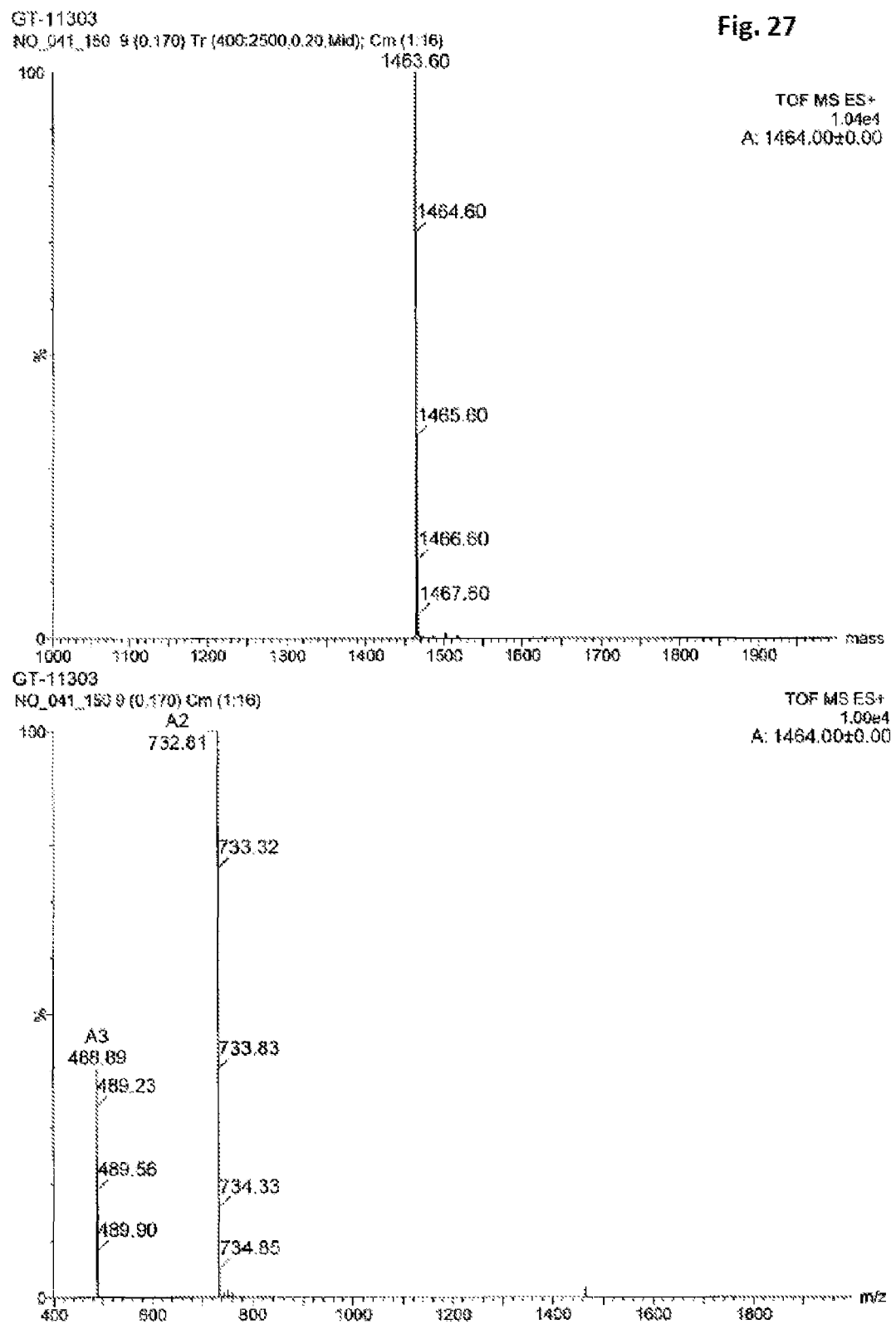
FIG. 27 shows results of mass spectrometry on a synthetic peptide Ac-SCH(3,4-difluoro-Phe)GPLT(8-quinolylalanine)VCK-NH$_2$ (SEQ ID NO: 36) (GT-11303). The top row shows the deconvolution values from ESI-MS measurement values, and the bottom row shows ESI-MS measurement values.
Figure 28:
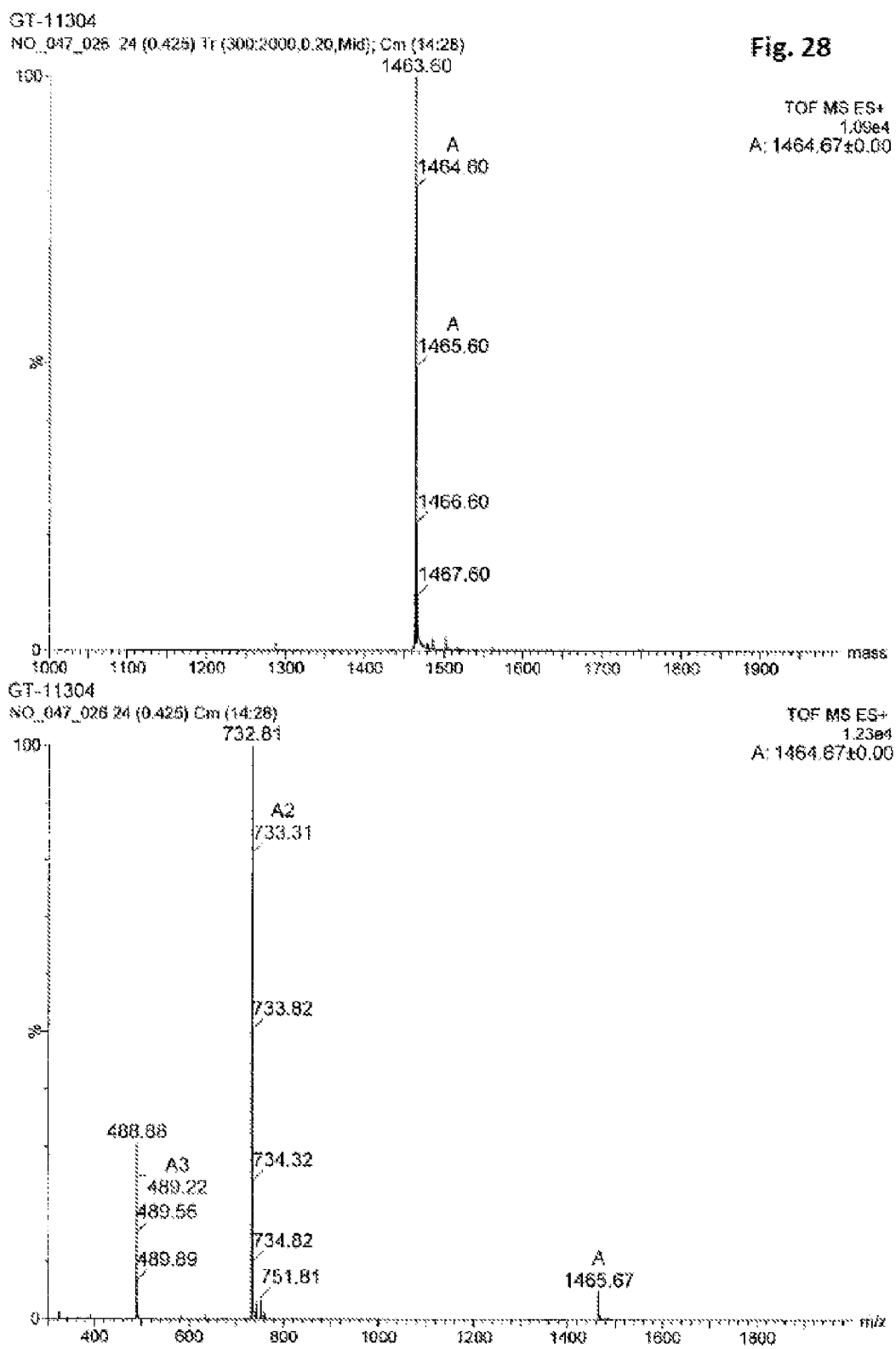
FIG. 28 FIG. 28 shows results of mass spectrometry on a synthetic peptide Ac-SCH(3,4-difluoro-Phe)GPLT(2-quinolylalanine)VCK-NH$_2$ (SEQ ID NO: 37) (GT-11304). The top row shows the deconvolution values from ESI-MS measurement values, and the bottom row shows ESI-MS measurement values.
Figure 29:
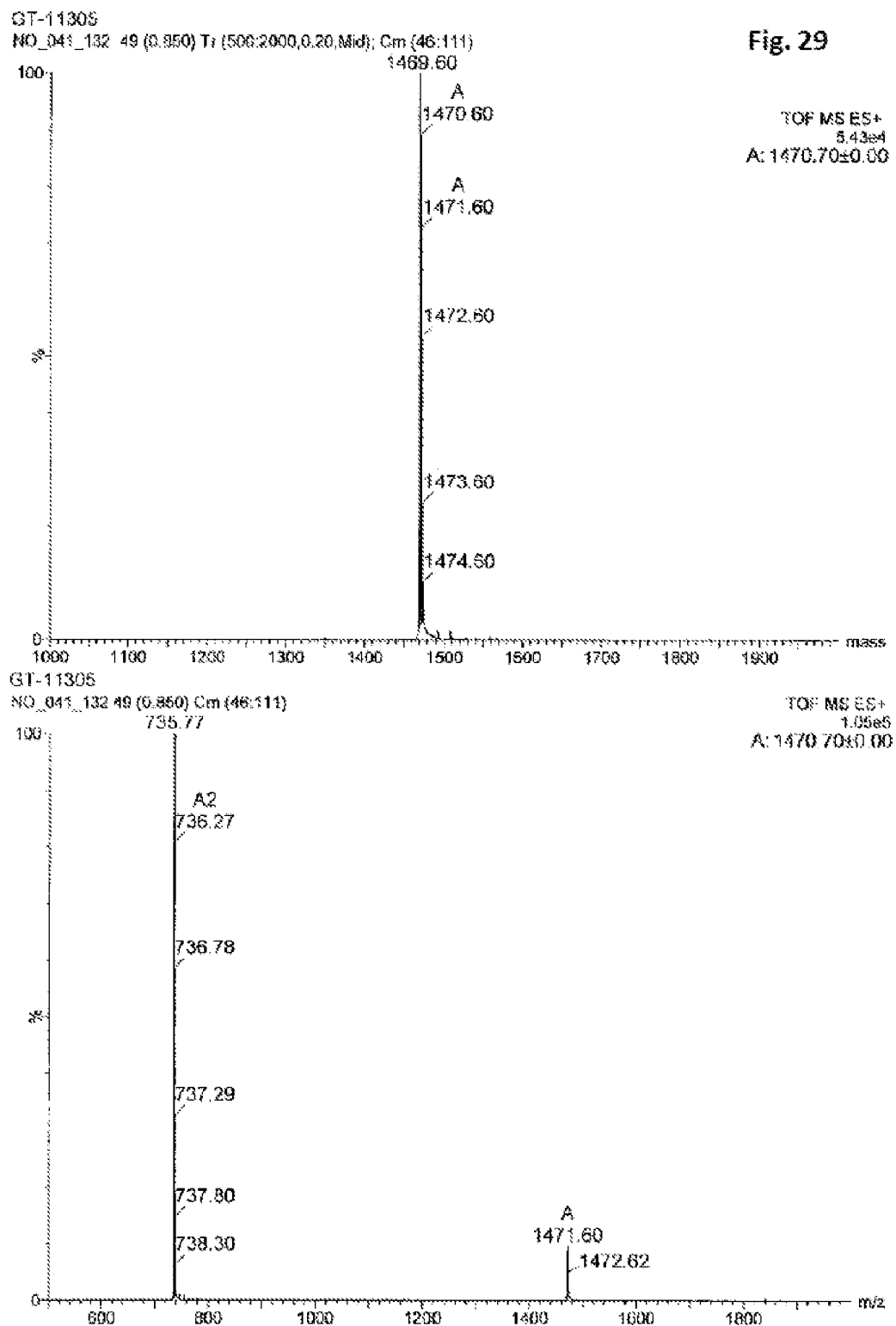
FIG. 29 shows results of mass spectrometry on a synthetic peptide Ac-SCH(3,4-difluoro-Phe)GPLT(2-benzothiazolylalanine)VCK-NH$_2$ (SEQ ID NO: 38) (GT-11305). The top row shows the deconvolution values from ESI-MS measurement values, and the bottom row shows ESI-MS measurement values.
Figure 30:
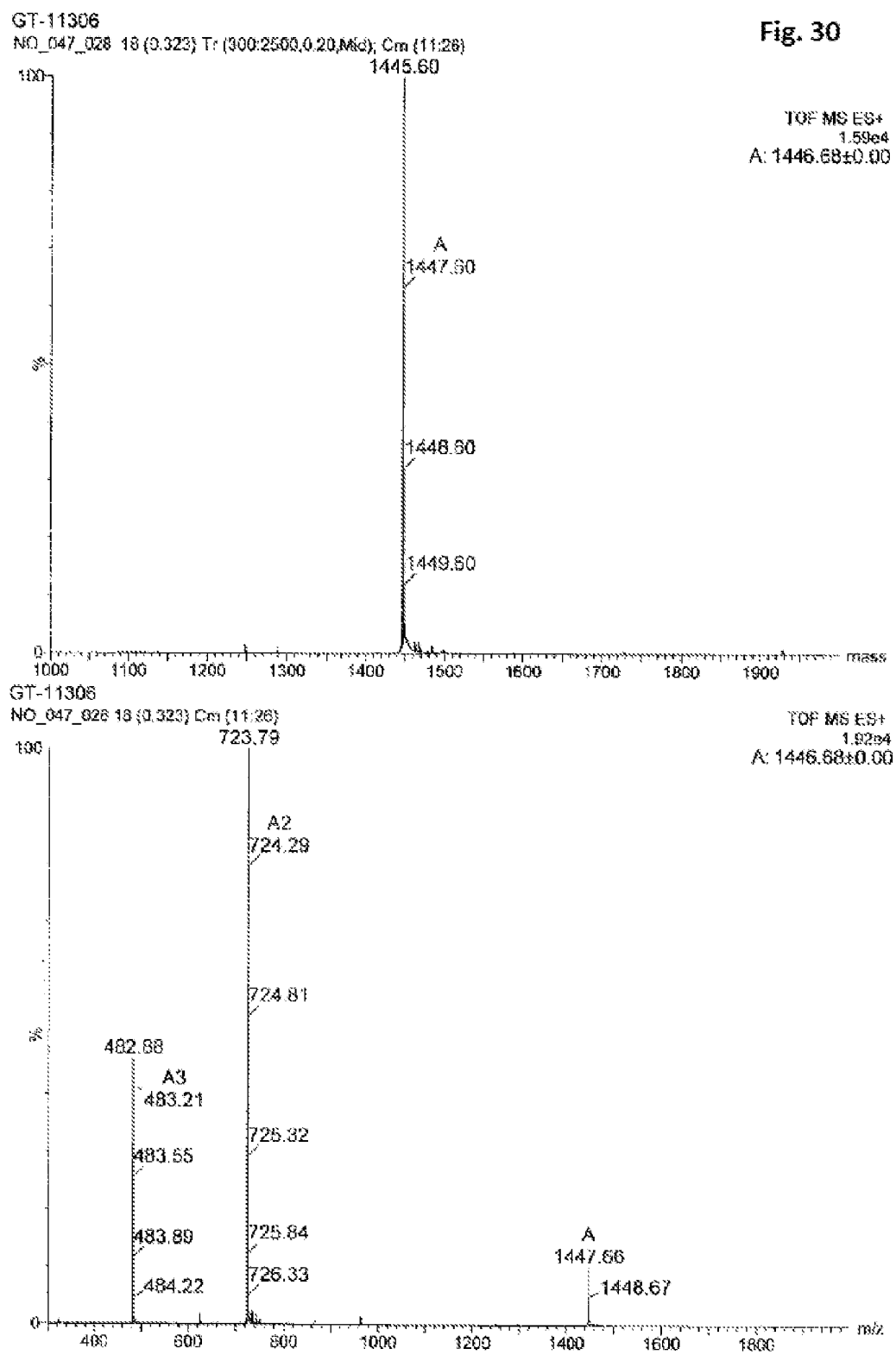
FIG. 30 shows results of mass spectrometry on a synthetic peptide Ac-SCH(p-fluoro-Phe)GPLT(2-quinolylalanine)VCK-NH$_2$ (SEQ ID NO: 39) (GT-11306). The top row shows the deconvolution values from ESI-MS measurement values, and the bottom row shows ESI-MS measurement values.
Figure 31:
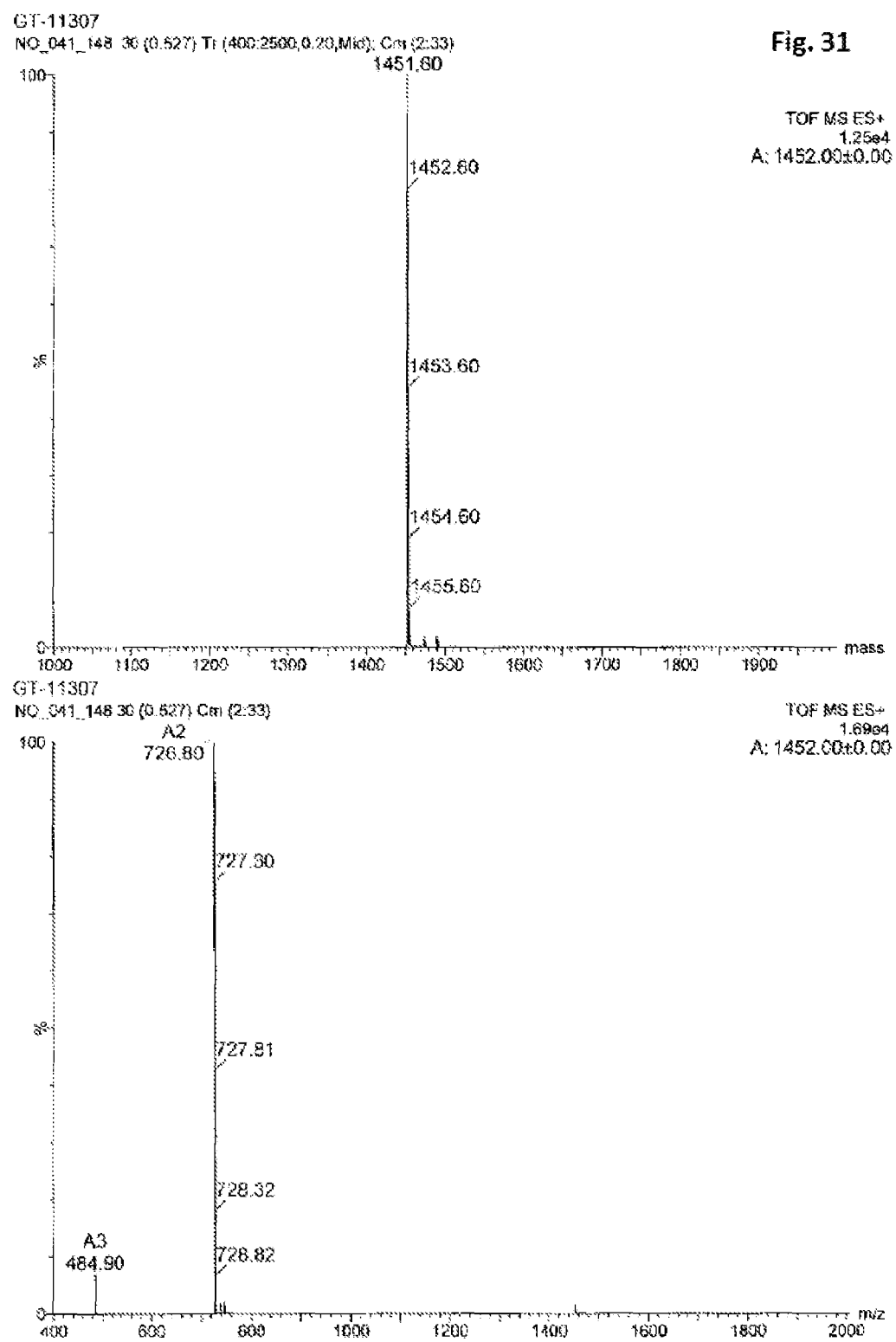
FIG. 31 shows results of mass spectrometry on a synthetic peptide Ac-SCH(p-fluoro-Phe)GPLT(2-benzothiazolylalanine)VCK-NH$_2$ (SEQ ID NO: 40) (GT-11307). The top row shows the deconvolution values from ESI-MS measurement values, and the bottom row shows ESI-MS measurement values.
Figure 32:
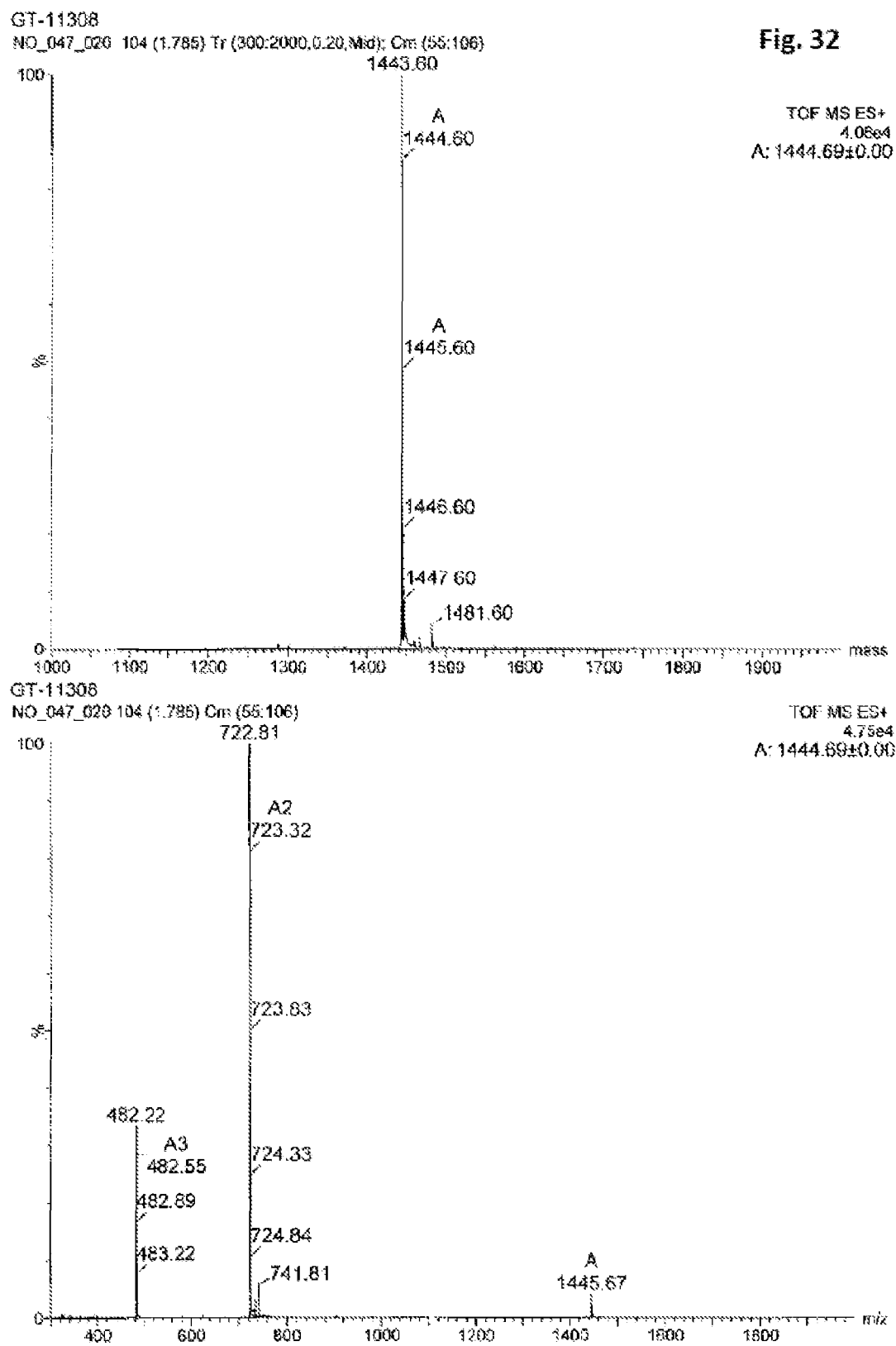
FIG. 32 shows results of mass spectrometry on a synthetic peptide Ac-SCHYGPLT(2-quinolylalanine)VCK-NH$_2$ (SEQ ID NO: 41) (GT-11308). The top row shows the deconvolution values from ESI-MS measurement values, and the bottom row shows ESI-MS measurement values.
Figure 34:
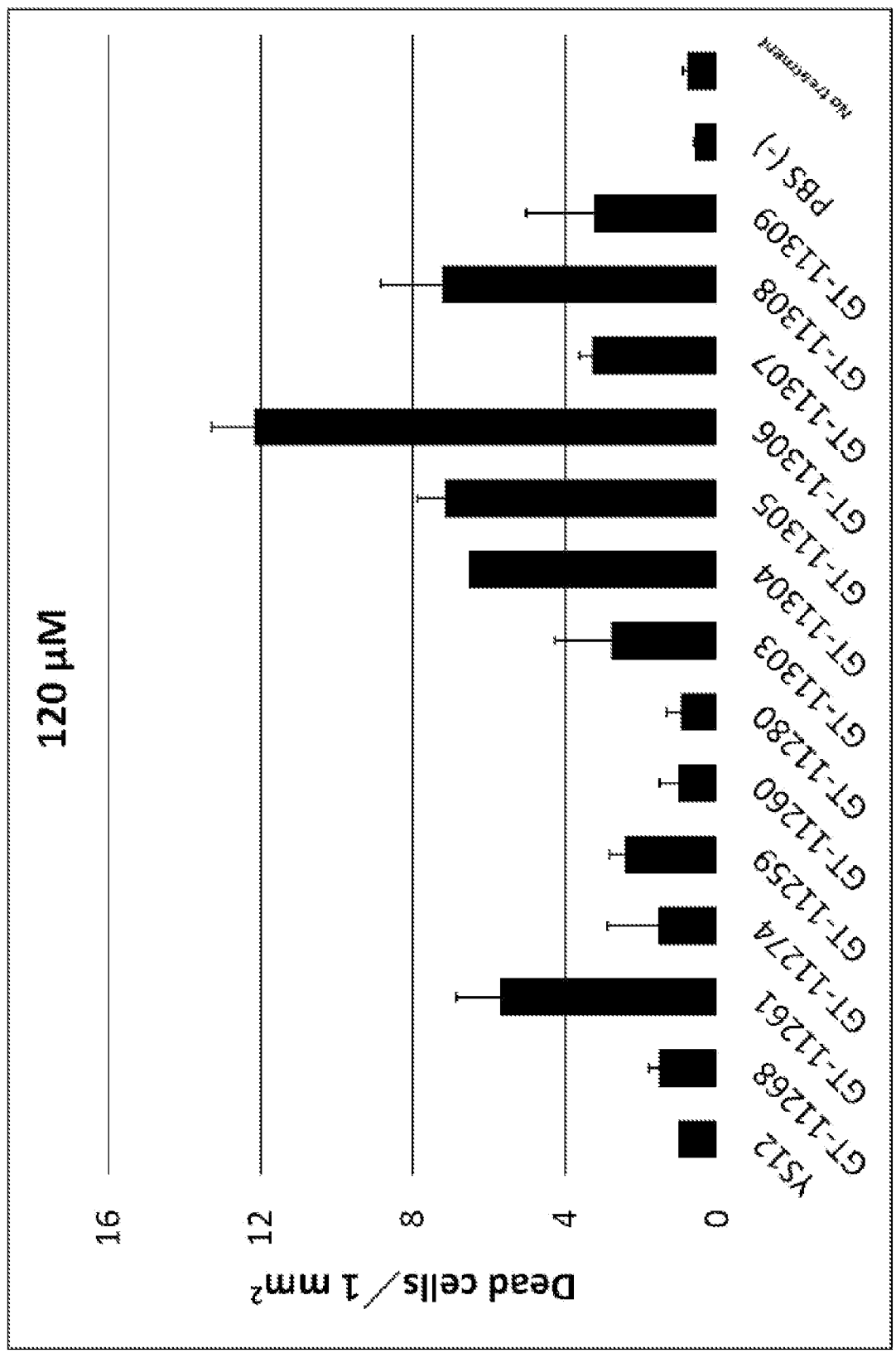
FIG. 34 shows the human liver cancer derived HepG2 cell killing effect at a concentration of 120 μM of each peptide in Example 2. The horizontal axis indicates treatment with YS12, GT-11268, GT-11261, GT-11274, GT-11259, GT-11260, GT-11280, GT-11303, GT-11304, GT-11305, GT-11306, GT-11307, GT-11308, GT-11309, and PBS(−) and no treatment. The vertical axis indicates the mean and the standard deviation (when n=3) of the number of dead cells observed within a 1 mm$^2$ section.
Figure 35:
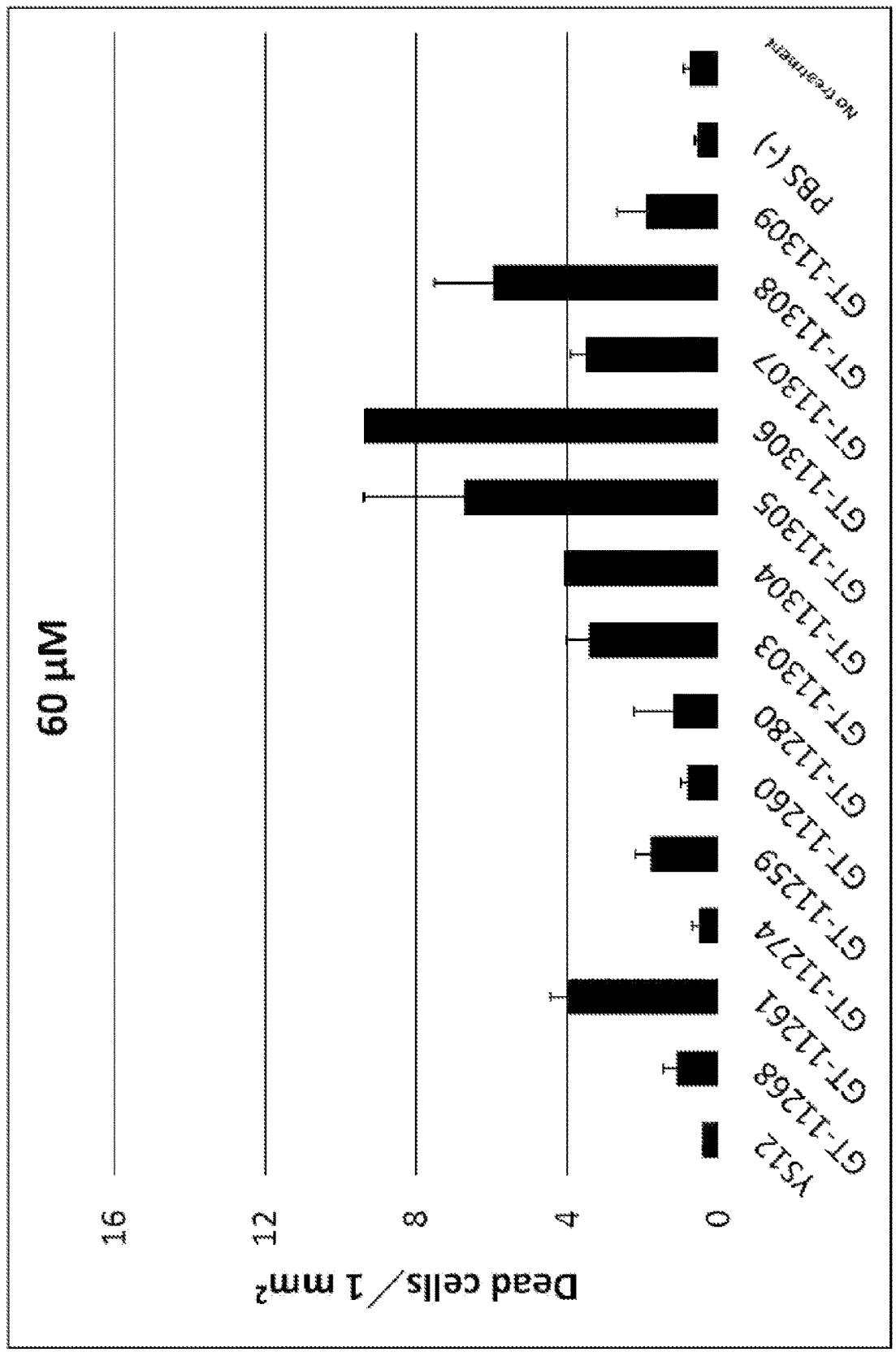
FIG. 35 shows the human liver cancer derived HepG2 cell killing effect at a concentration of 60 μM of each peptide in Example 2. The horizontal axis indicates treatment with YS12, GT-11268, GT-11261, GT-11274, GT-11259, GT-11260, GT-11280, GT-11303, GT-11304, GT-11305, GT-11306, GT-11307, GT-11308, GT-11309, and PBS(−) and no treatment. The vertical axis indicates the mean and the standard deviation (when n=3) of the number of dead cells observed within a 1 mm$^2$ section.
Figure 36:
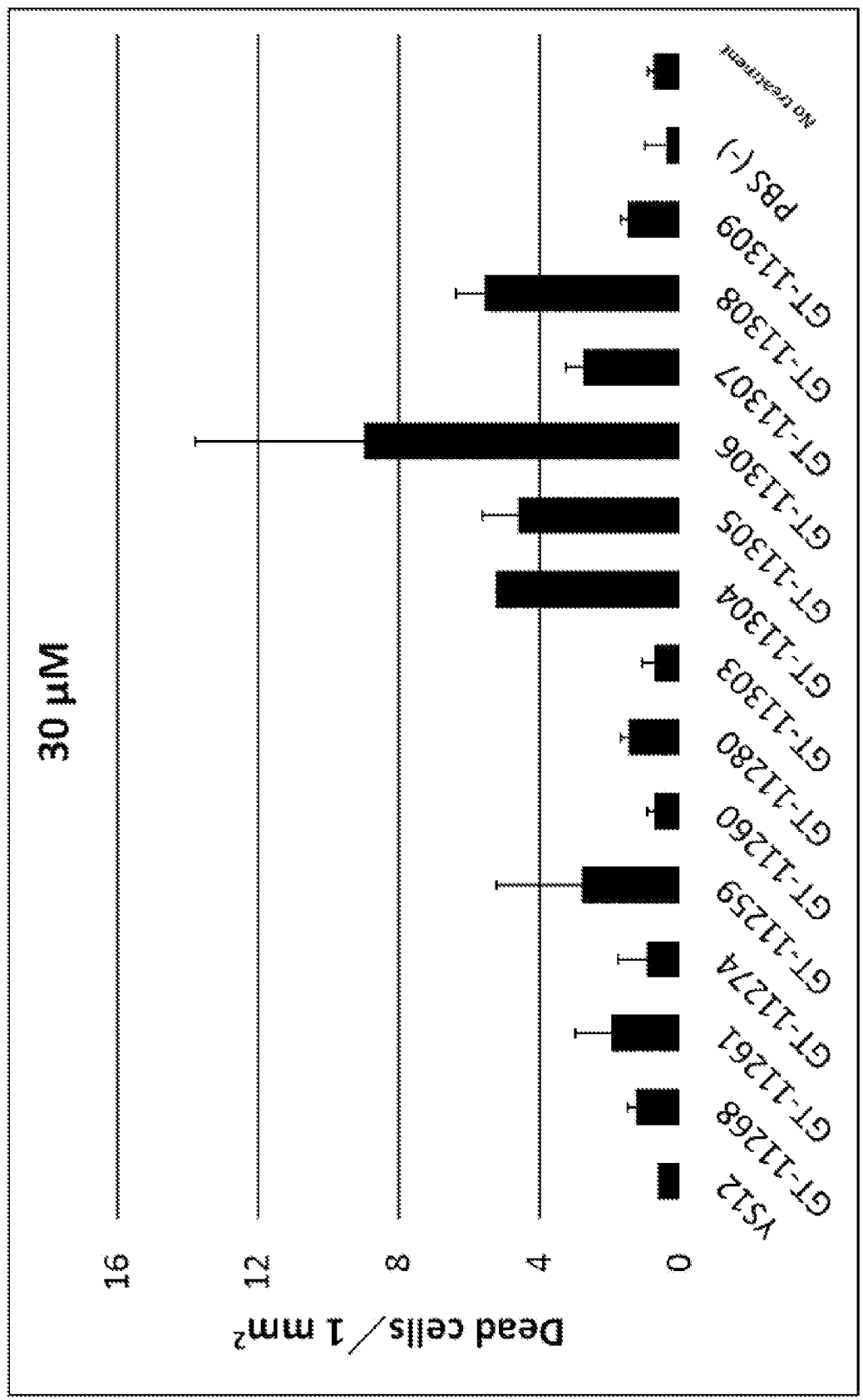
FIG. 36 shows the human liver cancer derived HepG2 cell killing effect at a concentration of 30 μM of each peptide in Example 2. The horizontal axis indicates treatment with YS12, GT-11268, GT-11261, GT-11274, GT-11259, GT-11260, GT-11280, GT-11303, GT-11304, GT-11305, GT-11306, GT-11307, GT-11308, GT-11309, and PBS(−) and no treatment. The vertical axis indicates the mean and the standard deviation (when n=3) of the number of dead cells observed within a 1 mm$^2$ section.
Figure 37:
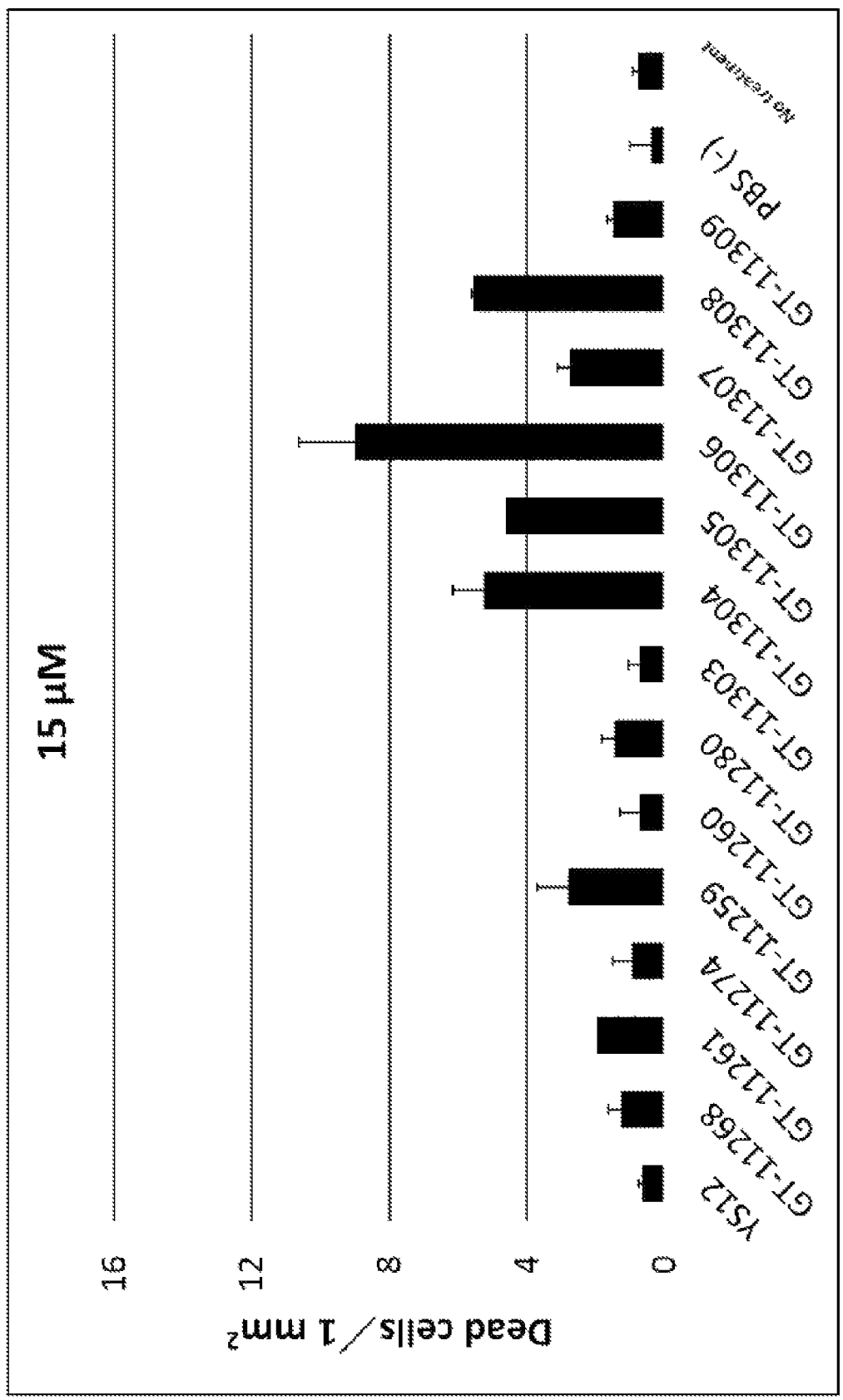
FIG. 37 shows the human liver cancer derived HepG2 cell killing effect at a concentration of 15 μM of each peptide in Example 2. The horizontal axis indicates treatment with YS12, GT-11268, GT-11261, GT-11274, GT-11259, GT-11260, GT-11280, GT-11303, GT-11304, GT-11305, GT-11306, GT-11307, GT-11308, GT-11309, and PBS(−) and no treatment. The vertical axis indicates the mean and the standard deviation (when n=3) of the number of dead cells observed within a 1 mm$^2$ section.

The present disclosure is described while showing the best mode of the disclosure. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

Definitions

The definitions of the terms and/or the detailed basic technology that are particularly used herein are described hereinafter as appropriate.

As used herein, "peptide" is used in the conventional meaning in the art, referring to a compound that is a polymer of a plurality of amino acids linked by a peptide bond and a modified form thereof. When a peptide sequence is described herein, the N-terminus (amino terminus) is positioned on the left, and the C-terminus (carboxy terminus) is positioned on the right, unless specifically noted otherwise. For example, in a peptide represented by a sequence of AGTCI (SEQ ID NO: 43) (alanine-glycine-threonine-cysteine-isoleucine), an amino acid of alanine is free, a carboxyl group of alanine is forming a peptide bond with an amino group of glycine, an amino group of isoleucine is forming a peptide bond with a carboxyl group of cysteine, and a carboxyl group of isoleucine is free. The presence of a chemical group at the end of the sequence of a peptide indicates that an amino group or carboxyl group of the terminal amino acid of the peptide sequence is forming a bond with the chemical group. For example, in the structure $CH_3$—CO—SCHFGPLTWVCK-$NH_2$ (SEQ ID NO: 9), an amino group of serine at the N-terminus is forming a bond with a $CH_3$—CO— group, and a carboxyl group of lysine at the C-terminus is forming a bond with an —$NH_2$ group. Examples of modification include, but are not limited to, acetylation, alkylation (e.g., methylation), halogen (e.g., fluoro, chloro)-substituted alkylation (e.g., fluoromethylation), alkoxylation (e.g., methoxylation), hydroxylation, halogenation, benzothiazolylation, dicyclization (naphthylation), and heterocyclization (e.g., quinolination).

As used herein, "erythropoietin" is used in the conventional meaning of the art, referring to a glycoprotein hormone with a molecular weight of 34,000 to 46,000 that acts on erythroid stem cells (progenitor cells) and stimulates differentiation induction to promote production of red blood cells. As used herein, erythropoietin can also be denoted as EPO or Epo.

As used herein, "erythropoietin receptor" is used in the conventional meaning in the art, referring to a receptor that binds to an erythropoietin. The receptor is expressed on bone marrow cells, white blood cells, and peripheral/central nerves in addition to red blood cells. When EPO binds to an erythropoietin receptor on a red blood cell, Janus kinase 2 (JAK2) is activated. An erythropoietin receptor can also be denoted herein as EpoR.

As used herein, "alkyl group", alone or as a part of another group, refers to a linear or branched saturated hydrocarbyl group with a carbon atom. An alkyl group typically can have 1 to 10 carbon atoms. In some embodiments, an alkyl group can have 1 to 8 carbon atoms, 1 to 6 carbon atoms, 1 to 4 carbon atoms, or 1 to 3 carbon atoms. Examples of $C_{1-3}$ alkyl group include methyl groups, ethyl groups, propyl groups, and isopropyl groups. Examples of $C_{1-4}$ alkyl group include the aforementioned $C_{1-3}$ alkyl groups, as well as butyl groups, isobutyl groups, sec-butyl groups, and tert-butyl groups. Examples of $C_{1-6}$ alkyl group include the aforementioned $C_{1-4}$ alkyl groups, as well as pentyl groups, isopentyl groups, neopentyl groups, hexyl groups, and the like. Additional examples of alkyl groups include heptyl groups, octyl groups, and the like.

As used herein, "alkylene group" is a divalent group generated by further removing one hydrogen from an "alkyl group". Specific examples of alkylene group include, but are not limited to, —$CH_2$—, —$CH_2CH_2$—, —$(CH_2)_3$—, —$CH_2CH(CH_3)$—, —$(CH_2)_4$—, —$CH_2CH_2CH(CH_3)$—, —$CH_2CH(CH_3)$ $CH_2$—, —$(CH_2)_5$—, —$CH_2CH_2CH_2CH(CH_3)$—, —$CH_2CH_2CH(CH_3)$ $CH_2$—, —$(CH_2)_6$—, —$(CH_2)_7$—, —$(CH_2)_8$—, —$(CH_2)_9$—, —$(CH_2)_{10}$—, and the like.

As used herein, "alkenyl group", alone or as a part of another group, refers to a linear or branched hydrocarbyl group having a carbon atom and one or more carbon-carbon double bonds. An alkenyl group can typically have 2 to 10 carbon atoms. In some embodiments, an alkenyl group can have 2 to 8 carbon atoms, 2 to 6 carbon atoms, or 2 to 4 carbon atoms. One or more carbon-carbon double bonds can be inside (e.g., double bond in 2-butenyl) or at a terminus (e.g., double bond in 1-butenyl). Examples of $C_{2-4}$ alkenyl group include ethenyl groups (vinyl groups), 1-propenyl groups, 2-propenyl groups, 1-butenyl groups, 2-butenyl groups, butadienyl groups, and the like. Examples of $C_{2-6}$ alkenyl group include the aforementioned $C_{2-4}$ alkenyl group, as well as pentenyl groups, pentadienyl groups, hexenyl groups, and the like. Additional examples of alkenyl group include heptenyl groups, octenyl groups, octatrienyl groups, and the like.

As used herein, "alkenylene group" is a divalent group generated by further removing one hydrogen from "alkenyl group". Specific examples of alkenylene group include, but are not limited to, —CH=CH—, —CH=CH—CH$_2$—, —CH=CH—(CH$_2$)$_2$—, —CH$_2$—CH=CH—CH$_2$—, —CH=C(CH$_3$)—CH$_2$—, —CH=CH—CH=CH—, —CH=CH—(CH$_2$)$_3$—, —CH=CH—CH=CH—CH$_2$—, —CH=CH—(CH$_2$)$_4$—, —CH=CH—(CH$_2$)$_5$—, —CH=CH—(CH$_2$)$_6$—, —CH=CH—(CH$_2$)$_7$—, —CH=CH—(CH$_2$)$_8$—, and the like.

As used herein, "alkoxyl group" is a monovalent group of —O-alkyl. Preferred examples of alkoxyl group include $C_{1-6}$ alkoxyl groups (i.e., $C_{1-6}$ alkyl-O—), $C_{1-4}$ alkoxyl groups (i.e., $C_{1-4}$ alkyl-O—), and the like. Specific examples of $C_{1-4}$ alkoxyl group include methoxyl groups (CH$_3$O—), ethoxyl groups (CH$_3$CH$_2$O—), n-propoxyl groups (CH$_3$(CH$_2$)$_2$O—), isopropoxyl groups ((CH$_3$)$_2$CHO—), n-butoxyl groups (CH$_3$(CH$_2$)$_3$O—), isobutoxyl groups ((CH$_3$)$_2$CHCH$_2$O—), tert-butoxyl groups ((CH$_3$)$_3$CO—), sec-butoxyl groups (CH$_3$CH$_2$CH(CH$_3$)O—), and the like. Specific examples of $C_{1-6}$ alkoxyl group include, but are not limited to, $C_{1-4}$ alkoxyl groups, n-pentyloxyl groups (CH$_3$(CH$_2$)$_4$O—), isopentyloxyl groups ((CH$_3$)$_2$CHCH$_2$CH$_2$O—), neopentyloxyl groups ((CH$_3$)$_3$CCH$_2$O-tert-pentyloxyl groups (CH$_3$CH$_2$C(CH$_3$)$_2$O—), 1,2-dimethylpropoxyl groups (CH$_3$CH(CH$_3$)CH(CH$_3$)O—), and the like.

As used herein, "aliphatic group" refers to an alkyl group, alkenyl group, and alkynyl group, and does not include cyclic hydrocarbon groups.

As used herein, "heteroaliphatic group" refers to an aliphatic group in which one part thereof is substituted with a heteroatom (e.g., nitrogen atom, oxygen atom, sulfur atom, or the like).

As used herein, the term "aryl group" refers to a single aromatic ring or a fused polycyclic system wherein at least one of the rings is aromatic and all atoms in the ring are carbon. For example, an aryl group can have 6 to 26 carbon atoms (6 to 26 members), 6 to 20 carbon atoms (6 to 20 members), 6 to 14 carbon atoms (6 to 14 members), or 6 to 12 carbon atoms (6 to 12 members). An aryl group includes a phenyl group. An aryl group includes a fused polycyclic system (e.g., cyclic system comprising 2, 3, or 4 rings) with 8 to 20 carbon atoms, wherein at least one ring is aromatic, but other rings may or may not be aromatic. Such a fused polycyclic system is optionally substituted with one or more (e.g., 1, 2, or 3) oxo groups at any carbocyclic moiety of the fused polycyclic system. Rings in a fused polycyclic system can be connected to one another via fusion, spiro, or crosslinking bond if permitted by the valency requirement. Typical examples of aryl group include, but are not limited to, phenyl groups, indenyl groups, naphthyl groups, 1,2,3,4-tetrahydronaphthyl groups, anthryl groups, pyrenyl groups, and the like.

As used herein, the term "heteroaryl group" refers to a single aromatic ring or fused polycyclic system having at least one heteroatom in a ring. The heteroatom is selected from the group consisting of oxygen, nitrogen, and sulfur. A heteroaryl group can be typically 5- to 26-membered. In some embodiments, a heteroaryl group can be 5- to 20-membered, 5- to 14-membered, 5- to 12-membered, or 5- to 10-membered. A heteroaryl group encompasses a single aromatic ring having about 1 to 6 carbon atoms and about 1 to 4 heteroatoms selected from the group consisting of oxygen, nitrogen, and sulfur in a ring. Examples of such a ring include, but are not limited to, pyridyl groups, pyrimidinyl groups, pyradinyl groups, oxazolyl groups, furyl groups, and the like. Sulfur and nitrogen atoms can also be in an oxidized form if a ring is aromatic. A heteroaryl group also encompasses fused polycyclic systems (e.g., cyclic systems comprising 2, 3, or 4 rings) in which a previously defined heteroaryl group can form a fused polycyclic system by fusing with one or more rings selected from heteroaryl (e.g., forming naphthyridinyl such as 1,8-naphthyridinyl), heterocycle (e.g., forming 1,2,3,4-tetrahydronaphthyridinyl such as 1,2,3,4-tetrahydro-1,8-naphthyridinyl), carbocycle (e.g., forming 5,6,7,8-tetrahydroquinolyl), and aryl (e.g., forming indazolyl). In some embodiments, a heteroaryl group (single aromatic ring or fused polycyclic system) has about 1 to 20 carbon atoms and about 1 to 6 heteroatoms in a heteroaryl ring. Such a fused polycyclic system is optionally substituted with one or more (e.g., 1, 2, 3 or 4) oxo groups at a carbocyclic or heterocyclic moiety of the fused ring. Rings in a fused polycyclic system can be connected to one another via fusion, spiro, or crosslinking bond if permitted by the valency requirement. It is understood that individual rings in a fused polycyclic system can be bound to one another in any order. It is understood that a position of a bond in the fused polycyclic system described above can be at any position of the fused polycyclic system including the heteroaryl, heterocycle, aryl, or carbocyclic moiety of the fused polycyclic system, and any suitable atom of the fused polycyclic system including a carbon atom and heteroatom (e.g., nitrogen). Examples of heteroaryl group include, but are not limited to, quinolyl groups, benzothiazolyl groups, pyridyl groups, pyrrolyl groups, pyradinyl groups, pyrimidinyl groups, pyridazinyl groups, pyrazolyl groups, thienyl groups, indolyl groups, imidazolyl groups, oxazolyl groups, isooxazolyl groups, thiazolyl groups, furyl groups, oxadiazolyl groups, thiadiazolyl groups, isoquinolyl groups, benzooxazolyl groups, indazolyl groups, quinoxalyl groups, quinazolyl groups, 5,6,7,8-tetrahydroisoquinolinyl benzofuranyl groups, benzoimidazolyl groups, thianaphthenyl groups, pyrrolo[2,3-b]pyridinyl groups, quinazolinyl-4(3H)-one groups, triazolyl groups, 4,5,6,7-tetrahydro-1H-indazole groups, 3b,4,4a,5-tetrahydro-1H-cyclopropa[3,4]cyclopenta[1,2-c]pyrazole groups, and the like.

As used herein, "halo" or "halogen", alone or as a part of another group, refers to fluorine (fluoro), chlorine (chloro), bromine (bromo), or iodine (iodo), unless specifically noted otherwise.

As used herein, "haloalkyl group", alone or as a part of another group, refers to an alkyl group with one or more hydrogen atoms each independently substituted with halo, unless specifically noted otherwise. Examples of haloalkyl group include —CCl$_3$, —CFCl$_2$, —CF$_2$Cl, —CCl$_2$CCl$_3$, —CH$_2$F, —CHF$_2$, —CH$_2$Cl, —CH$_2$Br, —CH(Cl) CH$_2$Br, —CH$_2$CH(F) CH$_2$Cl, and the like. A "haloalkenyl group", "haloalkynyl group", "haloaliphatic group", and the like are also defined in the same manner as the aforementioned "haloalkyl group".

As used herein, "carbocycle" or "carbocyclic group", alone or as a part of another group, refers to a monocyclic, bicyclic, or tricyclic hydrocarbon group, or polycyclic hydrocarbon group with more rings, which is completely saturated or comprises one or more unsaturated units but is not aromatic. In one embodiment, a carbocyclic group can be a monocyclic $C_{3-9}$ hydrocarbon group, bicyclic $C_{8-12}$ hydrocarbon group, or tricyclic $C_{10-16}$ hydrocarbon group. Any individual ring in the carbocyclic group described above can have 3 to 7 ring atoms. Examples of carbocyclic group include, but are not limited to, cycloalkyl groups such as cyclopropyl groups, cyclobutyl groups, cyclopentyl groups, cyclohexyl groups, cycloheptyl groups, cyclooctyl groups, and cyclononyl groups, cycloalkenyl groups such as cyclopropenyl groups, cyclobutenyl groups, cyclopentenyl groups, cyclohexenyl groups, cycloheptenyl groups, cyclooctenyl groups, and cyclononenyl groups, cycloalkynyl groups such as cyclopropynyl groups, cyclobutynyl groups, cyclopentynyl groups, cyclohexynyl groups, cycloheptynyl groups, cyclooctynyl groups, and cyclononynyl groups, adamantyl groups, and the like. In a carbocyclic group, one of the atoms in the ring can be bound to the rest of the portions of the molecule when possible.

As used herein, "heterocycle" or "heterocyclic group", alone or as a part of another group, refers to a monocyclic, bicyclic, or tricyclic system, or polycyclic system with more groups, which is completely saturated or comprises one or more unsaturated units but is not aromatic, wherein at least one ring in the cyclic system comprises one or more same or different heteroatoms. In some embodiments, a "heterocycle" or "heterocyclic group" has 3 to 14 ring atoms, wherein one or more ring atoms are heteroatoms independently selected from oxygen, sulfur, nitrogen, or phosphorous, and each ring in the cyclic system comprises 3 to 8 ring atoms.

Examples of heterocyclic group include, but are not limited to, monocycles such as 2-tetrahydrofuranyl groups, 3-tetrahydrofuranyl groups, 2-tetrahydrothiophenyl groups, 3-tetrahydrothiophenyl groups, 2-morpholino groups, 3-morpholino groups, 4-morpholino groups, 2-thiomorpholino groups, 3-thiomorpholino groups, 4-thiomorpholino groups, 1-pyrrolidinyl groups, 2-pyrrolidinyl groups, 3-pyrrolidinyl groups, 1-tetrahydropiperazinyl groups, 2-tetrahydropiperazinyl groups, 3-tetrahydropiperazinyl groups, 1-piperidinyl groups, 2-piperidinyl groups, 3-piperidinyl groups, 1-pyrazolinyl groups, 3-pyrazolinyl groups, 4-pyrazolinyl groups, 5-pyrazolinyl groups, 1-piperidinyl groups, 2-piperidinyl groups, 3-piperidinyl groups, 4-piperidinyl groups, 2-thiazolidinyl groups, 3-thiazolidinyl groups, 4-thiazolidinyl groups, 1-imidazolidinyl groups, 2-imidazolidinyl groups, 4-imidazolidinyl groups, and 5-imidazolidinyl groups, and bicycles such as 3-1H-benzoimidazol-2-one groups, 3-(1-alkyl)-benzoimidazol-2-one groups, indolinyl groups, tetrahydroquinolinyl groups, tetrahydroisoquinolinyl groups, benzothiolane groups, benzodithian groups, and 1,3-dihydro-imidazol-2-one groups. In a heterocyclic group, one of the atoms in the ring can be bound to the rest of the portions of the molecule when possible.

As used herein, the term "unsaturated" means that a certain portion has one or more unsaturated units.

A "heteroaliphatic group", "heterocycle", "heterocyclic group", "heteroaryl group", or "arylene group", when substituted, can have a substituent on a heteroatom if substitutable.

If a group is "substituted", at least one hydrogen in the group is replaced with a group (substituent) other than hydrogen. The number of substituents thereof is not particularly limited, if substitutable, and is one or more. The descriptions for each group are also applicable when the group is a part of another group or a substituent thereof, unless specifically noted otherwise. If, for example, a $C_{1-6}$ alkyl group is substituted with a certain substituent, the number of carbons of the substituent is not included in the number of carbons of the alkyl group. The same applies to other groups.

As used herein, "amino acid" is used in the conventional meaning in the art, referring to a compound having a carboxyl group and amino group within a single molecule. Typically, an amino acid is an α amino acid, but an amino acid herein can also be an amino acid with a greater distance between a carboxyl group and amino group, such as a R amino acid and y amino acid. Furthermore, an amino acid herein indicates an L enantiomer unless specifically noted otherwise. If an amino acid is a D enantiomer, D (or d) is appended in the front (e.g., D-Ala (or d-Ala)) or is indicated with a lower case alphabet (e.g., a). Representative examples of amino acids are provided below, but other amino acids are also intended herein.

TABLE 1

Representative amino acids

| Three letter code | One letter code | Name of amino acid |
|---|---|---|
| Gly | G | Glycine |
| Ala | A | Alanine |
| Val | V | Valine |
| Leu | L | Leucine |
| Ile | I | Isoleucine |
| Ser | S | Serine |
| Thr | T | Threonine |
| Met | M | Methionine |
| Cys | C | Cysteine |
| Phe | F | Phenylalanine |
| Tyr | T | Tyrosine |
| Trp | W | Tryptophan |
| His | H | Histidine |
| Lys | K | Lysine |
| Arg | R | Arginine |
| Glu | E | Glutamic acid |
| Asp | D | Aspartic acid |
| Gln | Q | Glutamine |
| Asn | N | Asparagine |
| Pro | P | Proline |

Exemplary amino acids other than those described in Table 1 include, but are not limited to, homoproline, phenylglycine, phenethylglycine, ax-naphthylalanine, R3-naphthylalanine, P3-homotryptophan, quinolylalanine, homocysteine, penicillamine, sarcosine, ornithine, citrulline, hydroxyproline, modified forms of the naturally-occurring amino acids described above (modified amino acids), and modified forms of non-naturally-occurring amino acids (modified amino acids).

TABLE 2

Examples of amino acids other than the 20 representative natural amino acids

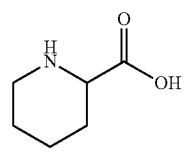

Homoproline

TABLE 2-continued

Examples of amino acids other than the 20 representative natural amino acids

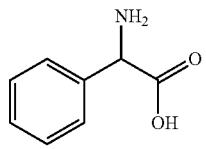

Phenylglycine

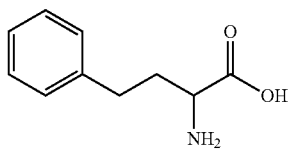

Phenethylglycine

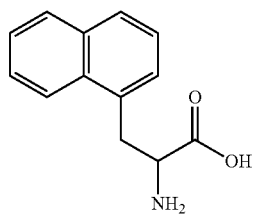

α-naphthylalanine

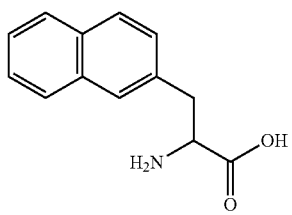

β-naphthylalanine

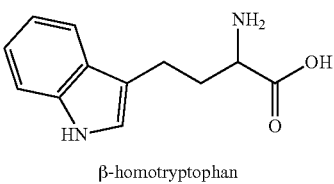 [SMILES: NC(CCc1c[nH]c2ccccc12)C(=O)O]

β-homotryptophan

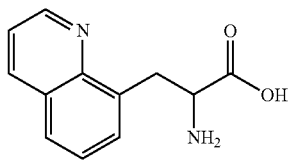

8-quinolylalanine

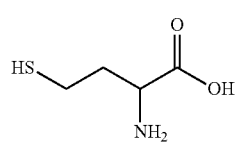

Homocysteine

TABLE 2-continued

Examples of amino acids other than the 20 representative natural amino acids

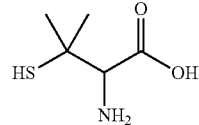

Penicillamine

Examples of additional amino acids include the following modified amino acids.

NH₂—CH(R')—COOH [wherein R' has a structure of (a bond or a linear or branched alkylene group or alkenylene group (e.g., $C_{1-5}$))-(an aryl group or heteroaryl group (e.g., 5- to 18-membered ring, and/or monocyclic, bicyclic, or tricyclic) optionally substituted with a substituent selected from the group consisting of a linear or branched alkyl group (e.g., $C_{1-3}$) optionally substituted with a halogen atom, a linear or branched methoxyl group (e.g., $C_{1-3}$) optionally substituted with a halogen atom, a halogen atom, and a hydroxyl group)]

NH₂—CH(R')—COOH [wherein R' is—(a linear or branched alkyl group or alkenyl group (e.g., $C_{1-5}$))]

[Chemical Formula 1]

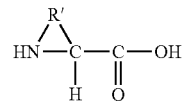

wherein R' is a linear or branched alkylene group or alkenylene group (e.g., $C_3$-8)

NH₂—CH(R')—COOH [wherein R' is—(a linear or branched alkyl group or alkenyl group (e.g., $C_{1-8}$), wherein any one of the carbon atoms in the alkyl group or alkenyl group is optionally substituted with a sulfur atom, and may further have —SH]

NH₂—CH(R')—COOH [wherein R' is—(a linear or branched alkyl group or alkenyl group (e.g., $C_{1-10}$)), wherein any 1, 2, or 3 carbon atoms are optionally substituted with nitrogen atoms]

As used herein, "conservative substitution" refers to a substitution of an amino acid in a peptide with another amino acid with a similar property. The property of the peptide can be expected to be similar before and after a conservative substitution.

In one embodiment, a conservative substitution is a substitution of an amino acid in the following groups of amino acids with an amino acid within the same group.

Group 1: glycine, alanine, valine, leucine, and isoleucine

Group 2: serine and threonine

Group 3: phenylalanine, tyrosine, tryptophan, homotryptophan, phenylglycine, phenethylglycine, benzothiazolylalanine, α-naphthylalanine, β-naphthylalanine, quinolylalanine, pyridylalanine, benzopyrazolylalanine, and amino acids with one or two hydrogen atoms on the aromatic ring thereof replaced with a methyl group, methoxyl group, hydroxyl group, or halogen atom Group 4: lysine, arginine, histidine, and ornithine Group 5: cysteine, methionine, homocysteine, and penicillamine Group 6: proline and homoproline Group 7: glutamic acid and aspartic acid Group 8: glutamine and asparagine In one embodiment, a conservative substitution is a substitution with an amino acid including any modification among the followings: removal of any one of the —CH$_2$- moieties in the original amino acid, addition of a —CH$_2$— or —CH$_3$ moiety to any one portion of the amino acid, substitution of any one of the hydrogen atoms of the original amino acid with an alkyl group (e.g., methyl group), alkoxyl group (e.g., methoxyl group), hydroxyl group, or halogen atom, fusion or expansion of a ring by removal or addition of one carbon atom at any position of an aromatic ring in the original amino acid.

The peptide of the present disclosure or a salt or solvate thereof, or a prodrug thereof including a conservative substitution can also retain one or more characteristics from efficacy such as EpoR inhibiting capability, cancer cell killing capability, reduction of normal cell killing capability, cancer cell killing capability at a low dosing frequency or the like, side effects, ability to migrate to a specific site, absorption/distribution/metabolism/excretion kinetics, bioavailability, and stability, in the same manner as the original peptide.

As used herein, "disulfide bond" for a peptide refers to an S—S bond formed within a single peptide molecule. Typically, a disulfide bond is formed between sulfur atoms that are present each in the two cysteine residues, but a bond between any sulfur atoms that are present within a peptide molecule is referred to as a disulfide bond herein. In one embodiment, a disulfide bond within a peptide molecule is formed between sulfur atoms that are present on a side chain of a peptide.

As used herein, "drug component" refers to any component that can be a constituent of a drug. Examples thereof include an active ingredient (component itself exhibiting efficacy), additive (component that is not expected to have efficacy in itself, but is expected to serve a certain role (e.g., excipient, lubricating agent, surfactant, or the like) when contained in a drug), adjuvant (enhances the efficacy of the active ingredient), and the like. A drug component can be an independent substance, or a combination of a plurality of substances or agents. A drug component can also encompass any combination such as a combination of an active ingredient and an additive, and a combination of an adjuvant and an active ingredient.

As used herein, "active ingredient" refers to a component that exerts the intended efficacy. An individual or a plurality of components can fall under an active ingredient.

As used herein, "additive" refers to any component that is not expected to have efficacy, but serves a certain role when contained in a drug. Examples thereof include pharmaceutically acceptable carriers, diluents, excipients, buffering agents, binding agents, blasting agents, diluents, flavoring agents, and lubricants.

A drug component used herein can be a purified component. The term "purified" as used herein refers to the presence of preferably at least 75% by weight, more preferably at least 85% by weight, still more preferably at least 95% by weight, and most preferably at least 98% by weight of the same type of biological agent.

As used herein, "subject" refers to an entity which is to be subjected to treatment or the like in the present disclosure.

As used herein, an "agent" is used in a broad sense, and may be any substance or other elements (e.g., energy such as light, radiation, heat, and electricity) as long as the intended object can be achieved. Examples of such a substance include, but are not limited to, proteins, polypeptides, oligopeptides, peptides, polynucleotides, oligonucleotides, nucleotides, nucleic acids (e.g., including DNA such as cDNA and genomic DNA, and RNA such as mRNA), polysaccharides, oligosaccharides, lipids, organic small molecules (e.g., hormones, ligands, information transmitting substances, organic small molecules, molecules synthesized by combinatorial chemistry, small molecules which can be utilized as a pharmaceutical product (e.g., a low molecular weight ligand), and the like), and composite molecules thereof.

As used herein, "treat (treatment or treating)" refers to the prevention of exacerbation, preferably maintaining of the current condition, more preferably alleviation, and still more preferably disappearance of a condition or disorder in case of such a condition or disorder, including being capable of exerting an effect of improving or preventing a condition of a patient or one or more symptoms accompanying the condition. Preliminary diagnosis with suitable therapy is referred to as "companion therapy" and a diagnostic agent therefor may be referred to as "companion diagnostic agent".

As used herein, "therapeutic drug (agent)" broadly refers to any agent that can treat a condition of interest. In one embodiment of the present disclosure, "therapeutic drug" can be a pharmaceutical composition comprising an active ingredient and one or more pharmaceutically acceptable carriers. A pharmaceutical composition can be manufactured by any method that is known in the technical field of pharmaceutical science, for example, by mixing an active ingredient with the carrier described above. The mode of use of a therapeutic drug is not limited, as long as the drug can be used for treatment. A therapeutic drug can be an active ingredient alone, or a mixture of an active ingredient with any component. The form of the carrier described above is not limited. Examples thereof include solids and liquids (e.g., buffer).

As used herein, "prevention" or "prophylaxis" refers to the action of taking a measure against a disease or disorder from being in such a condition prior to being in such a condition. It is possible to use the agent of the present disclosure to perform diagnosis, and if necessary use the agent of the present disclosure to prevent or take measures to prevent the disease or disorder.

As used herein, "prophylactic drug (agent)" broadly refers to any agent capable of preventing a condition of interest.

As used herein, "kit" refers to a unit providing parts to be provided (e.g., test drug, diagnostic drug, therapeutic drug, label, user manual, and the like) which are generally separated into two or more segments. Such a kit form is preferred when providing a composition, which should not be provided in a mixed state for stability or the like and is preferably used by mixing immediately prior to use. Such a kit advantageously comprises an instruction or user manual describing how the provided parts (e.g., test drug, diagnostic drug, and therapeutic drug) are used or how the reagent should be processed.

As used herein, "instruction" is a document with an explanation of the method of use of the present disclosure for a physician or other users. The instruction has an instructive description for administration of a drug of the present disclosure or the like. Further, an instruction may have a description instructing the administering manner (e.g., by oral administration, injection, or the like). The instruction is prepared in accordance with a format specified by the regulatory agency of the country in which the present disclosure is practiced (e.g., the Ministry of Health, Labour and Welfare in Japan, Food and Drug Administration (FDA) in the U.S. or the like), with an explicit description showing approval by the regulatory agency. The instruction is a so-called package insert and is typically provided in, but not limited to, paper media. The instructions may also be provided in a form such as electronic media (e.g., web sites provided on the Internet or emails).

As used herein, "diagnosis" refers to identifying various parameters associated with a disease, disorder, condition, or the like in a subject to determine the current or future state of such a disease, disorder, or condition. As used herein, "diagnosis" when narrowly defined refers to diagnosis of the current state, but when broadly defined includes "early diagnosis", "predictive diagnosis", "prediagnosis", and the like.

A procedure of formulation as a drug or the like of the present disclosure is known in the art and is described, for example, in the Japanese Pharmacopoeia, U.S. Pharmacopoeia, and other countries' pharmacopoeias. Thus, those skilled in the art can determine the amount to be used from the descriptions herein without undue experimentation.

DESCRIPTION OF PREFERRED EMBODIMENTS

Preferred embodiments of the present disclosure are described below. Embodiments described below are provided to facilitate the understanding of the present disclosure. It is understood that the scope of the present disclosure should not be limited to the following descriptions. Thus, it is apparent that those skilled in the art can make appropriate modifications within the scope of the present disclosure by referring to the descriptions herein. Those skilled in the art can appropriately combine any of the embodiments.

<Structure of Anti-EpoR Peptide>

In one aspect, the present disclosure provides an anti-EpoR peptide. In a specific embodiment, the peptide of the present disclosure has one or more improved characteristics compared to $CH_3$—CO—SCHFGPLTWVCK-$NH_2$ (SEQ ID NO: 9). Examples of such a characteristic include, but are not limited to, efficacy such as EpoR inhibiting capability, cancer cell killing capability, reduction in normal cell killing capability, cancer cell killing capability at a low dosing frequency or the like, side effects, ability to migrate to a specific site, absorption/distribution/metabolism/excretion kinetics, bioavailability, stability, and the like.

The present disclosure relates to a modified peptide based on $CH_3$-CO-SCHFGPLTWVCK-$NH_2$ (SEQ ID NO: 9). A modified peptide can be a modified peptide based on a peptide having the basic structure of -[SCHFGPLTWVCK]- (SEQ ID NO: 2) or a prodrug thereof or a salt thereof. For example, such a modified peptide or a prodrug thereof or a salt thereof comprises at least one modification at any part (including an amino terminus and carboxy terminus) of $CH_3$-CO-SCHFGPLTWVCK-$NH_2$ (SEQ ID NO: 9), and preferably comprises 2 modifications, 3 modifications, or 4 modifications, or modification on a modification. In a preferred embodiment, the peptide of the present disclosure comprises a modification at 1, 2, 3, or all of the portions corresponding to an amino terminus, carboxy terminus, F, and W in $CH_3$-CO-SCHFGPLTWVCK-$NH_2$ (SEQ ID NO: 9).

In another aspect, the anti-EpoR peptide of the present disclosure has a structure represented by the following formula (I).

Formula (I):
(SEQ ID NO: 1)
$X^1$-SCH($A^1$)($A^2$)($A^3$)($A^4$)($A^5$)($A^6$)V($A^7$)($A^8$)-$X^2$, wherein $X^1$ is an amino terminus side of the peptide, and $X^2$ is a carboxy terminus side of the peptide.

In one embodiment of formula (I), $A^1$ is —NH—CH($R^{A1}$)—CO—, wherein $R^{A1}$ has a structure of—(a bond, or a linear or branched alkylene group or alkenylene group)— (an aryl group or a heteroaryl group optionally substituted with a substituent selected from the group consisting of a linear or branched alkyl group optionally substituted with a halogen atom, a linear or branched methoxyl group optionally substituted with a halogen atom, a halogen atom, and a hydroxyl group). In one embodiment of formula (I), $A^1$ is —NH—CH($R^{A1}$)—CO—, wherein $R^{A1}$ has a structure of (a bond or a linear or branched $C_{1-5}$ alkylene group or alkenylene group)—(a 5- to 18-membered monocyclic, bicyclic, or tricyclic aryl group or heteroaryl group optionally substituted with a substituent selected from the group consisting of a linear or branched $C_{1-3}$ alkyl group optionally substituted with a halogen atom, a linear or branched $C_{1-3}$ alkoxyl group optionally substituted with a halogen atom, a halogen atom, and a hydroxyl group), wherein any number of the substituents may be present on an aryl group or heteroaryl group at any position. In one embodiment of formula (I), $A^1$ is —NH—CH($R^{A1}$)—CO—, wherein $R^{A1}$ is (a bond or a linear or branched $C_{1-3}$ alkylene group)-(a monocyclic or bicyclic aryl group or heteroaryl group (e.g., benzene, naphthalene, pyridine, thiophene, or benzothiophene) optionally substituted with a substituent selected from the group consisting of a linear or branched $C_{1-3}$ alkyl group (e.g., methyl group), a linear or branched $C_{1-3}$ alkoxyl group (e.g., methoxyl group), a halogen atom, and a hydroxyl group). In one embodiment of formula (I), $A^1$ is Met, or Phe, Tyr, phenylglycine, or phenethylglycine optionally substituted with a methyl group, a methoxyl group, a halogen atom, or a hydroxyl group, wherein any number of methyl groups, methoxyl groups, halogen atoms, or hydroxyl groups may be present on an aromatic ring at any position. In one embodiment of formula (I), a methyl group, methoxyl group, halogen atom, or hydroxyl group on an aromatic ring in $A^1$ may be present at a meta position (m–), para position (p–) or a combination thereof (3,4-). In one embodiment of formula (I), $A^1$ is Phe, Tyr, p-fluoro-Phe, p-chloro-Phe, m-chloro-Phe, 3,4-difluoro-Phe, phenylglycine, or phenethylglycine. Although not wishing to be bound by any theory, it is understood that the residue of $A^1$ is possibly present at a position corresponding to the lipophilic pocket of EpoR when an anti-EpoR peptide binds to the EpoR. Relatively high activity was observed when $A^1$ was p-fluoro-Phe, Tyr, phenethylglycine, or chloro-substituted Phe in an anti-EpoR peptide. A hydrogen bond is possibly formed between the residue of $A^1$ and EpoR. An anti-EpoR peptide having $A^1$ with a structure within the scope described above is expected to highly retain at least one characteristic from efficacy such as EpoR inhibiting capability, cancer cell killing capability, reduction in normal cell killing capability, cancer cell killing capability at a low dosing frequency or the like, side effects, ability to migrate to a specific site, absorption/distribution/metabolism/excretion kinetics, bioavailability, and stability.

In one embodiment of formula (I), $A^2$ is —NH—CH($R^{42}$)—CO—, wherein $R^{42}$ is —(H or a linear or branched $C_{1-5}$ alkyl group or alkenyl group). In one embodiment of formula (I), $A^2$ is Ala, D-Ala, or Gly. An anti-EpoR peptide having $A^2$ with a structure within the scope described above is expected to highly retain at least one characteristic from efficacy such as EpoR inhibiting capability, cancer cell killing capability, reduction in normal cell killing capability, cancer cell killing capability at a low dosing frequency or the like, side effects, ability to migrate to a specific site, absorption/distribution/metabolism/excretion kinetics, bioavailability, and stability.

In one embodiment of formula (I), $A^3$ is —NH—CH($R^{43}$)—CO—, wherein $R^{43}$ is —(H or a linear or branched $C_{1-5}$ alkyl group or alkenyl group). In one embodiment of formula (I), $A^3$ is

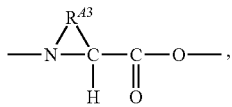

[Chemical Formula 2]

wherein $R^{43}$ is a linear or branched $C_{3-8}$ alkylene group or alkenylene group. In one embodiment of formula (I), $A^3$ is Pro, homoproline, or Ala. An anti-EpoR peptide having $A^3$ with a structure within the scope described above is expected to highly retain at least one characteristic from efficacy such as EpoR inhibiting capability, cancer cell killing capability, reduction in normal cell killing capability, cancer cell killing capability at a low dosing frequency or the like, side effects, ability to migrate to a specific site, absorption/distribution/metabolism/excretion kinetics, bioavailability, and stability. Preferably, the peptide of formula (I) has at least one characteristic that is improved from a peptide having the structure of $CH_3$—CO-SCHFGPLTWVCK-$NH_2$ (SEQ ID NO: 9).

In one embodiment of formula (I), $A^4$ is —NH—CH($R^{44}$)—CO—, wherein $R^{44}$ is —(H or a linear or branched $C_{1-5}$ alkyl group or alkenyl group), wherein one of the carbon atoms in the alkyl group or alkenyl group may be replaced with a sulfur atom in one embodiment. In one embodiment of formula (I), $A^4$ is Met, Leu, Ala, or Ile. In a specific embodiment of formula (I), $A^4$ is Met or Leu. An anti-EpoR peptide having $A^4$ with a structure within the scope described above is expected to highly retain at least one characteristic from efficacy such as EpoR inhibiting capability, cancer cell killing capability, reduction in normal cell killing capability, cancer cell killing capability at a low dosing frequency or the like, side effects, ability to migrate to a specific site, absorption/distribution/metabolism/excretion kinetics, bioavailability, and stability.

In one embodiment of formula (I), $A^5$ is —NH—CH($R^4S$)—CO—, wherein $R^{45}$ is —(H or a linear or branched $C_{1-5}$ alkyl group or alkenyl group), wherein one of the hydrogen atoms in the alkyl group or alkenyl group may be replaced with a hydroxyl group in one embodiment. In one embodiment of formula (I), $A^5$ is Thr or Ala. An anti-EpoR peptide having $A^5$ with a structure within the scope described above is expected to highly retain at least one characteristic from improvement in efficacy such as potent EpoR inhibiting capability, high cancer cell killing capability, low normal cell killing capability, cancer cell killing capability at a low dosing frequency or the like, reduction in side effects, ability to specifically migrate to a specific site, improved absorption/distribution/metabolism/excretion kinetics, improvement in bioavailability, and high stability.

In one embodiment of formula (I), $A^6$ is —NH—CH($R^{46}$)—CO—, wherein $R^{41}$ has a structure of (a bond or a linear or branched alkylene group or alkenylene group)-(an aryl group or heteroaryl group optionally substituted with a substituent selected from the group consisting of a linear or branched alkyl group optionally substituted with a halogen atom, a linear or branched alkoxyl group (e.g., methoxyl group) optionally substituted with a halogen atom, a halogen atom, and a hydroxyl group). In one embodiment of formula (I), $A^6$ is —NH—CH($R^{46}$)—CO—, wherein $R^{46}$ is—(a bond or a linear or branched $C_1$-s alkylene group or alkenylene group)-(a 5- to 18-membered monocyclic, bicyclic, or tricyclic aryl group or heteroaryl group optionally substituted with a substituent selected from the group consisting of a linear or branched $C_{1-3}$ alkyl group optionally substituted with a halogen atom, a linear or branched $C_{1-3}$ alkoxyl group optionally substituted with a halogen atom, a halogen atom, and a hydroxyl group), wherein any number of the substituents may be present on an aryl group or heteroaryl group at any position. In one embodiment of formula (I), $A^6$ is —NH—CH($R^{46}$)—CO—, wherein $R^{46}$ is—(a bond or a linear or branched $C_{1-3}$ alkylene group)-(a 5- to 18-membered monocyclic or bicyclic aryl group or heteroaryl group (e.g., benzene, indole, naphthalene, benzothiazole, and quinoline) optionally substituted with a substituent selected from the group consisting of a linear or branched $C_{1-3}$ alkyl group (e.g., methyl group), a linear or branched $C_{1-3}$ alkoxyl group (e.g., methoxyl group), a halogen atom, and a hydroxyl group). In one embodiment of formula (I), $A^6$ is Met, or Trp, Phe, Tyr, β-homotryptophan, benzothiazolylalanine, α-naphthylalanine, β-naphthylalanine, or quinolylalanine optionally substituted with a methyl group, a methoxyl group, a halogen atom, or a hydroxyl group, wherein any number of methyl groups, methoxyl groups, hydroxyl groups, or halogen atoms, may be present on an aromatic ring at any position. Benzothiazolylalanine may be any of 2-benzothiazolylalanine, 4-benzothiazolylalanine, 5-benzothiazolylalanine, 6-benzothiazolylalanine, or 7-benzothiazolylalanine, and quinolylalanine may be any of 2-quinolylalanine, 3-quinolylalanine, 4-quinolylalanine, 5-quinolylalanine, 6-quinolylalanine, 7-quinolylalanine, or 8-quinolylalanine. In one embodiment of formula (I), $A^6$ is Trp, Met, S-homotryptophan, 2-benzothiazolylalanine, α-naphthylalanine, S-naphthylalanine, 6-chloro-Trp, 5-chloro-Trp, 2-quinolylalanine, or 8-quinolylalanine. In a specific embodiment of formula (I), $A^6$ is Trp, Met, 8-naphthylalanine, 2-quinolylalanine, 5-chloro-Trp, or 2-benzothiazolylalanine. In a more specific embodiment, $A^6$ can be 2-benzothiazolylalanine. An anti-EpoR peptide having $A^6$ with a structure within the scope described above is expected to highly retain at least one characteristic from efficacy such as EpoR inhibiting capability, cancer cell killing capability, reduction in normal cell killing capability, cancer cell killing capability at a low dosing frequency or the like, side effects, ability to migrate to a specific site, absorption/distribution/metabolism/excretion kinetics, bioavailability, and stability.

In one embodiment of formula (I), $A^7$ is —NH—CH($R^{47}$)—CO—, wherein $R^{47}$ is —(H or a linear or branched $C_{1-8}$ alkyl group or alkenyl group), wherein one of the carbon atoms in the alkyl group or alkenyl group may be replaced with a sulfur atom in one embodiment of formula (I), and has an —SH group in one embodiment. In one embodiment, $A^7$ is Cys, homocysteine, or penicillamine. An anti-EpoR peptide having $A^7$ with a structure within the scope described above is expected to highly retain at least one characteristic from efficacy such as EpoR inhibiting capability, cancer cell killing capability, reduction in normal cell killing capability, cancer cell killing capability at a low dosing frequency or the like, side effects, ability to migrate to a specific site, absorption/distribution/metabolism/excretion kinetics, bioavailability, and stability.

In one embodiment of formula (I), $A^8$ is —NH—CH($R^{48}$)—CO—, wherein $R^{48}$ is—(a linear or branched $C_{1\sim10}$ alkyl group or alkenyl group [wherein any 1, 2, or 3 carbon atoms are optionally replaced with nitrogen atoms]). In one embodiment of formula (I), $A^8$ is Lys, Arg, or absent. An anti-EpoR peptide having $A^8$ with a structure within the scope described above is expected to highly retain at least one characteristic from efficacy such as EpoR inhibiting capability, cancer cell killing capability, reduction in normal cell killing capability, cancer cell killing capability at a low dosing frequency or the like, side effects, ability to migrate to a specific site, absorption/distribution/metabolism/excretion kinetics, bioavailability, and stability.

In one embodiment of formula (I), $X^1$ is hydrogen, a peptide consisting of any 1 to 3 amino acids, or —C(=O)$R^1$, wherein $R^1$ is selected from the group consisting of hydrogen, a hydroxyl group, a linear or branched $C_{1\sim10}$ alkyl group optionally substituted with $R^2$, a linear or branched $C_{1\sim10}$ alkenyl group optionally substituted with $R^2$, a linear or branched $C_{1\sim10}$ alkynyl group optionally substituted with $R^2$, an aromatic or non-aromatic 5- to 10-membered ring optionally substituted with $R^2$, —$OR^2$, and —$NR^2_2$, wherein each $R^2$ is independently selected from the group consisting of hydrogen, a hydroxyl group, halogen, a benzyl group optionally substituted with halogen or a hydroxyl group, —$CH_3$, —$CH_2CH_3$, —$CH_2CH_2CH_3$, —$NH_2$, —$NHCH_3$, —$N(CH_3)_2$, =O, —COOH, —$OCH_3$, and —$OCH_2CH_3$. In one embodiment, $X^1$ is —COOH, a propionyl group, or a benzoyl group or a phenylacetyl group optionally substituted with halogen. In one embodiment, $X^1$ is Gly-Thr-Tyr, Thr-Tyr, Tyr, Phe, Ala, Trp, or a moiety in which these amino terminuses are substituted with a linear or branched $C_{1\sim5}$ acyl group. In one embodiment, $X^1$ is a benzoyl group or a p-fluorophenylacetyl group. An anti-EpoR peptide having $X^1$ with a structure within the scope described above is expected to highly retain at least one characteristic from efficacy such as EpoR inhibiting capability, cancer cell killing capability, reduction in normal cell killing capability, cancer cell killing capability at a low dosing frequency or the like, side effects, ability to migrate to a specific site, absorption/distribution/metabolism/excretion kinetics, bioavailability, and stability.

In one embodiment of formula (I), $X^2$ is hydrogen, a peptide consisting of any 1 to 3 amino acids, or —$NR^1_2$, wherein each $R^1$ is independently selected from the group consisting of hydrogen, a hydroxyl group, a linear or branched $C_{1\sim10}$ alkyl group optionally substituted with $R^2$, a linear or branched $C_{1\sim10}$ alkenyl group optionally substituted with $R^2$, a linear or branched $C_{1\sim11}$ alkynyl group optionally substituted with $R^2$, an aromatic or non-aromatic 5- to 10-membered ring optionally substituted with $R^2$, —$OR^2$, and —$NR^2_2$, or two $R^1$ attached to the same atom together form an aromatic or non-aromatic 5- to 10-membered ring optionally substituted with $R^2$, wherein each $R^2$ is independently selected from the group consisting of hydrogen, a hydroxyl group, halogen, a benzyl group optionally substituted with halogen or a hydroxyl group, —$CH_3$, —$CH_2CH_3$, —$CH_2CH_2CH_3$, —$NH_2$, —$NHCH_3$, —$N(CH_3)_2$, =O, —COOH, —$OCH_3$, and —$OCH_2CH_3$. In one embodiment, $X^2$ is Pro-Gln-Gly, Pro-Gln, Pro, or a moiety in which these carboxy terminuses are substituted with an amide. In one embodiment, $X^2$ is $NH_2$. An anti-EpoR peptide having $X^2$ with a structure within the scope described above is expected to highly retain at least one characteristic from efficacy such as EpoR inhibiting capability, cancer cell killing capability, reduction in normal cell killing capability, cancer cell killing capability at a low dosing frequency or the like, side effects, ability to migrate to a specific site, absorption/distribution/metabolism/excretion kinetics, bioavailability, and stability.

In one embodiment of formula (I), any two sulfur atoms in a peptide may form a disulfide bond. In one embodiment, a sulfur atom in $A^8$ is forming a disulfide bond with another sulfur atom (e.g., sulfur atom in the $2^{nd}$ Cys from the amino terminus).

In an embodiment of formula (I), a compound represented by any combination of $A^1$ to $A^8$, $X^1$, and $X^2$ is intended.

In one embodiment, the SCH ($A^1$) ($A^2$) ($A^3$) ($A^4$) ($A^5$) ($A^6$)V ($A^7$) ($A^8$) (SEQ ID NO: 1) part in formula (I) has a structure of SCHFGPLTWVCK (SEQ ID NO: 2) with a replacement of 1, 2, 3, 4, 5, 6, 7, or 8 amino acids. In a more specific embodiment, the part has a structure of SCHFGPLTWVCK (SEQ ID NO: 2) with a replacement of 1, 2, or 3 amino acids. In one embodiment, the SCH ($A^1$) ($A^2$) ($A^3$) ($A^4$) ($A^5$) ($A^6$)V ($A^7$) ($A^8$) part in formula (I) has a structure of SCHFGPLTWVCK (SEQ ID NO: 2) with a replacement at $A^1$, $A^6$, or a combination thereof. In one embodiment, the SCH ($A^1$) ($A^2$) ($A^3$) ($A^4$) ($A^5$) ($A^6$)V ($A^7$) ($A^8$) part in formula (I) is not SCHFGPLTWVCK (SEQ ID NO: 2).

In one embodiment, the anti-EpoR peptide of the present disclosure includes a modification at 1, 2, 3, or all of -Ac, —$NH_2$, F, and W in the structure of Ac-SCHFGPLTWVCK-$NH_2$ (SEQ ID NO: 9). In one embodiment, the anti-EpoR peptide of the present disclosure including a modification at F and/or W can have more improved activity (e.g., EpoR inhibiting capability or cancer cell killing capability) than the peptide of Ac-SCHFGPLTWVCK-$NH_2$ (SEQ ID NO: 9). In one embodiment, the anti-EpoR peptide of the present disclosure including a modification at -Ac and/or —$NH_2$ can retain the activity (e.g., EpoR inhibiting capability or cancer cell killing capability) of a peptide free of the modification. In one embodiment, the anti-EpoR peptide of the present disclosure includes a modification at an amino acid other than -Ac, —$NH_2$, F, and W in the structure of Ac-SCHFGPLTWVCK-$NH_2$ (SEQ ID NO: 9), independently from the modifications at -Ac, —$NH_2$, F, and W, and such modifications can be possible while retaining the activity (e.g., EpoR inhibiting capability or cancer cell killing capability) of a peptide free of the modifications. For example, a modification changing L to A in SEQ ID NO: 9 can improve the hydrophilicity of the peptide.

In one embodiment, the anti-EpoR peptide of the present disclosure is a peptide with a structure in which each amino acid in the SCH ($A^1$) ($A^2$) ($A^3$) ($A^4$) ($A^5$) ($A^6$)V ($A^7$) ($A^8$) (SEQ ID NO: 1) part in formula (I) is replaced with D-amino acid, and the order of amino acids is reversed, wherein $X^1$ and $X^2$ are defined the same as above. Such a peptide can, for example, exhibit a behavior that is different in metabolism.

In one specific embodiment of formula (I), $A^2$ can be Gly, $A^3$ can be Phe, $A^5$ can be Thr, $A^7$ can be Cys, and/or $A^8$ can be Lys. In one specific embodiment of formula (I), $A^1$ can be Tyr, p-fluorophenylalanine, or phenethylglycine. In a more specific embodiment, $A^1$ can be Tyr. In a specific embodiment of formula (I), $A^4$ can be Leu or Met. In a more specific embodiment, $A^4$ can be Met. In one specific embodiment of formula (I), $A^6$ can be Trp, Met, 8-naphthylalanine, 2-quinolylalanine, 5-chloro-Trp, or 2-benzothiazolylalanine. In a more specific embodiment of formula (I), $A^6$ can be 2-benzothiazolylalanine.

In one embodiment, the anti-EpoR peptide of the present disclosure has the structure represented by the following formula (II).

Formula (II):

$X^1$-kcvwtl($B^1$)Gfhcs-$X^2$,

[wherein $X^1$ is an amino terminus side of the peptide, and $X^2$ is a carboxy terminus side of the peptide].

In one embodiment of formula (II), $B^1$ is Gly or D-proline. An anti-EpoR peptide having $B^1$ with a structure within the scope described above is expected to highly retain at least one characteristic from efficacy such as EpoR inhibiting capability, cancer cell killing capability, reduction in normal cell killing capability, cancer cell killing capability at a low dosing frequency or the like, side effects, ability to migrate to a specific site, absorption/distribution/metabolism/excretion kinetics, bioavailability, and stability.

In one embodiment of formula (II), $X^1$ is hydrogen, a peptide consisting of any 1 to 3 amino acids, or —C(=O)$R^1$, wherein $R^1$ is selected from the group consisting of hydrogen, a hydroxyl group, a linear or branched $C_{1\sim10}$ alkyl group optionally substituted with $R^2$, a linear or branched $C_{1\sim10}$ alkenyl group optionally substituted with $R^2$, a linear or branched $C_{1\sim10}$ alkynyl group optionally substituted with $R^2$, an aromatic or non-aromatic 5- to 10-membered ring optionally substituted with $R^2$, —$OR^2$, and —$NR^2{}_2$, wherein each $R^2$ is independently selected from the group consisting of hydrogen, a hydroxyl group, halogen, a benzyl group optionally substituted with halogen or a hydroxyl group, —$CH_3$, —$CH_2CH_3$, —$CH_2CH_2CH_3$, —$NH_2$, —$NHCH_3$, —$N(CH_3)_2$, =O, —COOH, —$OCH_3$, and —$OCH_2CH_3$. In one embodiment, $X^1$ is —COOH, a propionyl group, or a benzoyl group or a phenylacetyl group optionally substituted with halogen. In one embodiment, $X^1$ is Gly-Thr-Tyr, Thr-Tyr, Tyr, Phe, Ala, Trp, or a moiety in which these amino terminuses are substituted with a linear or branched $C_{1\sim5}$ acyl group. In one embodiment, X is a benzoyl group or a p-fluorophenylacetyl group. An anti-EpoR peptide having $X^1$ with a structure within the scope described above is expected to highly retain at least one characteristic from efficacy such as EpoR inhibiting capability, cancer cell killing capability, reduction in normal cell killing capability, cancer cell killing capability at a low dosing frequency or the like, side effects, ability to migrate to a specific site, absorption/distribution/metabolism/excretion kinetics, bioavailability, and stability.

In one embodiment of formula (II), $X^2$ is hydrogen, a peptide consisting of any 1 to 3 amino acids, or —$NR^1{}_2$, wherein each $R^1$ is selected from the group consisting of hydrogen, a hydroxyl group, a linear or branched $C_{1\sim10}$ alkyl group optionally substituted with $R^2$, a linear or branched $C_{1\sim10}$ alkenyl group optionally substituted with $R^2$, a linear or branched $C_{1\sim10}$ alkynyl group optionally substituted with $R^2$, an aromatic or non-aromatic 5- to 10-membered ring optionally substituted with $R^2$, —$OR^2$, and —$NR^2{}_2$, or two $R^1$ attached to the same atom together form an aromatic or non-aromatic 5- to 10-membered ring optionally substituted with $R^2$, and wherein each $R^2$ is independently selected from the group consisting of hydrogen, a hydroxyl group, halogen, benzyl optionally substituted with halogen or a hydroxyl group, —$CH_3$, —$CH_2CH_3$, —$CH_2CH_2CH_3$, —$NH_2$, —$NHCH_3$, —$N(CH_3)_2$, =O, —COOH, —$OCH_3$, and —$OCH_2CH_3$. In one embodiment, $X^2$ is Pro-Gln-Gly, Pro-Gln, Pro, or a moiety in which these carboxy terminuses are substituted with amide. In one embodiment, $X^2$ is $NH_2$. An anti-EpoR peptide having $X^2$ with a structure within the scope described above is expected to highly retain at least one characteristic from efficacy such as EpoR inhibiting capability, cancer cell killing capability, reduction in normal cell killing capability, cancer cell killing capability at a low dosing frequency or the like, side effects, ability to migrate to a specific site, absorption/distribution/metabolism/excretion kinetics, bioavailability, and stability.

In one embodiment, the anti-EpoR peptide of the present disclosure is a peptide with the structure specified above having any number (e.g., 1, 2, 3, 4, 5, or 6) of amino acids replaced from an L form to a D form. In one embodiment, amino acids corresponding to those other than F and W in Ac-SCHFGPLTWVCK-$NH_2$ (SEQ ID NO: 9) are D-amino acids. Although not wishing to be bound by any theory, the sheet structure formed by a peptide can change by replacing some of the amino acids from an L-form to a D-form, thus D-amino acids may be introduced to retain the sheet structure. A peptide with such replacement of L-forms with D-forms can also retain one or more characteristics from EpoR inhibiting capability, cancer cell killing capability, reduction in normal cell killing capability, cancer cell killing capability at a low dosing frequency, ability to migrate to a specific site, absorption/distribution/metabolism/excretion kinetics, and stability in the same manner as the original peptide. In one embodiment, amino acids corresponding to F and W in Ac-SCHFGPLTWVCK-$NH_2$ (SEQ ID NO: 9) can be D-amino acids. In such an embodiment, the peptide activity can change.

In one embodiment, the anti-EpoR peptide of the present disclosure is a peptide with a structure specified above having conservative substitutions of any number (e.g., 1, 2, 3, 4, 5, or 6) of amino acids. Such a peptide comprising a conservative substitution can retain one or more characteristics from efficacy such as EpoR inhibiting capability, cancer cell killing capability, reduction in normal cell killing capability, cancer cell killing capability at a low dosing frequency or the like, side effects, ability to migrate to a specific site, absorption/distribution/metabolism/excretion kinetics, bioavailability, and stability in the same manner as the original peptide.

In one embodiment, the anti-EpoR peptide of the present disclosure is a compound having one of the following structures (wherein $X^1$ and $X^2$ are defined in the same as above).

$X^1$-SCHFGPLTWVCK-$X^2$ [SEQ ID NO: 2]

$X^1$-SCH(p-fluoro-Phe)GPLTWVCK-$X^2$ (SEQ ID NO: 19)

$X^1$-SCH(p-chloro-Phe)GPLTWVCK-$X^2$ (SEQ ID NO: 20)

$X^1$-SCH(m-chloro-Phe)GPLTWVCK-$X^2$ (SEQ ID NO: 21)

$X^1$-SCH(3,4-difluoro-Phe)GPLTWVCK-$X^2$ (SEQ ID NO: 44)

$X^1$-SCHYGPLTWVCK-$X^2$ [SEQ ID NO: 3]

$X^1$-SCH(phenylglycine)GPLTWVCK-$X^2$ (SEQ ID NO: 22)

```
                                                 (SEQ ID NO: 23)
X¹-SCH(phenethylglycine)GPLTWVCK-X²

[SEQ ID NO: 4]
X¹-SCHFAPLTWVCK-X²

(SEQ ID NO: 24)
X¹-SCHFaPLTWVCK-X²

[SEQ ID NO: 5]
X¹-SCHFGALTWVCK-X²

(SEQ ID NO: 25)
X¹-SCHFG(homoproline)LTWVCK-X²

[SEQ ID NO: 6]
X¹-SCHFGPATWVCK-X²

[SEQ ID NO: 7]
X¹-SCHFGPMTWVCK-X²

[SEQ ID NO: 8]
X¹-SCHFGPLIMVOK-X²

(SEQ ID NO: 30)
X¹-SCHFGPLT(6-chloro-Trp)VCK-X²

(SEQ ID NO: 31)
X¹-SCHFGPLT(5-chloro-Trp)VCK-X²

(SEQ ID NO: 26)
X¹-SCHFGPLT(β-homotryptophan)VCK-X²

(SEQ ID NO: 27)
X¹-SCHFGPLT(α-naphthylalanine)VCK-X²

(SEQ ID NO: 28)
X¹-SCHFGPLT(β-naphthylalanine)VCK-X²

(SEQ ID NO: 29)
X¹-SCHFGPLT(8-quinolylalanine)VCK-X²

(SEQ ID NO: 45)
X¹-SCHFGPLT(2-quinolylalanine)VCK-X²

(SEQ ID NO: 46)
X¹-SCHFGPLT(2-benzothiazolylalanine)VCK-X²

(SEQ ID NO: 32)
X¹-SCHFGPLTWV(homocysteine)K-X²

(SEQ ID NO: 33)
X¹-SCHFGPLTWV(penicillamine)K-X²

(SEQ ID NO: 38)
X¹-SCH(3,4-difluoro-Phe)GPLT(2-
benzothiazolylalanine)VCK-X²

(SEQ ID NO: 40)
X¹-SCH(p-fluoro-Phe)GPLT(2-
benzothiazolylalanine)VCK-X²

(SEQ ID NO: 42)
X¹-SCHYGPLT(2-benzothiazolylalanine)VCK-X²

(SEQ ID NO: 37)
X¹-SCH(3,4-difluoro-Phe)GPLT(2-quinolylalanine)
VCK-X²

(SEQ ID NO: 39)
X¹-SCH(p-fluoro-Phe)GPLT(2-quinolylalanine)VCK-X²

(SEQ ID NO: 41)
X¹-SCHYGPLT(2-quinolylalanine)VCK-X²

(SEQ ID NO: 36)
X¹-SCH(3,4-difluoro-Phe)GPLT(8-quinolylalanine)
VCK-X²

(SEQ ID NO: 47)
X¹-SCH(p-fluoro-Phe)GPLT(8-quinolylalanine)VCK-X²

(SEQ ID NO: 48)
X¹-SCHYGPLT(8-quinolylalanine)VCK-X²

(SEQ ID NO: 34)
X¹-kcvwtlpGfhcs-X²

(SEQ ID NO: 35)
X¹-kcvwtlGGfhcs-X²

(SEQ ID NO: 49)
X¹-SCH(4-pyridylalanine)GPLTWVCK-X²

(SEQ ID NO: 50)
X¹-SCH(3-pyridylalanine)GPLTWVCK-X²

(SEQ ID NO: 51)
X¹-SCH(p-methoxy-Phe)GPLTWVCK-X²

(SEQ ID NO: 52)
X¹-SCH(m-methoxy-Phe)GPLTWVCK-X²

(SEQ ID NO: 53)
X¹-SCH(m-hydroxy-Phe)GPLTWVCK-X²

(SEQ ID NO: 54)
X¹-SCH(1-naphthylalanine)GPLTWVCK-X²

(SEQ ID NO: 55)
X¹-SCH(2-naphthylalanine)GPLTWVCK-X²

(SEQ ID NO: 46)
X¹-SCHFGPLT(2-benzothiazolylalanine)VCK-X²

(SEQ ID NO: 56)
X¹-SCHFGPLT(3-benzothiazolylalanine)VCK-X²

(SEQ ID NO: 57)
X¹-SCHYGPMT(2-benzothiazolylalanine)VCK-X²
```

In one embodiment, the anti-EpoR peptide of the present disclosure is a compound having one of the following structures (wherein Ac is an acetyl group).

```
                                                 [SEQ ID NO: 9]
Ac-SCHFGPLTWVCK-NH₂

(SEQ ID NO: 16)
(benzoyl)-SCHFGPLTWVCK-NH₂

(SEQ ID NO: 17)
(p-fluorophenylacetyl)-SCHFGPLTWVCK-NH₂

(SEQ ID NO: 18)
(propionyl)-SCHFGPLTWVCK-NH₂

(SEQ ID NO: 19)
Ac-SCH(p-fluoro-Phe)GPLTWVCK-NH₂

(SEQ ID NO: 20)
Ac-SCH(p-chloro-Phe)GPLTWVCK-NH₂

(SEQ ID NO: 21)
Ac-SCH(m-chloro-Phe)GPLTWVCK-NH₂

(SEQ ID NO: 44)
Ac-SCH(3,4-difluoro-Phe)GPLTWVCK-NH₂

[SEQ ID NO: 10]
Ac-SCHYGPLTWVCK-NH₂

(SEQ ID NO: 22)
Ac-SCH(phenylglycine)GPLTWVCK-NH₂

(SEQ ID NO: 23)
Ac-SCH(phenethylglycine)GPLTWVCK-NH₂
```

Ac-SCHFAPLTWVCK-NH₂ (SEQ ID NO: 11)

Ac-SCHFaPLTWVCK-NH₂ (SEQ ID NO: 24)

Ac-SCHFGALTWVCK-NH₂ (SEQ ID NO: 12)

Ac-SCHFG(homoproline)LTWVCK-NH₂ (SEQ ID NO: 25)

Ac-SCHFGPATWVCK-NH₂ (SEQ ID NO: 13)

Ac-SCHFGPMTWVCK-NH₂ (SEQ ID NO: 14)

Ac-SCHFGPLTMVCK-NH₂ (SEQ ID NO: 15)

Ac-SCHFGPLT(6-chloro-Trp)VCK-NH₂ (SEQ ID NO: 30)

Ac-SCHFGPLT(5-chloro-Trp)VCK-NH₂ (SEQ ID NO: 31)

Ac-SCHFGPLT(β-homotryptophan)VCK-NH₂ (SEQ ID NO: 26)

Ac-SCHFGPLT(α-naphthylalanine)VCK-NH₂ (SEQ ID NO: 27)

Ac-SCHFGPLT(β-naphthylalanine)VCK-NH₂ (SEQ ID NO: 28)

Ac-SCHFGPLT(8-quinolylalanine)VCK-NH₂ (SEQ ID NO: 29)

Ac-SCHFGPLT(2-quinolylalanine)VCK-NH₂ (SEQ ID NO: 45)

Ac-SCHFGPLT(2-benzothiazolylalanine)VCK-NH₂ (SEQ ID NO: 46)

Ac-SCHFGPLTWV(homocysteine)K-NH₂ (SEQ ID NO: 32)

Ac-SCHFGPLTWV(penicillamine)K-NH₂ (SEQ ID NO: 33)

Ac-SCH(3,4-difluoro-Phe)GPLT(2-benzothiazolylalanine)VCK-NH₂ (SEQ ID NO: 38)

Ac-SCH(p-fluoro-Phe)GPLT(2-benzothiazolylalanine)VCK-NH₂ (SEQ ID NO: 40)

Ac-SCHYGPLT(2-benzothiazolylalanine)VCK-NH₂ (SEQ ID NO: 42)

Ac-SCH(3,4-difluoro-Phe)GPLT(2-quinolylalanine)VCK-NH₂ (SEQ ID NO: 37)

Ac-SCH(p-fluoro-Phe)GPLT(2-quinolylalanine)VCK-NH₂ (SEQ ID NO: 39)

Ac-SCHYGPLT(2-quinolylalanine)VCK-NH₂ (SEQ ID NO: 41)

Ac-SCH(3,4-difluoro-Phe)GPLT(8-quinolylalanine)VCK-NH₂ (SEQ ID NO: 36)

Ac-SCH(p-fluoro-Phe)GPLT(8-quinolylalanine)VCK-NH₂ (SEQ ID NO: 47)

Ac-SCHYGPLT(8-quinolylalanine)VCK-NH₂ (SEQ ID NO: 48)

Ac-kcvwtlpGfhcs-NH₂ (SEQ ID NO: 34)

Ac-kcvwtlGGfhcs-NH₂ (SEQ ID NO: 35)

Ac-SCH(4-pyridylalanine)GPLTWVCK-NH₂ (SEQ ID NO: 49)

Ac-SCH(3-pyridylalanine)GPLTWVCK-NH₂ (SEQ ID NO: 50)

Ac-SCH(p-methoxy-Phe)GPLTWVCK-NH₂ (SEQ ID NO: 51)

Ac-SCH(m-methoxy-Phe)GPLTWVCK-NH₂ (SEQ ID NO: 52)

Ac-SCH(m-hydroxy-Phe)GPLTWVCK-NH₂ (SEQ ID NO: 53)

Ac-SCH(1-naphthylalanine)GPLTWVCK-NH₂ (SEQ ID NO: 54)

Ac-SCH(2-naphthylalanine)GPLTWVCK-NH₂ (SEQ ID NO: 55)

Ac-SCHFGPLT(2-benzothiazolylalanine)VCK-NH₂ (SEQ ID NO: 46)

Ac-SCHFGPLT(3-benzothiazolylalanine)VCK-NH₂ (SEQ ID NO: 56)

Ac-SCHYGPMT(2-benzothiazolylalanine)VCK-NH₂ (SEQ ID NO: 57)

In one embodiment, the peptide of the present disclosure is protected with a protecting group (e.g., C1-6 acyl group such as a formyl group or an acetyl group, or the like). For example, a protecting group is introduced to OH, NH₂, SH, or the like on a side chain of an amino acid within a molecule. In one embodiment, a sugar chain or a PEG chain may be bound to the peptide of the present disclosure.

The peptide of the present disclosure can be provided in a form of salt. A salt can be either a base addition salt or an acid addition salt, but is preferably a physiologically acceptable acid addition salt. Examples of acid addition salt include salts with an inorganic acid (e.g., hydrochloric acid, phosphoric acid, hydrobromic acid, or sulfuric acid), salts with an organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, aspartic acid, glutamic acid, or the like), and the like. Examples of base addition salt include salts with an inorganic base (sodium, potassium, calcium, magnesium, aluminum, ammonium, or the like) and salts with an organic base (e.g., trimethylamine, triethylamine, pyridine, picoline, 2,6-lutidine, ethanolamine, diethanolamine, triethanolamine, cyclohexylamine, dicyclohexylamine, N,N'-dibenzylethylenediamine, lysine, arginine, histidine, or the like).

The peptide of the present disclosure can be in a form of a solvate. A solvent is not particularly limited, as long as it is pharmaceutically acceptable. Examples thereof include water, ethanol, glycerol, acetic acid, and the like.

The peptide of the present disclosure can be prepared as a prodrug. As a prodrug, a compound that is converted into the peptide of the present disclosure after an enzymatic reaction (oxidation, reduction, hydrolysis, or the like) or a reaction with stomach acid or the like under a physiological condition in vivo can be used. In one embodiment, examples of the prodrug of the present disclosure include compounds wherein an amino group of the peptide of the present disclosure is acylated, alkylated, or phosphorylated (e.g., eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated compounds and the like), compounds wherein a hydroxyl group of the peptide of the present disclosure is acylated, alkylated, phosphorylated, or borated (e.g., acetylated, palmitoylated, propanoylated, pivaloylated, succinylated, fumarylated, alanylated, or dimethylaminomethylcarbonylated compounds and the like), and the like. These compounds can be manufactured from the peptide of the present disclosure by a known method.

The peptide of the present disclosure can be manufactured in accordance with a known peptide synthesis method. A peptide synthesis method can be, for example, either solid-phase synthesis or liquid-phase synthesis. Specifically, a peptide of interest can be manufactured by condensing an amino acid or a partial peptide that can constitute the peptide of the present disclosure with a remaining portion and eliminating a protecting group if the product has a protecting group. Examples of known methods of condensation and elimination of protecting groups include the methods described in the following (1) to (3).

(1) Nobuo Izumiya et al., Pepuchido Gosei no Kiso to Jikken [Fundamentals and experiments of peptide synthesis], Maruzen (1985)
(2) The Fifth Series of Experimental Chemistry, Polymer chemistry, Vol. 26, Maruzen (2007)
(3) authored by Yasuyoshi Nogami, Patona Yakuhin Seizogaku [Partner Pharmaceutical Technochemistry], $2^{nd}$ print, Nankodo (2012).

More specifically, a commercially available peptide synthesis resin can be used for the synthesis of the peptide of the present disclosure. For example, resin based on polystyrene can be used. To obtain a peptide with an amidated C-terminus, Fmoc-NH-SAL resin (Rink amide resin), MBHA resin, Sieber amide resin, PAL resin, Ramage amide resin, such resins with a linker or swelling agent such as polyethylene glycol introduced between an amino functional group and polystyrene, and the like can be used as the starting material resin. Such resin and amino acid with an α-amino group and a side chain functional group protected with a suitable protecting group (e.g., Boc or Fmoc) are used as the raw material and condensed onto the resin with various known condensing methods in accordance with the order of the sequence of the peptide of interest. A peptide is cut out from the resin at the end of the reaction while simultaneously eliminating various protecting groups, and optionally an intramolecular disulfide bond formation reaction is performed in a highly diluted solution to obtain the peptide of interest. Removal (elimination) of a protecting group and cleavage of a peptide from resin can be performed by a known method (e.g., acid treatment with trifluoroacetic acid). A peptide with an acylated N-terminus can be prepared through a reaction with acetic anhydride or the like. A crude peptide cleaved from resin can be purified using various known purification means.

Amino Acids Used in Peptide Synthesis

Amino acids used in peptide synthesis (naturally-occurring amino acids and non-naturally-occurring amino acids) are available from any suitable supplier (e.g., Merck, Watanabe Chemical, Enamine Ltd., Bienta, ChemSpace, Sundia MediTech Company, Ltd., Combi-Blocks. Inc, AnalytiCon Discovery GmbH, PharmaBlock (Nanjing) R&D Co., Ltd, Chemexpress Co., Ltd., J&W Pharmlab, LLC, SAI Life Sciences Ltd, AstaTech, UkrOrgSyntez, Selleck Chemicals, WuXi AppTec, Vitas-M Laboratory, LTD., Bepharm, Life Chemicals Inc, Accela ChemBio Co., Ltd., Apollo Scientific Ltd, NovoChemy Ltd, Key Organics Ltd (Bionet Research), Matrix Scientific, Toronto Research chemicals Inc., MAYBRIDGE, Chem-Impex International, Inc., Allychem, Pharmeks Ltd., Biorelevant, AOBChem, ACRO Biosystems, Maison Chemical, Advanced ChemBlocks, Inc., Bellen, Microsource Discovery Systems, Inc., Taros Chemicals GmbH&Co.KG, Senn Chemicals AG, Sinocompound Catalysts Co., Ltd., Syngene International Ltd., BroadPharm, EDASA Scientific, Hi-tech chemistry corp, or the like). Amino acids (naturally-occurring amino acids and non-naturally-occurring amino acids) used in peptide synthesis can also be readily synthesized by those skilled in the art by using any known synthesis method (e.g., Strecker reaction (Strecker, A. (1850). Ueber die kunstliche Bildung der Milchsaure und einen neuen, dem Glycocoll homologen Korper". Ann. 75: 27-45., Strecker, A. (1854). "Ueber einen neuen aus Aldehyd-Ammoniak und Blausaure entstehenden Korper". Ann. 91: 349-351.)) A method of introducing a protecting group (e.g., Boc or Fmoc) and/or label (e.g., radioactive atom or biotin) to a given amino acid for synthesizing a peptide is also known. Those skilled in the art can readily apply such an amino acid modification.

<Efficiency of Anti-EpoR Peptide>

Properties of the Peptide of the Present Disclosure

In one embodiment, the peptide of the present disclosure, or a salt or solvate thereof, or a prodrug thereof has one or more characteristics that are improved compared to $CH_3$—CO—SCHFGPLTWVCK—$NH_2$ (SEQ ID NO: 9). Examples of such a characteristic include lower $IC_{50}$ for human EpoR, ability to kill cancer cells (e.g., cancer cell line such as HepG2) at a lower concentration, ability of requiring a higher concentration to kill normal cells, ability to kill cancer cells at a lower dosing frequency, ability to migrate to a specific site (e.g., cancer tissue) at a greater quantity, improved absorption/distribution/metabolism/excretion kinetics, greater stability during storage, and the like.

A test for studying the properties described above is a test that can be readily conducted by those skilled in the art by referring to the descriptions herein, such as a contact test with cultured cell, dosing test in an animal model, blood kinetics test, and toxicological evaluation. Those skilled in the art can identify the anti-EpoR peptide of the present disclosure having at least one of the characteristics described above by preparing any peptide having the structure described above and conducting such a test on the prepared peptide.

In one embodiment, the anti-EpoR peptide of the present disclosure has an ability to kill HepG2 cells with a mean (e.g., mean for 10 segments; mean for n=2, 3, or greater number of replicates as needed) of TB (Trypan blue) stained positive cell counts within a 1 $mm^2$ segment, which is equivalent to or greater than the result for a peptide of $CH_3$—CO—SCHFGPLTWVCK—$NH_2$ (SEQ ID NO: 9) when 1.0 to $1.5 \times 10^3$ HepG2 cells are reacted for 24 hours in 400 μL of solution comprising 120 μM, 60 μM, 30 μM, or 15 μM of the peptide.

In one embodiment, the anti-EpoR peptide of the present disclosure can have a more potent ability to inhibit (e.g., kill) at least one type of human cancer cell line (e.g., liver cancer, pancreatic cancer, or leukemia cell line) than a peptide of $CH_3$—CO—SCHFGPLTWVCK—$NH_2$ (SEQ ID NO: 9) when evaluated by a WST assay. For example, the peptide exhibits a more potent inhibitory effect than a peptide of $CH_3$—CO—SCHFGPLTWVCK—$NH_2$ (SEQ ID NO: 9)

when exposed to a human cancer cell line at 150 μM for 72 hours and evaluated by a WST assay.

In one embodiment, the anti-EpoR peptide of the present disclosure can have a more potent ability to inhibit (e.g., kill) at least one type of human cancer cell line (e.g., breast cancer cell line) than a peptide of $CH_3$—CO—SCHFG-PLTWVCK-$NH_2$ (SEQ ID NO: 9) when the cell proliferation capacity is evaluated using the amount of ATP as an indicator. For example, the peptide exhibits a more potent inhibitory effect than a peptide of $CH_3$—CO—SCHFG-PLTWVCK-$NH_2$ (SEQ ID NO: 9) when exposed to a human cancer cell line at 30 or 100 μM for 72 hours, and the cell proliferation capacity is evaluated using the amount of ATP as an indicator.

In one embodiment, the anti-EpoR peptide of the present disclosure can have an ability where the CFU-E (Erythroid Colony Forming Unit) count is not significantly different, when bone marrow cells (e.g., mouse) seeded on a plate is exposed to an anti-EpoR peptide at a final concentration of 100 μM and recombinant human erythropoietin (1 U/mL) for 72 hours, relative to the result for a control of only recombinant human erythropoietin (1 U/mL).

In one embodiment, the anti-EpoR peptide of the present disclosure can have the ability to achieve at least one of the following when the anti-EpoR peptide is intraperitoneally administered for 2 or 4 weeks in a regimen of 2 or 3 times a week at 0.2 mg/day when a tumor volume (V)=length of tumor (L)×width of tumor (W)²/2 reaches about 150 to 200 mm³ in a 6-week-old male nude mouse (BALB/cSlc-nu/nu), to which about 5×10⁶ human pancreatic cancer derived AsPC-1 cells (ECACC, 96020930) have been transplanted subcutaneously to the right side on the back:

- the timing at which reduced tumor volume compared to an untreated control is observed is (e.g., 1 day or more, 2 days or more, 3 days or more, 4 days or more, 5 days or more, 6 days or more, or 7 days or more) earlier than when a peptide of $CH_3$—CO—SCHFGPLTWVCK-$NH_2$ (SEQ ID NO: 9) is administered;
- the tumor volume on day 21 from the start of administration is smaller (e.g., by about 10% or more, about 20% or more, about 30% or more, about 40% or more, or about 50% or more) than when a peptide of $CH_3$—CO—SCHFGPLTWVCK-$NH_2$ (SEQ ID NO: 9) is administered;
- the body weight of the mouse on day 21 from the start of administration is not different compared to an untreated control (e.g., the difference from the control is less than 10%, less than 7%, less than 5%, less than 3%, less than 2%, or less than 1%);
- the hematocrit value on day 21 from the start of administration is not different compared to an untreated control (e.g., the difference from the control is less than 30%, less than 20%, less than 15%, less than 10%, or less than 5%); and
- the blood hemoglobin concentration on day 21 from the start of administration is not different compared to an untreated control (e.g., the difference from the control is less than 30%, less than 20%, less than 15%, less than 10%, or less than 5%).

As specifically described in the Examples, the peptide of the present disclosure was confirmed to have an effect of killing tumor cells and is expected to be effectively useable for various diseases (e.g., proliferative disease, adenomyosis, or diabetic retinopathy) as a result of the study including other findings.

<Composition>

In one aspect, the present disclosure provides a composition comprising the peptide of the present disclosure or a salt thereof, or a solvate thereof, or a prodrug thereof. In a specific embodiment, the composition of the present disclosure has one or more characteristics from improved efficacy such as potent EpoR inhibiting capability, high cancer cell killing capability, low normal cell killing capability, cancer cell killing capability at a low dosing frequency or the like, reduction in side effects, ability to migrate specifically to a specific site, improved absorption/distribution/metabolism/excretion kinetics, improvement in bioavailability, and high stability. In one embodiment, the composition of the present disclosure can be used in treatment or prevention/prophylaxis of a proliferative disease, adenomyosis, or diabetic retinopathy.

A composition comprising the peptide of the present disclosure or a salt thereof, or a solvate thereof, or a prodrug thereof can contain any additive. Examples of additive include carriers, excipients, lubricating agents, binding agents, disintegrants, solvents, solubilizers, suspending agents, isotonizing agents, buffering agents, analgesics, antiseptics, antioxidants, colorants, flavoring agents, adsorbents, and humectants.

Examples of excipients include lactose, white sugar, D-mannitol, starch, corn starch, crystalline cellulose, light anhydrous silicic acid, and the like. Examples of lubricating agents include magnesium stearate, calcium stearate, talc, colloidal silica, and the like. Examples of binding agents include crystalline cellulose, white sugar, D-mannitol, dextrin, hydroxypropyl cellulose, hydroxypropyl methylcellulose, polyvinylpyrrolidone, starch, sucrose, gelatin, methyl cellulose, sodium carboxymethyl cellulose, and the like. Examples of disintegrants include starch, carboxymethyl cellulose, calcium carboxymethyl cellulose, sodium carboxymethyl starch, L-hydroxypropyl cellulose, and the like.

Examples of solvents include injection solution, alcohol, propylene glycol, macrogol, sesame oil, corn oil, olive oil, and the like. Examples of solubilizers include polyethylene glycol, propylene glycol, D-mannitol, benzyl benzoate, ethanol, trisaminomethane, cholesterol, triethanolamine, sodium carbonate, sodium citrate, and the like. Examples of suspending agents include surfactants such as stearyl triethanolamine, sodium lauryl sulfate, lauryl aminopropionic acid, lecithin, benzalkonium chloride, benzethonium chloride, and glycerin monostearate, e.g., hydrophilic polymers such as polyvinyl alcohol, polyvinylpyrrolidone, sodium carboxymethyl cellulose, methyl cellulose, hydroxymethyl cellulose, hydroxyethyl cellulose, hydroxypropyl cellulose, and the like. Examples of isotonizing agents include glucose, D-sorbitol, sodium chloride, glycerin, D-mannitol, and the like. Examples of buffering agents include buffer such as phosphate, acetate, carbonate, and citrate and the like. Examples of analgesics include benzyl alcohol and the like. Examples of antiseptics include para-hydroxybenzoic acid ester, chlorobutanol, benzyl alcohol, phenethyl alcohol, dehydroacetic acid, sorbic acid, and the like. Examples of antioxidants include sulfite, ascorbic acid, α-tocopherol, and the like.

The prepared injection solution is generally filled in a suitable ampule. An injection composition can be dissolved in a conventional aqueous diluent upon administration and used as a solution. Examples of aqueous diluent include aqueous glucose solution, saline, Ringer's solution, nutrition supplement solution, and the like.

When an injection contains phosphoric acid or a salt thereof, the sodium phosphate or potassium phosphate concentration in the injection can be about 0.1 mM to 500 mM and preferably about 1 mM to 100 mM. Examples of methods that can be used to prepare a sterile formulation include, but are not limited to, a method of sterilizing the entire manufacturing process, a method of disinfecting with gamma rays, a method of adding an antiseptic, and the like.

In one embodiment, a composition comprising the peptide of the present disclosure or a salt thereof, or a solvate thereof, or a prodrug thereof can be provided as a kit. In one specific embodiment, a kit has (a) a container comprising the peptide of the present disclosure or a salt thereof, or a solvate thereof, or a prodrug thereof, or a composition comprising the same in a solution or lyophilized form, and optionally (b) a second container comprising a diluent or a reconstitution solution, and optionally (c) an instruction manual. In one embodiment, a kit can comprise one or more of (iii) a buffering agent, (iv) a diluent, (v) a filter, (vi) a needle, and (v) a syringe.

In one embodiment, the kit of the present disclosure comprises an instruction manual for use of the kit of the present disclosure. Examples of a suitable container include a bottle, vial (e.g., dual-chamber vial), syringe (dual-chamber syringe and the like), and test tube. Such a container can be made of various materials such as glass or plastic. In one embodiment, the kit of the present disclosure can comprise another container comprising a constituent element that is different from the peptide of the present disclosure or a salt thereof, or a solvate thereof, or a prodrug thereof.

<Application>

The peptide of the present disclosure or a salt thereof, or a solvate thereof, or a prodrug thereof, or a composition comprising the same can be used in any suitable application. In one embodiment, the application can be the prevention/prophylaxis or treatment of a proliferative disease (e.g., adenomyosis), rheumatism, keloid, or diabetic retinopathy. In one embodiment, the proliferative disease can be adenomyosis, malignant tumor or benign tumor (e.g., tumor such as primary, metastatic, or recurrent breast cancer, prostate cancer, pancreatic cancer, gastric cancer, lung cancer, large intestinal cancer (colon cancer, rectal cancer, or anal cancer), esophageal cancer, duodenal cancer, head and neck cancer (tongue cancer, pharyngeal cancer, laryngeal cancer, thyroid cancer), brain tumor, schwannoma, neuroblastoma, glioma, non-small cell lung cancer, small cell lung cancer, liver cancer, kidney cancer, bile duct cancer, uterine cancer (endometrial cancer or cervical cancer), ovarian cancer, bladder cancer, skin cancer, hemangioma, malignant lymphoma, malignant melanoma, bone tumor, angiofibroma, retinal sarcoma, penile cancer, pediatric solid tumor, Kaposi's sarcoma, AIDS-related Kaposi's sarcoma, maxillary sinus tumor, fibrous histiocytoma, leiomyosarcoma, rhabdomyosarcoma, liposarcoma, uterine fibroid, osteoblastoma, osteosarcoma, chondrosarcoma, cancerous mesothelioma, or leukemia). In one embodiment, a proliferative disease can be lung cancer, liver cancer, ovarian cancer, pancreatic cancer, kidney cancer, large intestinal cancer, melanoma, brain tumor, gastric cancer, or breast cancer. In one specific embodiment, a proliferative disease can be breast cancer, pancreatic cancer, liver cancer, malignant lymphoma, or leukemia (or a subpopulation consisting of any options thereof).

The peptide of the present disclosure or a salt thereof, or a solvate thereof, or a prodrug thereof, or a composition comprising the same can be used on any subject such as avian and mammals (e.g., mouse, rat, hamster, rabbit, cat, dog, cow, sheep, pig, monkey, human, and the like).

<Use>

In one embodiment, the present disclosure provides use of the peptide of the present disclosure or a salt thereof, or a solvate thereof, or a prodrug thereof, or a composition or kit comprising the same, or a method of use in any suitable application. In a specific embodiment, the peptide of the present disclosure or a salt thereof, or a solvate thereof, or a prodrug thereof, or a composition or kit comprising the same can have one or more characteristics from improvement in efficacy such as potent EpoR inhibiting capability, high cancer cell killing capability, low normal cell killing capability, cancer cell killing capability at a low dosing frequency or the like, reduction in side effects, ability to specifically migrate to a specific site, improved absorption/distribution/metabolism/excretion kinetics, improvement in bioavailability, and high stability, and can therefore be used for the treatment or prevention/prophylaxis of proliferative disease (e.g., adenomyosis) or diabetic retinopathy. Thus, in one embodiment, the present disclosure provides a method for treating or preventing a proliferative disease (e.g., adenomyosis) or diabetic retinopathy in a subject, comprising administering to the subject an effective amount of the peptide of the present disclosure or a salt thereof, or a solvate thereof, or a prodrug thereof. In another embodiment, the present disclosure provides use of the peptide of the present disclosure or a salt thereof, or a solvate thereof, or a prodrug thereof in the manufacture of a drug for the treatment or prevention/prophylaxis of proliferative disease (e.g., adenomyosis) or diabetic retinopathy.

Content

In a composition comprising the peptide of the present disclosure or a salt thereof, or a solvate thereof, or a prodrug thereof, the content of the peptide of the present disclosure or a salt thereof, or a solvate thereof, or a prodrug thereof can vary depending on the form of the composition, but can be, for example, about 0.1 to 100% by weight, about 0.5 to 50% by weight, about 1 to 30% by weight, about 5 to 20% by weight, about 10 to 99.9% by weight, about 20 to 90% by weight, about 0.1% by weight, about 0.2% by weight, about 0.5% by weight, about 1% by weight, about 2% by weight, about 5% by weight, about 10% by weight, about 20% by weight, or about 50% by weight with respect to the entire composition. The content of components other than the peptide of the present disclosure or a salt thereof, or a solvate thereof, or a prodrug thereof can vary depending on the form of the composition, but can be, for example, about 10 to 99.9% by weight or about 20 to 90% by weight with respect to the entire composition.

Dosing Regimen

The peptide of the present disclosure or a salt thereof, or a solvate thereof, or a prodrug thereof, or a composition comprising the same can be administered, for example, at a dose of about 0.005 to 50 mg, about 0.05 to 10 mg, or about 0.2 to 4 mg as the peptide of the present disclosure per 1 kg of body weight per day in a single or multiple administrations. The peptide of the present disclosure or a salt thereof, or a solvate thereof, or a prodrug thereof, or a composition or kit comprising the same can be administered at any suitable dosing frequency such as three times daily, twice daily, once daily, every other day, once every three days, once every four days, once every five days, biweekly, once every two weeks, once every three weeks, once every four weeks, once every two months, once every three months, once every four months, once every five months, once every six months, or once a year.

Route of Administration

A composition comprising the peptide of the present disclosure or a salt thereof, or a solvate thereof, or a prodrug thereof can be administered through any suitable route of administration, such as intravenous, topical intramuscular, subcutaneous, intradermal, transdermal, rectal, vaginal, oral mucosal, pulmonary mucosal, transnasal, transocular, or oral (enteric) route.

Dosage Form

A composition comprising the peptide of the present disclosure or a salt thereof, or a solvate thereof, or a prodrug thereof can be formulated into any suitable dosage form such as a solution, injection, patch, microneedle, suppository, sustained release agent, tablet (including sugar-coated tablet and film-coated tablet), powder, granule, and capsule (including soft capsule).

Combination

The peptide of the present disclosure or a salt thereof, or a solvate thereof, or a prodrug thereof can be used in combination with any suitable agent. Examples of such an agent include endocrine therapeutic drugs, chemotherapeutic agents, immunotherapeutic agents (BRM), cell growth factors, agents that inhibit the action of a cell growth factor, and the like.

Examples of endocrine therapeutic agents include fosfestrol, diethylstilbestrol, chlorotrianiserin, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogen (e.g., tamoxifen citrate, toremifene citrate, and the like), pill formulations, mepitiostane, testololactone, aminoglutethimide, LH-RH agonists (e.g., goserelin acetate, buserelin, leuprorelin, and the like), droloxiphene, epitiostanol, ethinylestradiol sulfonate, aromatase inhibitors (e.g., fadrozole hydrochloride, anastrozole, letrozole, exemestane, vorozole, formestane, and the like), antiandrogens (e.g., flutamide, bicalutamide, nilutamide, and the like), 5α-reductase inhibitors (e.g., finasteride, epristeride, and the like), adrenocortical hormonal agents (e.g., dexamethasone, prednisolone, betamethasone, triamcinolone, and the like), androgen synthesis inhibitors (e.g., abiraterone and the like), retinoids, drugs that slow the metabolism of retinoids (e.g., liarozole), and the like.

Examples of chemotherapeutic agents include alkylating agents, antimetabolites, anticancer antibiotics, plant derived anticancer agents, and the like.

Examples of alkylating agents include nitrogen mustard, nitrogen mustard-N-oxide hydrochloride, chlorambucil, cyclophosphamide, ifosfamide, thiotepa, carboquone, improsulfan tosilate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulfan, trofosfamide, zinostatin stimalamer, carboquone, adozelesin, cystemustine, bizelesin, and the like.

Examples of antimetabolites include mercaptopurine, 6-mercaptopurine riboside, thioinosine, methotrexate, enocitabine, cytarabine, cytarabine ocphosphate, ancitabine hydrochloride, 5-FU agents (e.g., fluorouracil, tegafur, UFT, doxifluridine, carmofur, galocitabine, emitefur, and the like), aminopterin, leucovorin calcium, tabloid, butocin, calcium folinate, calcium levofolinate, cladribine, emitefur, fludarabine, gemcitabine, hydroxycarbamide, pentostatin, piritrexim, idoxuridine, mitoguazone, tiazofurin, ambamustine, and the like.

Examples of anticancer antibiotics include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride, and the like.

Examples of plant derived anticancer agents include etoposide, etoposide phosphate, vinblastine sulfate, vincristine sulfate, vindesine sulfate, teniposide, paclitaxel, docetaxel, vinorelbine, and the like.

Examples of immunotherapeutic agents (BRM) include picibanil, krestin, sizofiran, lentinan, ubenimex, interferon, interleukin, macrophage colony-stimulating factor, granulocyte colony-stimulating factor, lymphotoxin, BCG vaccine, *Corynebacterium parvum*, levamisole, polysaccharide K, procodazole, and the like.

A cell growth factor is typically a peptide having a molecular weight of 20,000 or less, which is an agent exerting action at a low concentration by binding with a receptor. Examples thereof include (1) EGF or substances having substantially the same activity as EGF (e.g., EGF (epidermal growth factor), heregulin (HER3 and HER4 ligands), and the like), (2) insulin or substances having substantially the same activity as insulin (e.g., insulin, IGF (insulin-like growth factor)-1, IGF-2, and the like), (3) FGF (fibroblast growth factor) or substances having substantially the same activity as FGF (e.g., acidic FGF, basic FGF, KGF(keratinocyte growth factor), FGF-10, and the like), and (4) other cell growth factors (e.g., CSF (colony-stimulating factor), IL-2, NGF (nerve growth factor), PDGF (platelet-derived growth factor), TGF-β (transforming growth factor R), HGF (hepatocyte growth factor), VEGF (vascular endothelial growth factor)), and the like.

Examples of agents inhibiting the action of a cell growth factor include Herceptin (HER2 receptor antibody) and the like.

Examples of other agents that can be used in combination with the peptide of the present disclosure or a salt thereof, or a solvate thereof, or a prodrug thereof include L-asparaginase, aceglatone, procarbazine hydrochloride, protoporphyrin-cobalt complex salt, mercury hematoporphyrin sodium, type I topoisomerase inhibitors (e.g., irinotecan, topotecan, and the like), type II topoisomerase inhibitors (e.g., sobuzoxane and the like), lyase inhibitors, endothelin antagonists (e.g., ABT-627 and the like), differentiation inducing agents (e.g., retinoid, vitamin Ds, and the like), angiogenesis inhibitors, α-blockers (e.g., tamsulosin hydrochloride and the like), insulin resistance improving agents (e.g., pioglitazone hydrochloride, rosiglitazone (maleate), GI-262570, JTT-501, MCC-555, YM-440, KRP-297, CS-011, FK-614, (E)-4-[4-(5-methyl-2-phenyl-4-oxazolylmethoxy)benzyloxyimino]-4-phenylbutyric acid, angiotensin II antagonists (e.g., losartan, eprosartan, candesartan, cilexetil, valsartan, telmisartan, irbesartan, tasosartan, olmesartan and their active metabolites (such as candesartan), and the like), cancer antigens, DNAs, lectins, carbohydrates, lipids, and the like.

When using the peptide of the present disclosure or a salt thereof, or a solvate thereof, or a prodrug thereof with an agent used in combination, the timing of administration thereof is not limited. They can be administered simultaneously or differentially. The dosage of the peptide of the present disclosure or a salt thereof, or a prodrug thereof can be appropriately determined depending on the subject of administration, route of administration, disease, combination, or the like.

The administration manner of the peptide of the present disclosure or a salt thereof, or a solvate thereof, or a prodrug thereof and the agent used in combination is not particularly limited. Examples thereof include administration of a single formulation obtained by formulating them together, administration of two or more formulations obtained by independently formulating them via the same or different routes of administration simultaneously or differentially.

As used herein, "or" is used when "at least one or more" of the listed matters in the sentence can be employed. When explicitly described herein as "within the range" of "two values", the range also includes the two values themselves.

(General Technology)

Any molecular biological methodologies, biochemical methodologies, microbiological methodologies, and bioinformatics that is known in the art, well known, or conventional can be used herein.

Reference literatures such as scientific literatures, patents, and patent applications cited herein are incorporated herein by reference to the same extent that the entirety of each document is specifically described.

As described above, the present disclosure has been described by showing preferred embodiments to facilitate understanding. The present disclosure is described hereinafter based on Examples. The above descriptions and the following Examples are not provided to limit the present disclosure, but for the sole purpose of exemplification. Thus, the scope of the present invention is not limited to the embodiments and Examples specifically described herein and is limited only by the scope of claims.

EXAMPLES

The Examples are described hereinafter. For reagents, the specific products described in the Examples were used. However, the reagents can be substituted with an equivalent product from another manufacturer (Sigma-Aldrich, Fujifilm Wako Pure Chemical, Nacalai Tesque, R & D Systems, USCN Life Science Inc., or the like).

Example 1: Synthesis of Peptides

The following peptides were synthesized (nomenclature of each compound is shown within the parenthesis)

```
                                                          [SEQ ID NO: 9]
Ac-SCHFGPLTWVCK-NH2 (YS12)

(SEQ ID NO: 16)
(benzoyl)-SCHFGPLTWVCK-NH2 (GT11255)

(SEQ ID NO: 17)
(p-fluaraphenylacetyl)-SCHFGPLTWVCK-NH2 (GT-11256)

(SEQ ID NO: 18)
(propionyl)-SCHFGPLTWVCK-NH2 (GT-11257)

(SEQ ID NO: 19)
Ac-SCH(p-fluoro-Phe)GPLTWVCK-NH2 (GT-11258)

(SEQ ID NO: 20)
Ac-SCH(p-chloro-Phe)GPLTWVCK-NH2 (GT-11259)

(SEQ ID NO: 21)
Ac-SCH(m-chloro-Phe)GPLTWVCK-NH2 (GT-11260)

[SEQ ID NO: 10]
Ac-SCHYGPLTWVCK-NH2 (Gt11261)

(SEQ ID NO: 22)
Ac-SCH(phenylglycine)GPLTWVCK-NH2 (GT-11262)

(SEQ ID NO: 23)
Ac-SCH(phenethylglycine)GPLTWVCK-NH2 (GT-11263)

[SEQ ID NO: 11]
Ac-SCHFAPLTWVCK-NH2 (GT-11264)

(SEQ ID NO: 24)
Ac-SCHFaPLTWVCK-NH2 (GT-11265)

[SEQ ID NO: 121]
Ac-SCHFGALTWVCK-NH2 (GT-11266)

(SEQ ID NO: 25)
Ac-SCHFG(homoproline)LTWVCK-NH2 (GT-11267)

[SEQ ID NO: 13]
Ac-SCHFGPATWVCK-NH2 (GT-11268)

[SEQ ID NO: 14]
Ac-SCHFGPMTWVCK-NH2 (GT-11269)
```

-continued

Ac-SCHFGPLTMVCK-NH$_2$ (GT-11270) [SEQ ID NO: 15]

Ac-SCHFGPLT(β-homotryptophan)VCK-NH$_2$ (GT-11271) (SEQ ID NO: 26)

Ac-SCHFGPLT(α-naphthylalanine)VCK-NH$_2$ (GT-11272) (SEQ ID NO: 27)

Ac-SCHFGPLT(β-naphthylallanine)VCK-NH$_2$ (GT-11273) (SEQ ID NO: 28)

Ac-SCHFGPLT(8-quinolylalanine)VCK-NH$_2$ (GT-11274) (SEQ ID NO: 29)

Ac-SCHFGPLT(6-chloro-Trp)VCK-NH$_2$ (GT-11275) (SEQ ID NO: 30)

Ac-SCHFGPLT(5-chloro-Trp)VCK-NH$_2$ (GT-11276) (SEQ ID NO: 31)

Ac-SCHFGPLTWV(homocysteine)K-NH$_2$ (GT-11277) (SEQ ID NO: 32)

Ac-SCHFGPLTWV(penicillamine)K-NH$_2$ (GT-11278) (SEQ ID NO: 33)

Ac-kcvwtlpGfhcs-NH$_2$ (GT-11279) (SEQ ID NO: 34)

Ac-kcvwtlGGfhcs-NH$_2$ (GT-11280) (SEQ ID NO: 35)

Ac-SCH(3,4-difluoro-Phe)GPLT(8-quinolylalanine)VCK-NH$_2$ (GT-11303) (SEQ ID NO: 36)

Ac-SCH(3,4-difluoro-Phe)GPLT(2-quinolylalanine)VCK-NH$_2$ (GT-11304) (SEQ ID NO: 37)

Ac-SCH(3,4-difluoro-Phe)GPLT(2-benzothiazolylalanine)VCK-NH$_2$ (GT-11305) (SEQ ID NO: 38)

Ac-SCH(p-fluoro-Phe)GPLT(2-quinolylalanine)VCK-NH$_2$ (GT-11306) (SEQ ID NO: 39)

Ac-SCH(p-fluoro-Phe)GPLT(2-benzothiazolylalanine)VCK-NH$_2$ (GT-11307) (SEQ ID NO: 40)

Ac-SCHYGPLT(2-quinolylalanine)VCK-NH$_2$ (GT-11308) (SEQ ID NO: 41)

Ac-SCHYGPLT(2-benzothiazolylalanine)VCK-NH$_2$ (GT-11309) (SEQ ID NO: 42)

Synthesis, purification, and analysis of the peptides described above were commissioned to GlyTech, Inc. (Osaka, Japan). Naturally-occurring amino acids were purchased from Merck (Germany) (Novabiochem®), etc., and non-naturally-occurring amino acids were purchased from Watanabe Chemical, etc. Amino acids (including non-naturally-occurring amino acids) for synthesizing the peptides described above and protected amino acids thereof are available from any suitable supplier. Rink Amide ChemMatrix (Biotage, Sweden) was used as the starting material to synthesize a protected peptide resin of interest by sequentially extending amino acids from the resin according to the sequences described above by a condensation reaction in accordance with a program with a peptide automatic synthesizer (Prelude (Gyros Protein Technologies)). After the completion of construction of a peptide on the resin, the protected peptide resin was dried. The resulting protected peptide was treated with trifluoroacetic acid to cleave the protecting group and the resin carrier. The crude peptide obtained after cleavage from the resin carrier was purified with an HPLC system; Prominence UFLC (Shimadzu Corporation, Kyoto, Japan) or LaChrom Elite (Hitachi High-Technologies Corporation, Tokyo, Japan). The solvent condition used at the time was A/B gradient, with mobile phase A: aqueous 0.1% TFA solution and mobile phase B: 0.09% TFA/10% H$_2$O/90% MeCN. The purified peptide (reduced) was converted into a raw peptide (oxidized) by iodine treatment to allow formation of a disulfide bond.

Mass spectrometry was performed on each synthesized peptide to confirm that a desired structure was obtained (FIGS. 1 to 33). Mass spectrometry was performed using Synapt HDMS (Waters, USA) by infusion.

The peptides synthesized above were exposed to human liver cancer HepG2 cells and the leakage of granules under a microscope was studied. While a relatively low degree of granule leakage was observed for GT-11259 and GT-11260, a significant granule leakage was observed for GT-11258, GT-11261, and GT-11274. In view of the above, peptides GT-11258, GT-11261, and GT-11274 were expected to have a relatively strong activity.

Example 2: In Vitro Efficiency Evaluation in Human Liver Cancer Cells

The efficiency of the synthesized peptides was measured by the following method.

Lethal effect due to a synthetic peptide using human liver cancer derived HepG2 cells Tests were conducted on the following test compounds: YS12, GT-11268, GT-11261, GT-11274, GT-11259, GT-11260, GT-11280, GT-11303, GT-11304, GT-11305, GT-11306, GT-11307, GT-11308, and GT-11309.

HepG2 cells (ATCC, HB-8065) were seeded on an 8-well chamber slide (Nunc) to study the lethal effect at four concentrations of the test compounds.
Culture condition: cells were cultured under the condition of 37° C. and 5% $CO_2$-95% air using a D-MEM medium (Fujifilm Wako Pure Chemical, 045-30285) comprising 10% fetal bovine serum.
Test concentrations: 120 μM, 60 μM, 30 μM, or 15 μM of the test compounds, and PBS(−) was also used as a control.
Cell count: 1.0 to $1.5 \times 10^3$ cells were seeded in a 350 μL/well medium.
After 16 to 24 hours from starting the culture, each test compound (50 μL/well) was added and reacted for 24 hours.

The lethal effect was tested by counting the cells exhibiting positive stain with 0.1% Trypan blue solution (TB solution) and converting the value to a value per area. Specifically, the following procedures 1 to 7 were performed.
1. Culture medium was removed from the well.
2. 100 μL of the TB solution was poured into the well and reacted for 3 minutes.
3. The TB solution of 2 was removed.
4. 10 μL of Bouin solution (15 mL of saturated picric acid solution, 5 mL of undiluted formalin solution, and 1 mL of glacial acetic acid) was poured in, and reacted for 10 minutes on a mixer.
5. The reaction in 4 was attenuated with 100 μL of PBS(−) and the Bouin solution was removed.
6. 100 μL of PBS(−) was added to each well.
7. TB positive cells within one segment (1 $mm^2$) were counted under a microscope (inverted phase contrast microscope, Nikon), and the mean for 10 segments was calculated.

As a result, the results shown in FIGS. 34 to 37 were obtained. Each of the peptides GT-11268, GT-11261, GT-11274, GT-11259, GT-11260, GT-11280, GT-11303, GT-11304, GT-11305, GT-11306, GT-11307, GT-11308, and GT-11309 exhibited a HepG2 cell killing effect that is equivalent or greater than that of YS12. In particular, the effect of the peptides GT-11261, GT-11259, and GT-11303 to GT-11308 was potent. In view of the above, these peptides are expected to be advantageously usable, for example, in applications for treating proliferative diseases (e.g., cancer and adenomyosis) and diabetic retinopathy.

Example 3: In Vitro Efficiency Evaluation in Human Pancreatic Cancer Cells

The in vitro efficiency of the synthesized peptides against human pancreatic cancer cells was evaluated by the following method.

Human pancreatic cancer derived AsPC-1 cells (ECACC, 96020930) were passaged (twice/week) under the condition of 37° C. and 5% $CO_2$-95% air using an RPMI-1640 medium (Sigma, R8758-500 ML) comprising 10% fetal bovine serum (biowest, S182H-500) and 1 mM sodium pyruvate (gibco, 11360-070). The AsPC-1 cells were collected from a culture dish using 0.05% trypsin-0.02% EDTA solution (Sigma, T4174-100 ML). The cells were suspended in the medium and then seeded on a 96-well microplate ($3 \times 10^3$/0.05 mL/well). After culturing the cells overnight, a medium comprising the test compounds (total of 43 compounds, final concentration of 150 μM) was added (0.05 mL/well, 3 wells/test compound). After 72 hours, the cell proliferation capability for each well was measured by a WST assay (DOJINDO LABORATORIES, Cell Counting Kit-8), and the inhibition ratio for each test compound against the control (test compound-free well) was calculated.

A WST assay is a viable cell count measuring method, which uses water-soluble tetrazolium salt WST-8 as a coloring reagent and uses water-soluble formazan generated by reduction of WST-8 as an indicator of viable cell count. NADH produced by a dehydrogenase in a cell converts WST-8 to water-soluble formazan. Since the generated water-soluble formazan has the maximum absorbance at about 450 nm, the viable cell count is indicated by measuring the absorbance at such a wavelength region. The absorbance at 450 nm was observed in the WST assay.

In this regard, additional candidate compounds GT-11332 to GT-11340 (structure of each compound is shown below) synthesized by the same method as Example 1 were prepared, and the activity of these compounds was also evaluated.

```
                                            (SEQ ID NO: 49)
Ac-SCH(4-pyridylalanine)GPLTWVCK-NH2 (GT-11332)

(SEQ ID NO: 50)
Ac-SCH(3-pyridylalanine)GPLTWVCK-NH2 (GT-11333)

(SEQ ID NO: 51)
Ac-SCH(p-methoxy-Phe)GPLTWVCK-NH2 (GT-11334)

(SEQ ID NO: 52)
Ac-SCH(m-methoxy-Phe)GPLTWVCK-NH2 (GT-11335)

(SEQ ID NO: 53)
Ac-SCH(m-hydroxy-Phe)GPLTWVCK-NH2 (GT-11336)

(SEQ ID NO: 54)
Ac-SCH(1-naphthylalanine)GPLTWVCK-NH2 (GT-11337)

(SEQ ID NO: 55)
Ac-SCH(2-naphthylalanine)GPLTWVCK-NH2 (GT-11338)

(SEQ ID NO: 46)
Ac-SCHFGPLT(2-benzothiazolylalanine)VCK-NH2
(GT-11339)

(SEQ ID NO: 56)
Ac-SCHFGPLT(3-benzothiazolylalanine)VCK-NH2
(GT-11340)
```

Figure 38:
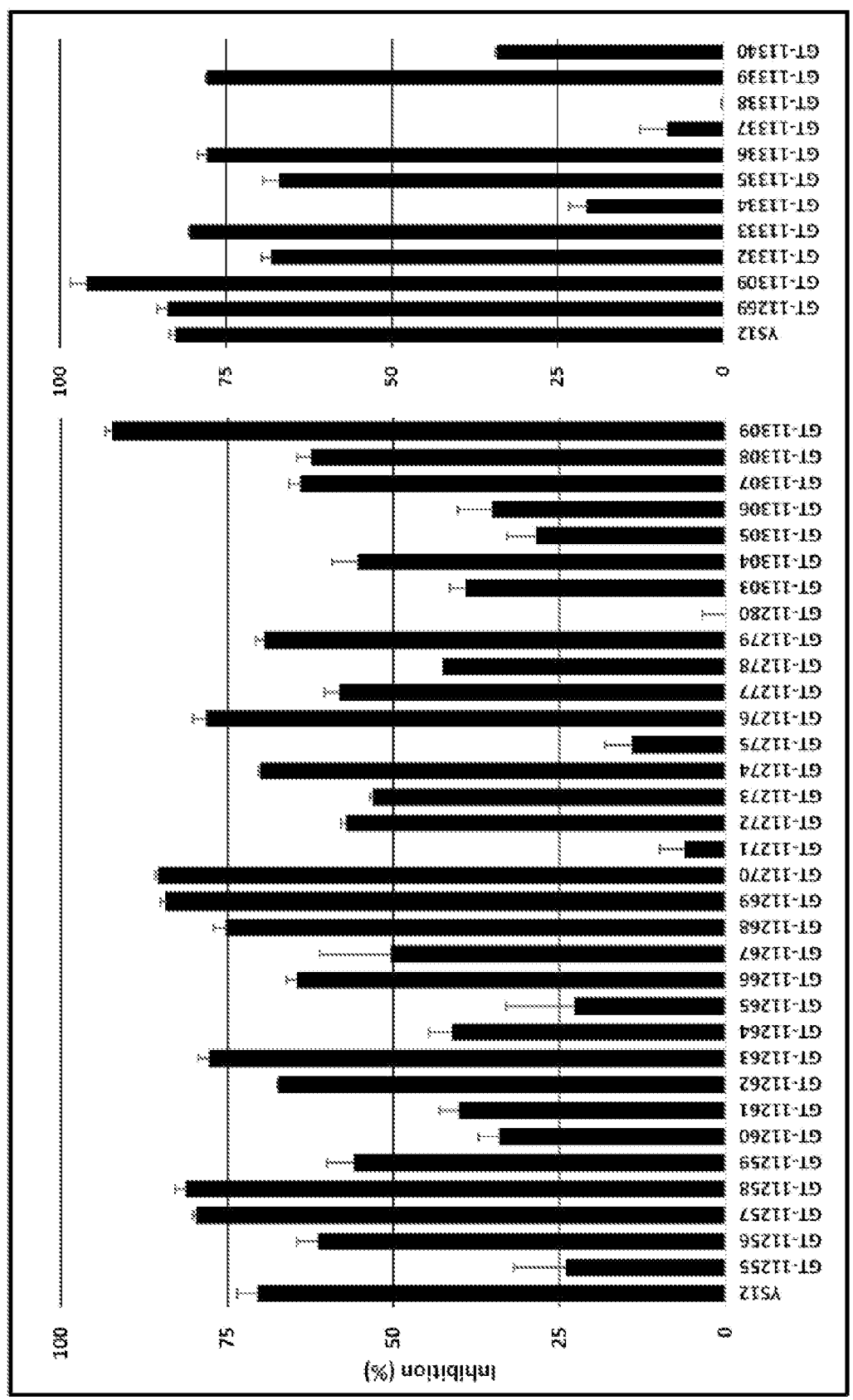
FIG. 38 shows results of evaluating the effect of various synthetic peptides on the proliferation of human pancreatic cancer derived AsPC-1 cells by a WST assay. The vertical axis indicates the inhibition ratio of each test compound against the control (test compound-free well). The horizontal axis indicates the tested agents. The results are indicated as mean±standard error of 3 wells.

As a result, the results shown in FIG. 38 were obtained. A total of 12 test compounds including GT-11257 exhibited a potent proliferation inhibiting action on AsPC-1 cells.

Example 4: In Vitro Efficiency Evaluation in Human Leukemia Cells

The in vitro efficiency of the synthesized peptides against human leukemia cells was evaluated by the following method.

Human T cell leukemia derived ATL-2 cells (provided by Dr. Maeda at the Kyoto University) were passaged (twice/week) under the condition of 37° C. and 5% $CO_2$-95% air using an RPMI-1640 medium (Sigma, R8758-500 mL) comprising 10% fetal bovine serum (biowest, S182H-500). The ATL-2 cells were collected from a culture flask. The cells were suspended in the medium and then seeded on a 96-well microplate ($3 \times 10^3/0.05$ mL/well). After culturing the cells overnight, a medium comprising the test compounds (total of 32 compounds, final concentration of 150 µM) was added (0.05 mL/well, 3 wells/test compound). After 72 hours, the cell proliferation capability for each well was measured by a WST assay (DOJINDO LABORATORIES, Cell Counting Kit-8), and the inhibition ratio for each test compound against the control (test compound-free well) was calculated.

Figure 39:
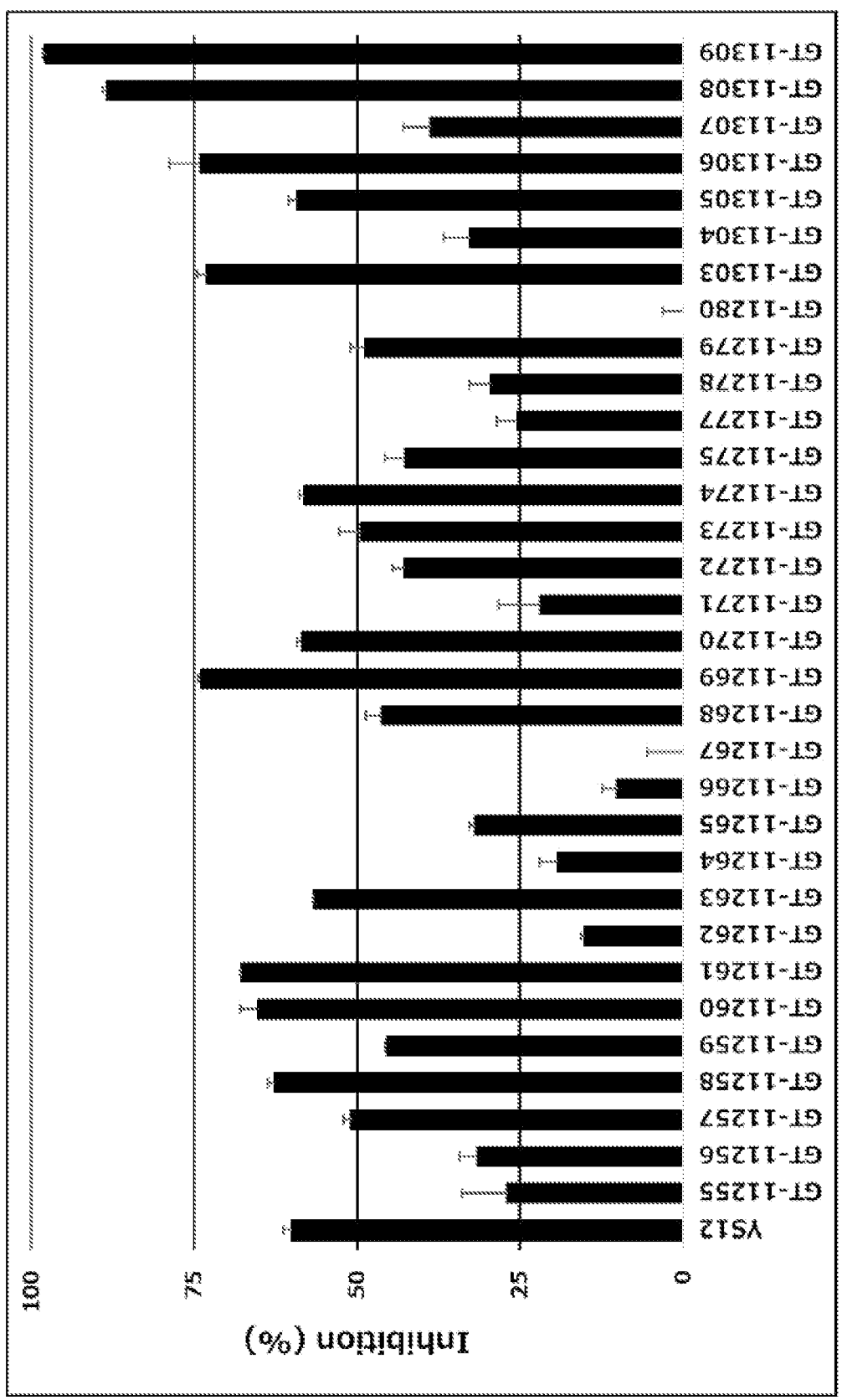
FIG. 39 shows results of evaluating the effect of various synthetic peptides on the proliferation of human leukemia derived ATL-2 cells by a WST assay. The vertical axis indicates the inhibition ratio of each test compound against the control (test compound-free well). The horizontal axis indicates the tested agents. The results are indicated as mean±standard error of 3 wells.

As a result, the results shown in FIG. 39 were obtained. In particular, GT-11269, GT-11308, GT-11309, and the like exhibited a potent proliferation inhibiting action on ATL-2 cells.

Example 5: In Vivo Peptide Efficiency Evaluation

The in vivo efficiency of the synthesized peptides was evaluated in a cancer-bearing mouse model.

Human pancreatic cancer derived AsPC-1 cells (ECACC, 96020930) were cultured and collected in the same manner as Example 3, suspended in the RPMI-1640 medium described above comprising 10% Matrigel (BD Bioscience, 354234), and transplanted subcutaneously to the right side on the back of a 6-week-old male nude mouse (SLC, BALB/cSlc-nu/nu) ($5 \times 10^6/0.1$ mL/mouse). The length (L) and width (W) of the tumor were measured using a digital caliper. When the tumor volume (V) calculated from the formula $V = L \times W^2/2$ reached about 150 to 200 $mm^3$, the mice were separated into groups and administered with test compounds (total of 8 compounds including GT-11263). Saline was administered to a control group. The compounds were administered intraperitoneally (0.1 mL/mouse, 3 to 5 mice/test compound) 3 times daily (one hour interval, a total of 0.2 mg/day), 3 times a week for 2 weeks. The tumor size and body weight were measured twice a week to monitor the status of tumor growth and the effect of the administration of test compounds.

Figure 40:
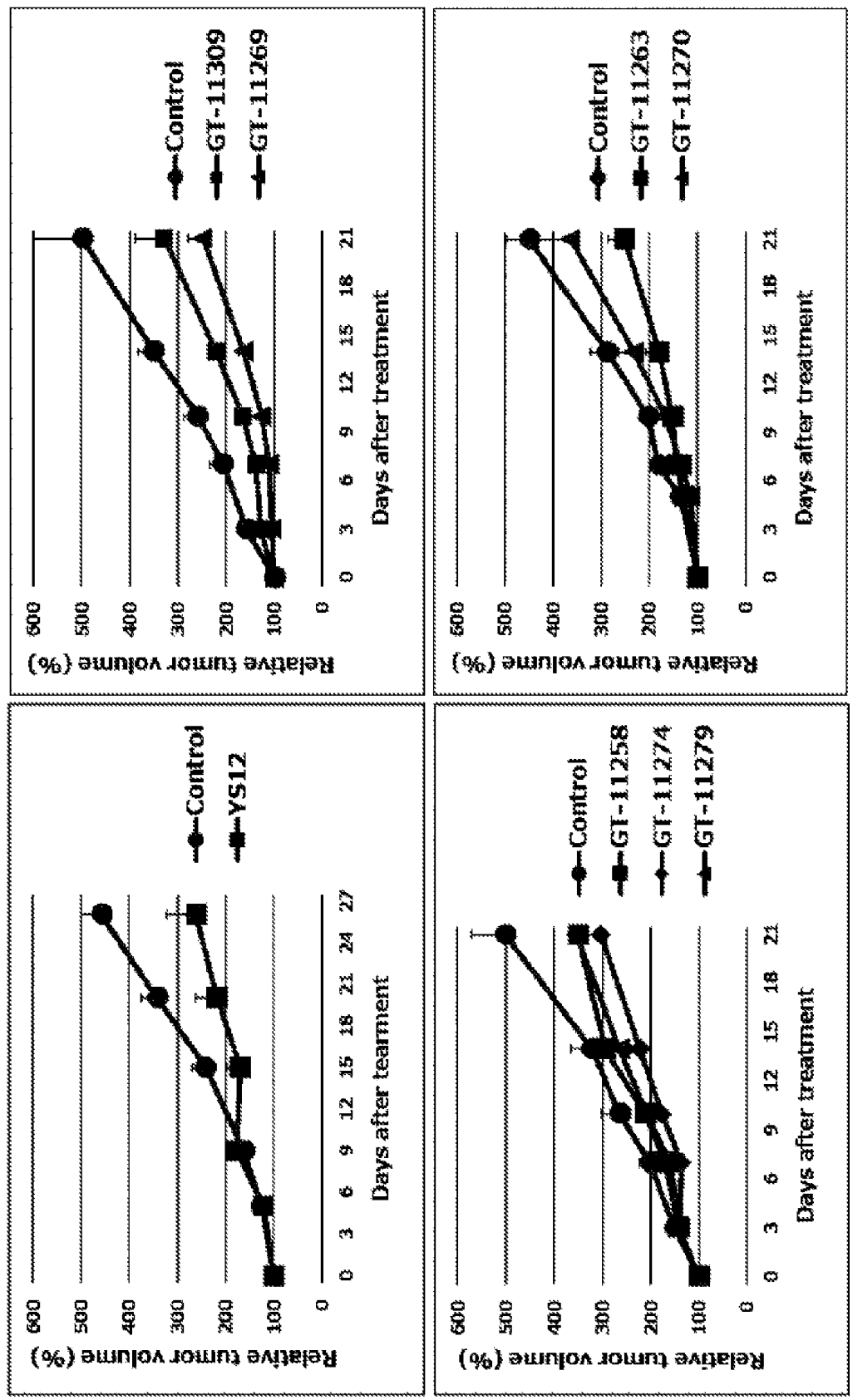
FIG. 40 shows results of evaluating the effect of various synthetic peptides on human pancreatic cancer derived AsPC-1 cancer-bearing mice. In each panel, the vertical axis indicates the relative tumor volume at each time when assuming the tumor volume as of the start of the test as 100%. The horizontal axis indicates the number of days elapsed from the administration starting date. The control is saline administration. The results are indicated as mean±standard error for 3 to 5 mice.

As a result, the results shown in FIG. 40 were obtained. A total of 3 test compounds including GT-11263 exhibited a potent antitumor effect in a cancer-bearing mouse model. None of the test compounds affected the body weight. In particular, GT-11269 and GT-11309 were potent and had an early manifestation of effect.

Example 6: Effect of Candidate Compounds on CFU-E Formation

Since GT-11269 and GT-11309 were expected to be particularly useful, the effect of these compounds on CFU-E formation was tested.

Bone marrow cells were harvested from a femur of a mouse (SLC, BALB/cSlc-nu/nu) and suspended in an α-MEM medium (Fujifilm Wako Pure Chemical, 130-18621) comprising 1.2% methylcellulose (Sigma, M0512), 30% fetal bovine serum (biowest, S182H-500), 1% bovine serum albumin (Fujifilm Wako Pure Chemical, 017-25771), 0.1 mM 2-mercaptoethanol (Fujifilm Wako Pure Chemical, 131-14572), L-glutamine (Sigma, G7513), and penicillin/streptomycin (Fujifilm Wako Pure Chemical, 168-23191), and then seeded on a 6-well microplate ($3.2 \times 10^5/2$ mL/well, 2 wells/test compound). A test compound (GT-11269 or GT-11309, final concentration of 100 µM) and recombinant human erythropoietin (Epo, 1 U/mL) were added and incubated for 72 hours. After DAB (diaminobenzidine tetrahydrochrolide, DOJINDO LABORATORIES, D006) staining, hemoglobin positive cells were counted under a microscope as CFU-E (Erythroid Colony Forming Unit).

Figure 41:
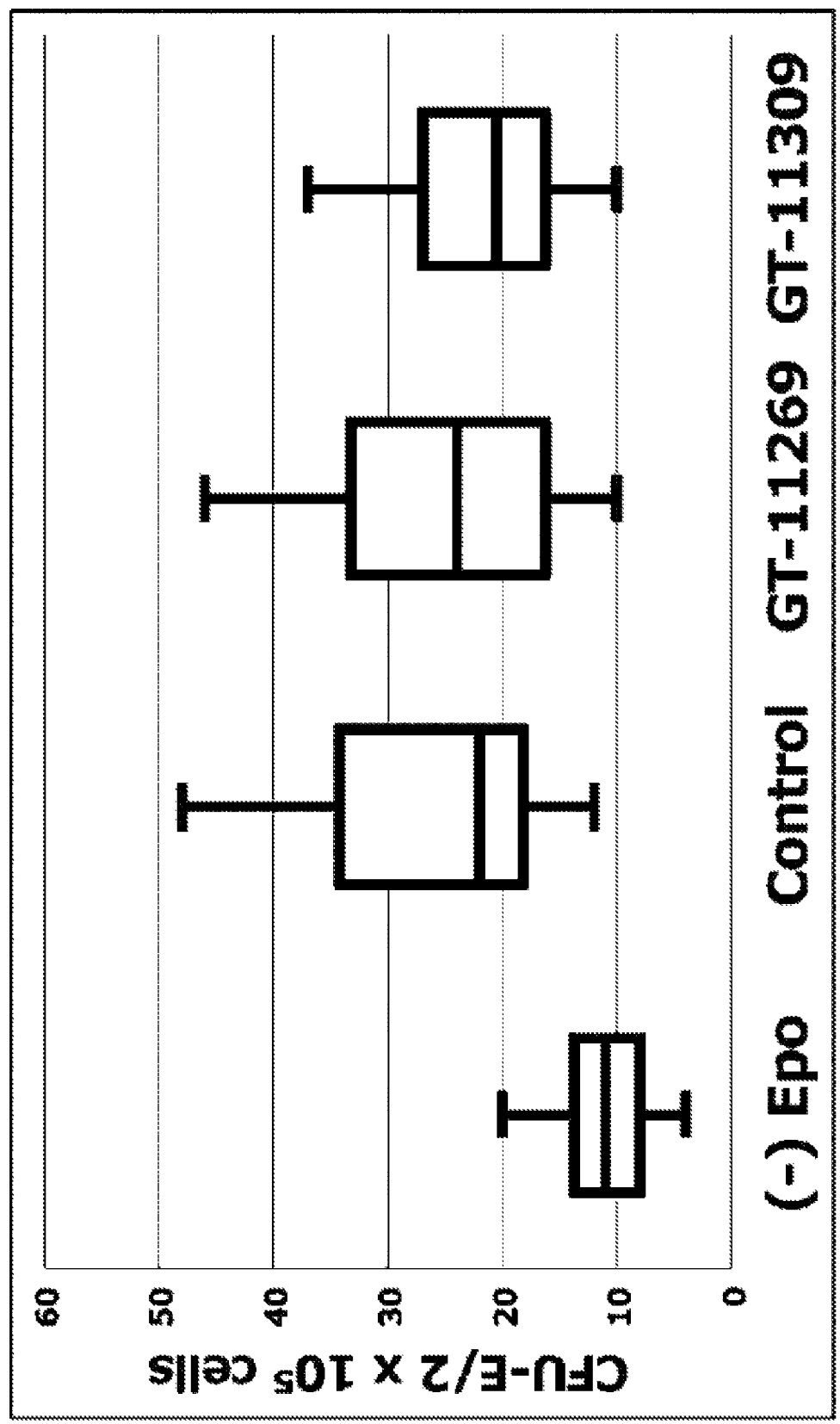
FIG. 41 shows results of evaluating the effect of each compound on CFU-E formation. The vertical axis indicates the formed CFU-E count, and the horizontal axis indicates (−) Epo: no Epo added, Control: only Epo added, GT-11269: Epo+GT-11269 (100 μM) added, and GT-11309: Epo+GT-11309 (100 μM) added. The results are shown as a box plot created with measurements from 2 wells (10 locations/well).

The results are shown in FIG. 41. CFU-E formation was promoted by recombinant human erythropoietin. Under this condition, the test compounds (GT-11269 and GT-11309) were both confirmed to have no effect on CFU-E formation.

Example 7: Effect of Candidate Compounds on Epo Dependent Cancer Cell Proliferation The effect of GT-11309, which was expected to be effective, on Epo dependent cancer cell proliferation was evaluated by the following method.

Human leukemia derived UT-7 cells (provided by Dr. Fujita at the Hokkaido University) were passaged (twice/week) under the condition of 37° C. and 5% $CO_2$-95% air using a D-MEM medium (Sigma, D5796-500 ML) comprising recombinant human erythropoietin (Epo, 2 U/mL) and 10% fetal bovine serum (biowest, S182-H-500), and cultured for a total of 9 weeks. The Epo treated UT-7 cells were washed three times and seeded on a 96-well microplate ($1 \times 10^4$/well). An anti-Epo monoclonal antibody (clone R6, provided by Dr. Masuda at the Kyoto University, 1 to 100 µg/mL), anti-EpoR monoclonal antibody (clone 713210, R&D Systems, MAB3073, 1 to 100 µg/mL) or GT-11309 (1 to 100 µM), in the presence of Epo (0 to 10 U/mL) or Epo (1 U/mL), was added. After 4 days of culture, the cell proliferation capability for each well was measured as absorbance at 450 nm by a WST assay (DOJINDO LABORATORIES, Cell Counting Kit-8).

Figure 42:
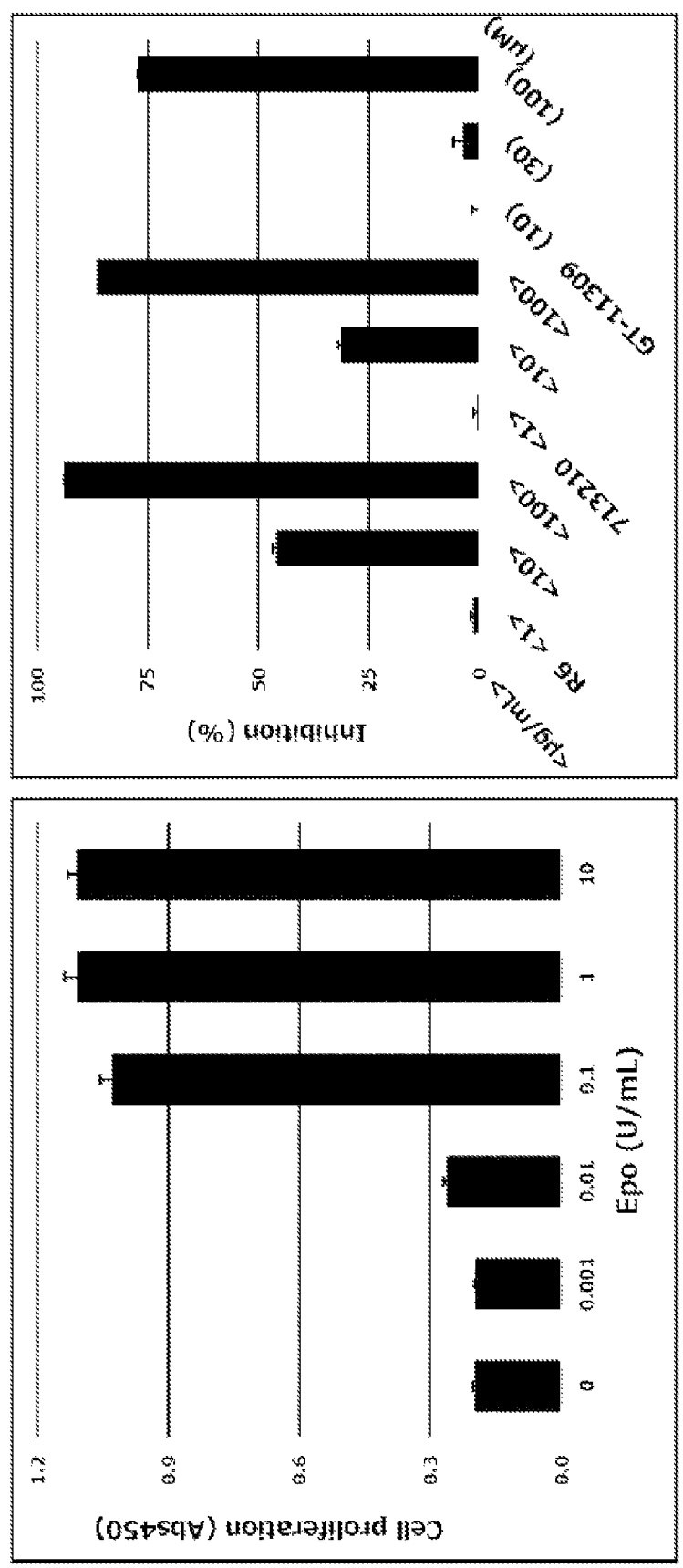
FIG. 42 shows results of evaluating the effect of GT-11309 on Epo-dependent cancer cell proliferation by a WST assay. The left panel shows the proliferation of human leukemia derived UT-7 cells in the presence of 0 to 10 U/mL of Epo, and the vertical axis indicates absorbance at 450 nm. The right panel shows the inhibition ratio of proliferation of UT-7 cells by an addition of an anti-Epo antibody (clone R6), anti-EpoR antibody (clone 713210), or GT-11309 (each antibody at 1 to 100 μg/mL, and GT-11309 at 10 to 100 μM) in the presence of 1 U/mL of Epo. The horizontal axis indicates the tested agent. The results are indicated as mean±standard error of 3 wells.

The results are shown in FIG. 42. GT-11309 suppressed Epo dependent cancer cell proliferation in the same manner as an anti-Epo antibody and anti-EpoR antibody.

It was discovered from the above findings that a mutation of $A^1$ (e.g., Tyr), mutation of $A^4$ (e.g., Met), and mutation of $A^6$ (e.g., 2-benzothiazolylalanine) in the structure of formula (I)

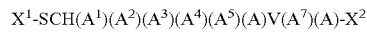
$$X^1\text{-SCH}(A^1)(A^2)(A^3)(A^4)(A^5)(A)V(A^7)(A)\text{-}X^2$$

can be particularly useful.

Example 8: Additional Candidate Compounds

Since GT-11269 and GT-11309 were expected to be particularly useful, mutations thereof were combined to create GT-11350 having the following structure by the same approach as Example 1.

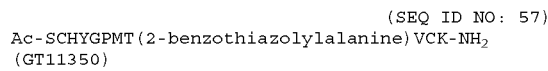

(SEQ ID NO: 57)
Ac-SCHYGPMT(2-benzothiazolylalanine)VCK-NH₂
(GT11350)

Example 8-1: In Vitro Efficiency of Peptides at Each Dose

In vitro efficiency was tested for GT-11269, GT-11309, and GT-11350 by varying the concentrations.

Human pancreatic cancer derived AsPC-1 cells (ECACC, 96020930) were cultured, collected, and seeded on a 96-well microplate ($3 \times 10^3/0.05$ mL/well) in the same manner as Example 3. After culturing the cells overnight, a medium comprising the test compounds (10, 30, or 100 μM) was added (0.05 mL/well, 3 wells/test compound). After 72 hours, the cell proliferation capability for each well was measured by a WST assay (DOJINDO LABORATORIES, Cell Counting Kit-8), and the inhibition ratio for each test compound against the control (test compound-free well) was computed.

Figure 43:
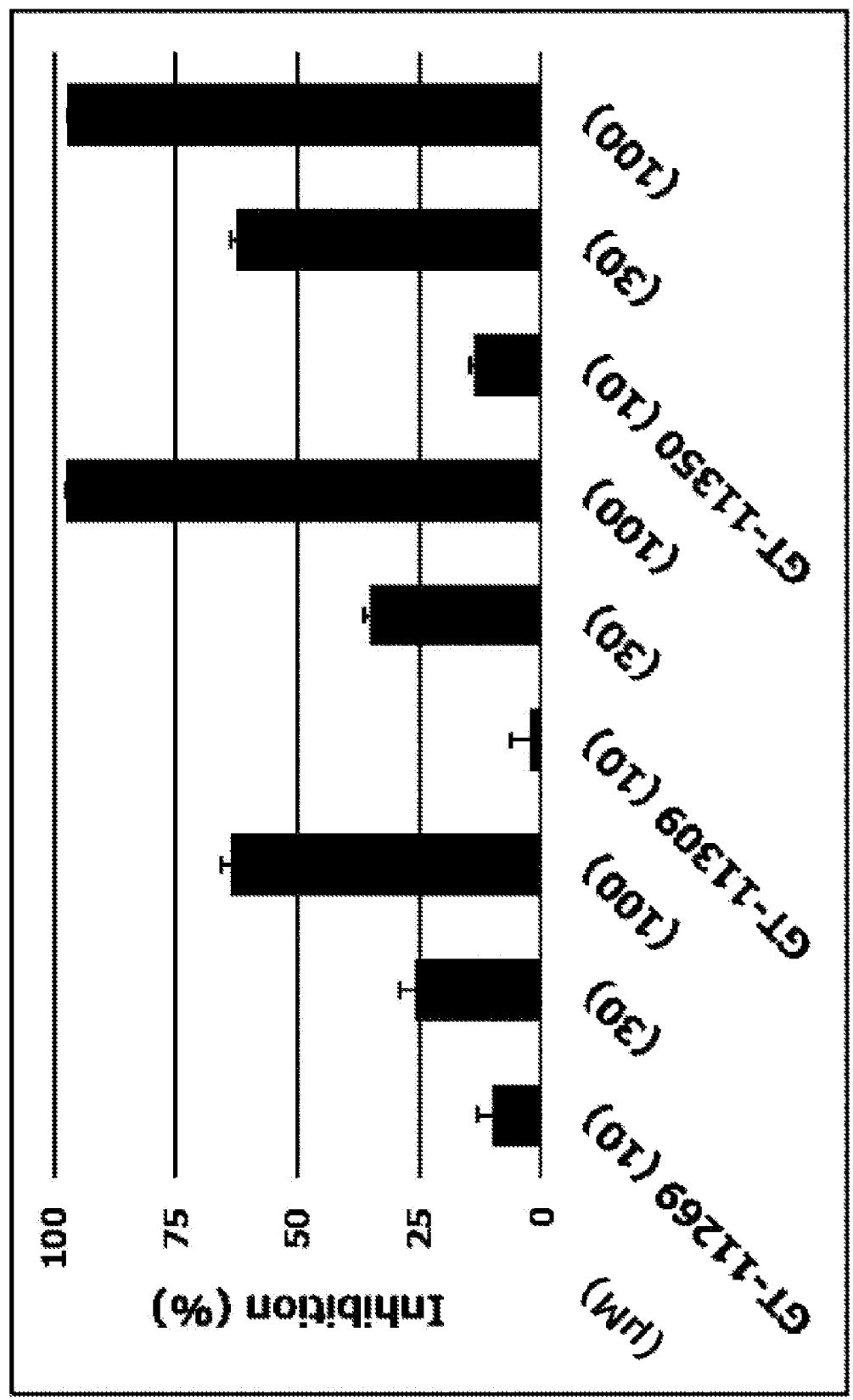
FIG. 43 shows results of evaluating the effect of GT-11269, GT-11309, and GT-11350 on the proliferation of human pancreatic cancer derived AsPC-1 cells by a WST assay. The vertical axis indicates the inhibition ratio of each test compound against the control (test compound-free well). The horizontal axis indicates the tested agent and the concentration thereof (μM). The results are indicated as mean±standard error of 3 wells.

The results are shown in FIG. 43. GT-11269, GT-11309, and GT-11350 exhibited a potent proliferation inhibiting action against AsPC-1 cells.

The proliferation suppressing capability of GT-11350 against a breast cancer cell line was also tested.

Human breast cancer derived HCC1395 cells (ATCC, CRL-2327) and HCC1806 (ATCC, CRL-2335) were cultured, collected, and seeded on a 384-well microplate ($1 \times 10^3$ and $3 \times 10^3$/0.04 mL/well). After culturing the cells overnight, a medium comprising GT-11350 (0 to 100 μM) was added (0.01 mL/well). After 72 hours, the cell proliferation capability for each well against the control (test compound-free well) was calculated using the amount of ATP as an indicator, which was measured using CellTiter-Glo 2.0 (Promega, G9242).

Figure 44:
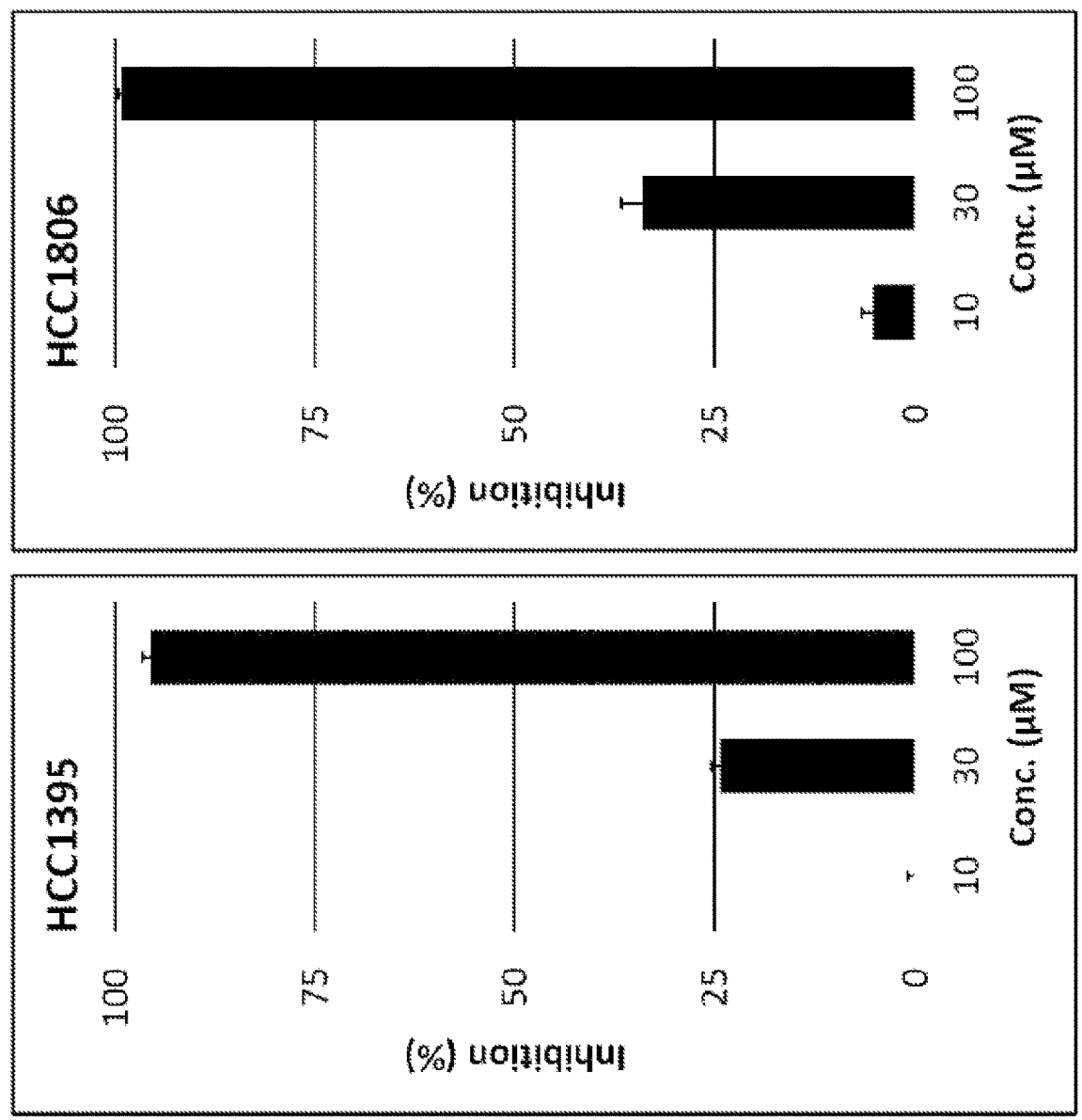
FIG. 44 shows results of evaluating the effect of GT-11350 on the proliferation of human breast cancer cells using the amount of ATP as an indicator. Each panel shows results for HCC1395 (left) and HCC1806 (right). In each panel, the vertical axis indicates the inhibition ratio against the control (test compound-free well) at each concentration. The horizontal axis indicates the tested concentration (1M). The results are indicated as mean±standard error of 3 wells.

The results are shown in FIG. 44. GT-11350 also exhibited proliferation suppressing capability against a breast cancer cell line.

Example 8-2: In Vivo Efficiency

The in vivo efficiency of synthesized peptides was evaluated in a cancer-bearing mouse model.

In the same manner as Example 5, human pancreatic cancer derived AsPC-1 cells were transplanted subcutaneously to the right side on the back of a 6-week-old male nude mouse (SLC, BALB/cSlc-nu/nu) ($5 \times 10^6$/0.1 mL/mouse). The length (L) and width (W) of the tumor were measured using a digital caliper. When the tumor volume (V) calculated from the formula $V = L \times W^2/2$ reached about 150 to 200 mm$^3$, the mice were separated into groups and administered with test compounds (GT-11269, GT-11309, and GT-11350). Saline was administered to a control group. The compounds were administered intraperitoneally (0.1 mL/mouse, 5 mice/test compound) 3 times daily (one hour interval, a total of 0.5 mg/day), twice a week for 4 weeks. The tumor size and body weight were measured twice a week to monitor the effect of the administration of test compounds (FIG. 45).

Figure 46:
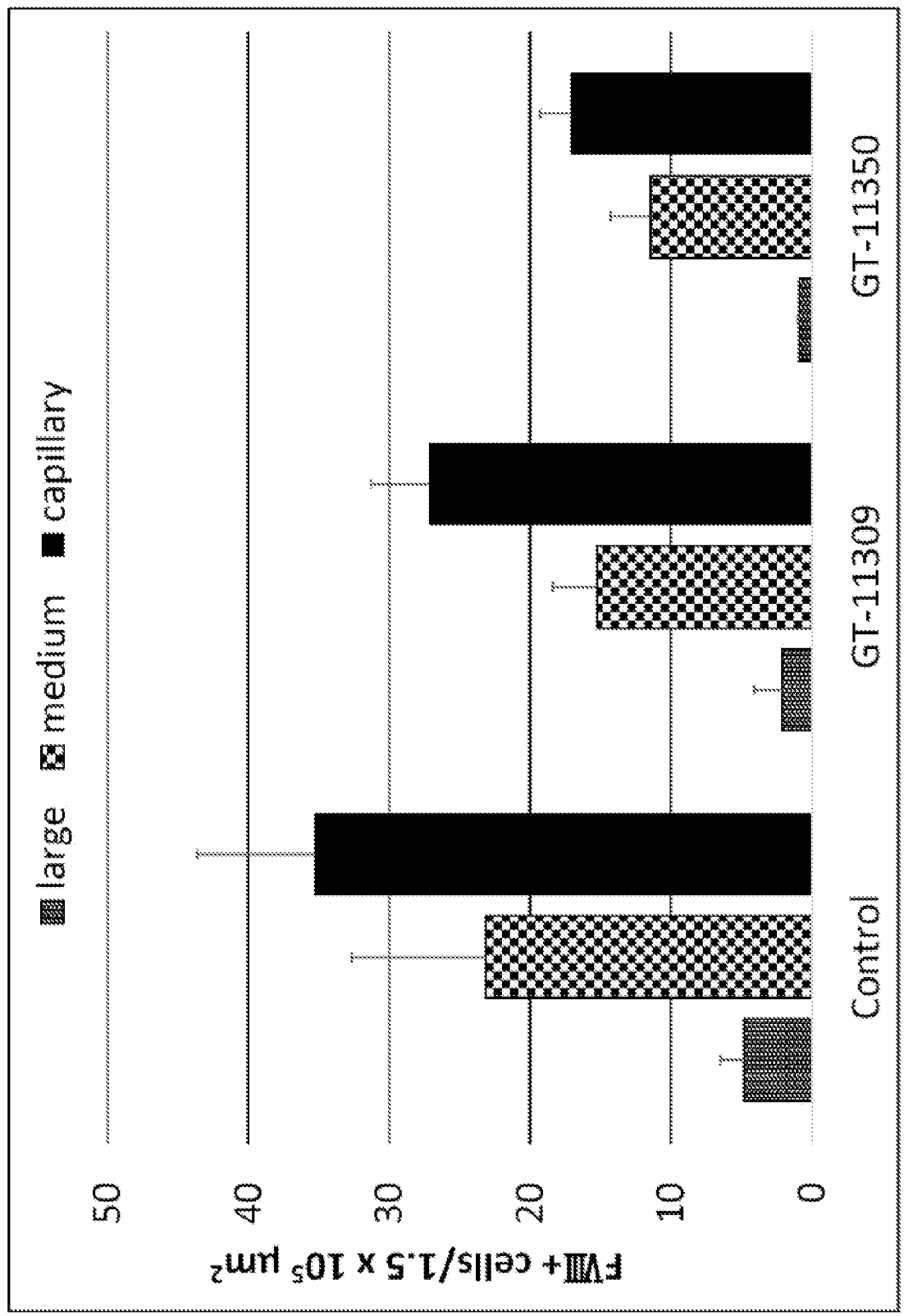
FIG. 46 shows results of evaluating the effect of synthetic peptides on human pancreatic cancer derived AsPC-1 cancer-bearing mice. The vertical axis indicates the FVIII positive cell count per tumor tissue volume by cell size. The horizontal axis indicates the cell sizes of φ (cell size)>50 μm (large), 50 μm>φ>10 μm (medium), 10 μm>φ (capillary). The results are indicated as mean±standard error for 3 to 4 mice.

Tumor tissue was removed on day 6 from the final administration from an AsPC-1 cancer-bearing mouse administered with GT-11309 or GT-11350 by the same protocol, and a portion thereof was fixed with a Zamboni solution and then a frozen segment was prepared. The positive cell count was measured by an immunohistochemical method using an anti-factor VIII (FVIII) related antigen antibody to study the action of the test compounds on angiogenesis within the tumor tissue (FIG. 46).

Blood was drawn on day 6 from the final administration from an AsPC-1 cancer-bearing mouse administered with GT-11269, GT-11309, or GT-11350 by the same protocol, and the hematocrit value was measured by the capillary method using a high speed centrifuge. The blood hemoglobin concentration was also measured using a commercially available measurement kit (BioAssay Systems, DIHB-250) (FIG. 47).

Figure 48:
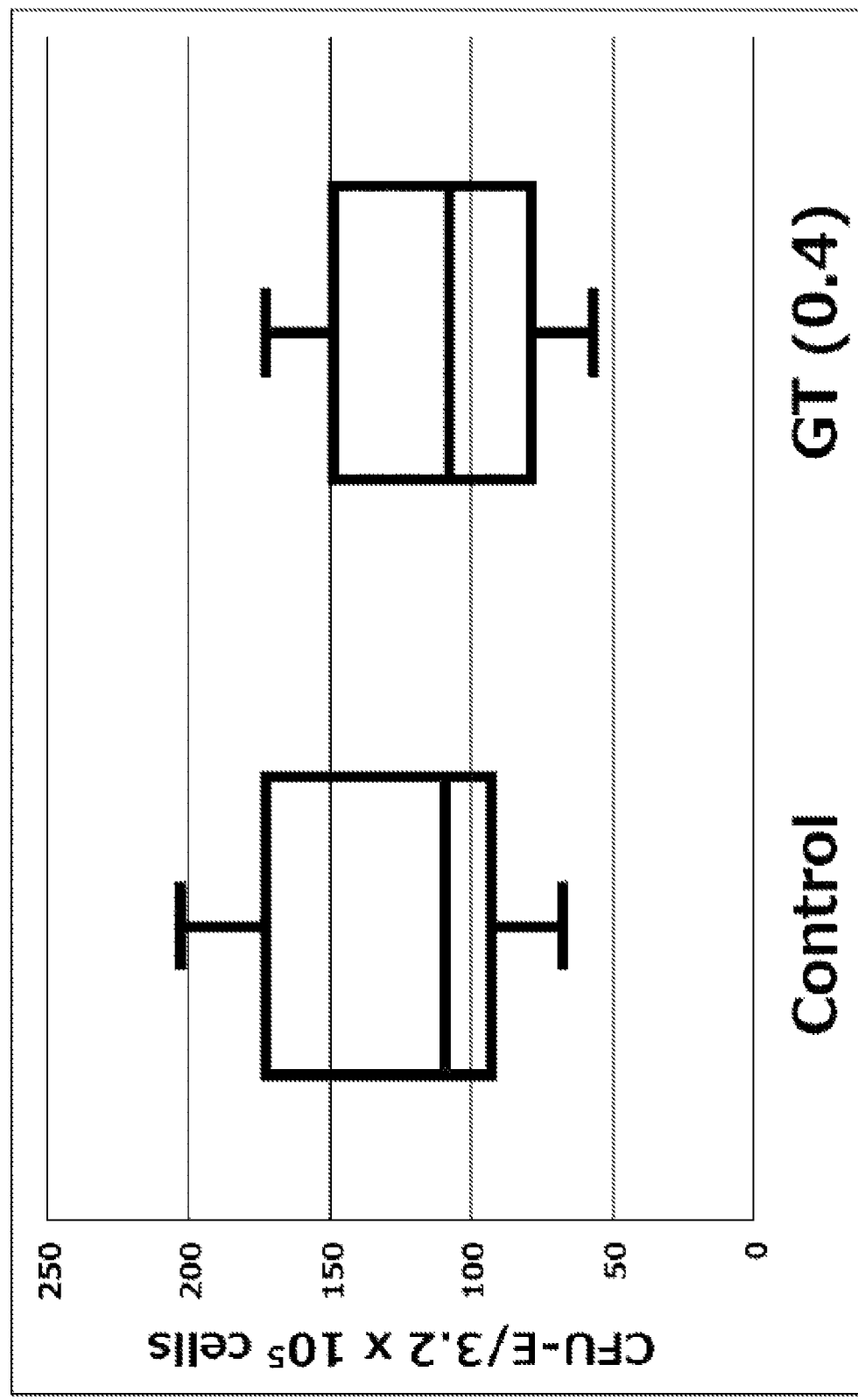
FIG. 48 shows results of evaluating the effect of GT-11350 on CFU-E formation. The vertical axis indicates the formed CFU-E count, and the horizontal axis indicates the test compounds. The results are shown as a box plot created with measurements from 2 wells (10 locations/well).

Furthermore, CFU-E formation was evaluated. Bone marrow cells were harvested from a femur of an AsPC-1 cancer-bearing mouse administered with GT-11350 3 times daily (one hour interval, a total of 0.4 mg/day), twice a week for 4 weeks. Saline was administered to a control group. In the same manner as Example 6, bone marrow cells harvested from the mouse were suspended and seeded on a 6-well microplate ($3.2 \times 10^5$/2 mL/well). Recombinant human erythropoietin (Epo, 1 U/mL) was added to the plate and incubated for 2 days. After DAB (diaminobenzidine tetrahydrochrolide, DOJINDO LABORATORIES, D006) staining, hemoglobin positive cells were counted under a microscope as CFU-E (Erythroid Colony Forming Unit) (FIG. 48).

In FIG. 45, each of the test compounds exhibited an anti-tumor effect in a cancer-bearing mouse model, but the compounds did not affect the body weight. In FIG. 46, the FVIII positive cell count in each test compound administered group decreased compared to the FVIII positive cell count in the control group, so that each of the test compounds exhibited an angiogenesis suppressing action. In FIG. 47, none of the test compounds affected the hematocrit value and blood hemoglobin concentration. In FIG. 48, CFU-E formation was not inhibited in a mouse administered with GT-11350.

Example 9: Analysis on Dosage and Administration

Dosage and administration of GT-11350 were analyzed.

In the same manner as Example 5, human pancreatic cancer derived AsPC-1 cells were transplanted subcutaneously to the right side on the back of a 6-week-old male nude mouse (SLC, BALB/cSlc-nu/nu), and when the tumor volume (V) reached about 150 to 200 mm$^3$, the mice were separated into groups and administered with test compounds (GT-11350). Saline was administered to a control group. The compounds were administered intraperitoneally (0.1 mL/mouse) 3 times daily (one hour interval, a total of 0.1 mg, 0.2 mg, or 0.4 mg/day), twice a week for 4 weeks. The tumor size and body weight were measured twice a week to monitor the effect of the dose of test compounds (FIG. 49).

Blood was drawn on day 4 from the final administration from an AsPC-1 cancer-bearing mouse administered with GT-11350 by the same protocol, and the hematocrit value was measured by the capillary method using a high speed centrifuge. The blood hemoglobin concentration was also measured using a commercially available measurement kit (BioAssay Systems, DIHB-250) (FIG. 50).

Figure 49:
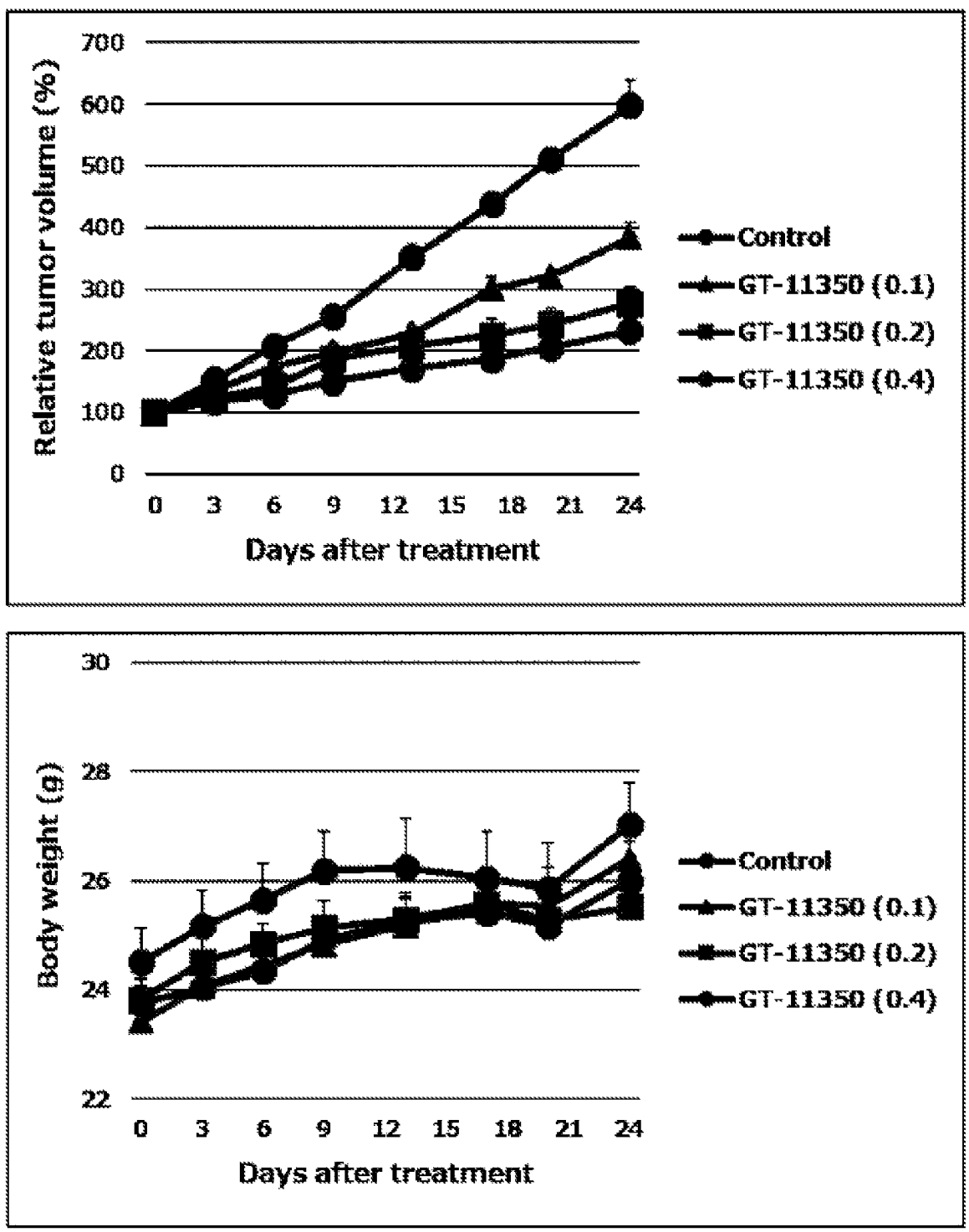
FIG. 49 shows results of evaluating the effect of GT-11350 at each dose (0.1 mg, 0.2 mg, and 0.4 mg/day) on human pancreatic cancer derived AsPC-1 cancer-bearing mice. In the top panel, the vertical axis indicates the relative tumor volume at each time when assuming the tumor volume as of the start of the test as 100%. The horizontal axis indicates the number of days elapsed from the administration starting date. In the bottom panel, the vertical axis indicates the body weight at each time, and the horizontal axis indicates the number of days elapsed from the administration starting date. The control is saline administration. The results are indicated as mean±standard error for 6 mice.

In FIG. 49, GT-11350 exhibited a dose dependent antitumor effect, but the body weight was not affected. In FIG. 50, none of the doses had an effect on the hematocrit value or the blood hemoglobin concentration.

In the same manner as Example 5, human pancreatic cancer derived AsPC-1 cells were transplanted subcutaneously to the right side on the back of a 6-week-old male nude mouse (SLC, BALB/cSlc-nu/nu), and when the tumor volume (V) reached about 150 to 200 mm$^3$, the mice were separated into groups and administered with test compounds (GT-11350). Saline was administered to a control group. The compounds were administered intraperitoneally (0.1 mL/mouse) 3 times daily (one hour interval, a total of 0.2 mg/day) or once daily (0.2 mg/day), twice a week for 4 weeks. The tumor size and body weight were measured twice a week to monitor the effect of the administration of test compounds.

The results are shown in FIG. 51. GT-11350 exhibited the same anti-tumor effect for both 3 times daily and once daily administration methods.

Example 10: Additional Peptides

The following peptides are synthesized.
Ac-SCH (A$^1$) GPLT (A$^6$) VCK-NH$_2$
wherein A$^1$ and A$^6$ are independently selected from the following Table 3.

TABLE 3

| A$^1$ | A$^6$ |
|---|---|
| 4-pyridylalanine | (6-methoxyquinolin-8-yl)alanine |
| 3-pyridylalanine | (6-bromoquinolin-8-yl)alanine |
| 2-pyridylalanine | (4-fluoroquinolin-8-yl)alanine |
| 4-methoxy-Phe | (3-fluoroquinolin-8-yl)alanine |
| 3-methoxy-Phe | (3-methoxyquinolin-8-yl)alanine |
| 2-methoxy-Phe | (3-hydroxyquinolin-8-yl)alanine |
| 3-hydroxy-Phe | (2-chloroquinolin-8-yl)alanine |
| 2-hydroxy-Phe | (3-methylquinolin-2-yl)alanine |
| (1-naphthylmethyl)alanine | (4-methylquinolin-2-yl)alanine |
| (2-naphthylmethyl)alanine | (4-bromoquinolin-2-yl)alanine |
|  | (5-bromoquinolin-2-yl)alanine |
|  | (6-methoxyquinolin-2-yl)alanine |
|  | (7-methoxyquinolin-2-yl)alanine |
|  | (7-chloroquinolin-2-yl)alanine |

The modified amino acids described above can be synthesized with a known method such as a Strecker reaction using aldehyde as the starting material.

The synthesized peptides are purified to obtain pure enantiomers, which are used in the efficiency test.

The synthesis/purification of these peptides are studied by mass spectrometry in the same manner as Example 1.

Example 11: Additional Test

The same test as Example 3 is performed on the synthesized peptides.

As a result, one or more compounds shown in Table 3 is expected to exhibit an AsPC-1 cell killing effect. It is understood that certain compounds in Table 3 can exert an AsPC-1 cell killing effect particularly potently. In view of the above, these peptides are expected to be advantageously usable in applications for treating, for example, proliferative diseases (e.g., cancer), adenomyosis, and diabetic retinopathy.

(Note)

As disclosed above, the present disclosure has been exemplified by the use of its preferred embodiments. However, the above descriptions and Examples are not provided to limit the present disclosure but for the sole purpose of exemplification. Thus, it is understood that the present invention is not limited to the embodiments and Examples that are specifically described herein, and the scope thereof should be interpreted based solely on the Claims. It is also understood that any patent, patent application, and references cited herein should be incorporated herein by reference in the same manner as the contents are specifically described herein. The present application claims priority to Japanese Patent Application No. 2018-172479 filed on Sep. 14, 2018 with the JPO. The entire content thereof is incorporated herein by reference.

INDUSTRIAL APPLICABILITY

The peptide of the present disclosure was found to have a significant anti-cancer activity and has applications as a pharmaceutical product. Thus, usefulness thereof is found in industries pertaining to pharmaceutical industries and active pharmaceutical ingredient manufacturers thereof.

[Sequence Listing Free Text]

```
SEQ ID NO: 1:
SCH(A1)(A2)(A3)(A4)(A5)(A6)V(A7)(A8)

SEQ ID NO: 2:
SCHFGPLTWVCK

SEQ ID NO: 3:
X1-SCHYGPLTWVCK-X2

SEQ ID NO: 4:
X1-SCHFAPLTWVCK-X2

SEQ ID NO: 5:
X1-SCHFGALTWVCK-X2

SEQ ID NO: 6:
X1-SCHFGPATWVCK-X2

SEQ ID NO: 7:
X1-SCHFGPMTWVCK-X2

SEQ ID NO: 8:
X1-SCHFGPLTMVCK-X2

SEQ ID NO: 9:
Ac-SCHFGPLTWVCK-NH2 (YS12)

SEQ ID NO: 10:
Ac-SCHYGPLTWVCK-NH2 (GT-11261)

SEQ ID NO: 11:
Ac-SCHFAPLTWVCK-NH2 (GT-11264)

SEQ ID NO: 12:
Ac-SCHFGALTWVCK-NH2 (GT-11266)

SEQ ID NO: 13:
Ac-SCHFGPATWVCK-NH2 (GT-11268)

SEQ ID NO: 14:
Ac-SCHFGPMTWVCK-NH2 (GT-11269)

SEQ ID NO: 15:
Ac-SCHFGPLTMVCK-NH2 (GT-11270)
```

The invention claimed is:

1. A modified peptide, or a salt thereof, having a structure of Ac-SCHYGPMT(2-benzothiazolylalamino)VCK-NH$_2$ (SEQ ID NO:57), wherein an upper case letter for an amino acid indicates an L form or no enantiomer, two sulfur atoms in the two cysteines in the peptide may form a disulfide bond, and Ac indicates acetyl.

\* \* \* \* \*

UNITED STATES PATENT AND TRADEMARK OFFICE
CERTIFICATE OF CORRECTION

PATENT NO. : 12,024,571 B2
APPLICATION NO. : 17/276101
DATED : July 2, 2024
INVENTOR(S) : Hiroyuki Kouji et al.

It is certified that error appears in the above-identified patent and that said Letters Patent is hereby corrected as shown below:

On the Title Page

Item [57]:
"formula (I): V-SCH($A^1$)($A^2$)($A^3$)($A^4$)($A^5$)($A^6$)V($A^7$)($A^8$)-$X^2$"
Should read:
formula (I): $X^1$-SCH($A^1$)($A^2$)($A^3$)($A^4$)($A^5$)($A^6$)V($A^7$)($A^8$)-$X^2$ In the Claims Column 83, Claim 1, Line 28:
"Ac-SCHYGPMT(2-benzothiazolylalamino)VCK-$NH_2$"
Should read:
Ac-SCHYGPMT(2-benzothiazolylalanine)VCK-$NH_2$ Signed and Sealed this
Tenth Day of September, 2024

Katherine Kelly Vidal
*Director of the United States Patent and Trademark Office*